US011857316B2

(12) United States Patent
Alford et al.

(10) Patent No.: US 11,857,316 B2
(45) Date of Patent: Jan. 2, 2024

(54) NON-INVASIVE OPTICAL DETECTION SYSTEM AND METHOD

(71) Applicant: HI LLC, Los Angeles, CA (US)

(72) Inventors: Jamu Alford, Simi Valley, CA (US); Ashutosh Chaturvedi, Playa Vista, CA (US); Adam Marblestone, Arlington, MA (US)

(73) Assignee: HI LLC, Los Angeles, CA (US)

( * ) Notice: Subject to any disclaimer, the term of this patent is extended or adjusted under 35 U.S.C. 154(b) by 1300 days.

(21) Appl. No.: 16/382,461

(22) Filed: Apr. 12, 2019

(65) Prior Publication Data

US 2019/0336057 A1    Nov. 7, 2019

Related U.S. Application Data

(60) Provisional application No. 62/667,770, filed on May 7, 2018.

(51) Int. Cl.
*A61B 5/1455* (2006.01)
*A61B 5/00* (2006.01)

(52) U.S. Cl.
CPC ........ *A61B 5/14553* (2013.01); *A61B 5/0042* (2013.01); *A61B 5/0051* (2013.01);
(Continued)

(58) Field of Classification Search
CPC . A61B 5/14553; A61B 5/0042; A61B 5/0051; A61B 5/0066; A61B 5/0097;
(Continued)

(56) References Cited

U.S. PATENT DOCUMENTS 5,213,105 A    5/1993  Gratton et al.
5,694,938 A   12/1997  Feng et al.
(Continued)

FOREIGN PATENT DOCUMENTS

AU    2009305257    5/2014
CN     102176859    1/2014
(Continued)

OTHER PUBLICATIONS

Al-Mujaini et al., "Optical Coherence Tomography: Clinical Applications in Medical Practice," Oman Medical Journal 28(2):86-91 (2013).

(Continued)

*Primary Examiner* — Mohamed K Amara
(74) *Attorney, Agent, or Firm* — Michael J. Bolan; Vista IP Law Group, LLP

(57) ABSTRACT

In a non-invasive optical detection system and method, sample light is delivered into a scattering medium. A first portion of the sample light passing through a volume of interest exits the scattering medium as signal light, and a second portion of the sample light passing through a volume of non-interest exits the scattering medium as background light that is combined with the signal light to create a sample light pattern. Reference light is combined with the sample light pattern to create an interference light pattern having a holographic beat component. Ultrasound is emitted into the volume of non-interest in a manner that decorrelates the background light of the sample light pattern from the holographic beat component. The holographic beat component is detected during the measurement period. An optical parameter of the volume of interest is determined based on the detected holographic beat component.

44 Claims, 36 Drawing Sheets

(52) U.S. Cl.
CPC .......... *A61B 5/0066* (2013.01); *A61B 5/0097* (2013.01); *A61B 5/1455* (2013.01)

(58) Field of Classification Search
CPC ... A61B 5/1455; A61B 8/0808; A61B 8/4494; A61B 8/54; A61B 5/7203; A61B 2576/026; A61B 5/0073; A61B 5/4064; A61B 5/0261; A61B 8/06; G16H 30/40
See application file for complete search history.

(56) References Cited

U.S. PATENT DOCUMENTS

| | | |
|---|---|---|
| 5,856,667 A | 1/1999 | Spirig et al. |
| 6,041,248 A | 3/2000 | Wang |
| 6,091,983 A | 7/2000 | Alfano et al. |
| 6,205,353 B1 | 3/2001 | Alfano et al. |
| 6,334,699 B1 | 1/2002 | Gladnick |
| 6,388,739 B1 | 5/2002 | Rice |
| 6,530,944 B2 | 3/2003 | West et al. |
| 6,738,653 B1 | 5/2004 | Sfez et al. |
| 6,777,659 B1 | 8/2004 | Schwarte |
| 6,825,455 B1 | 11/2004 | Schwarte |
| 6,957,096 B2 | 10/2005 | Sfez et al. |
| 6,974,415 B2* | 12/2005 | Cerwin ............. A61B 5/416 600/407 |
| 7,053,357 B2 | 5/2006 | Schwarte |
| 7,060,957 B2 | 6/2006 | Lange et al. |
| 7,119,906 B2 | 10/2006 | Pepper et al. |
| 7,144,370 B2 | 12/2006 | Fomitchov |
| 7,444,875 B1* | 11/2008 | Wu ................ G01S 15/8979 600/443 |
| 7,498,621 B2 | 3/2009 | Seitz |
| 7,508,505 B2 | 3/2009 | Lustenberger et al. |
| 7,515,948 B1 | 4/2009 | Balberg et al. |
| 7,521,663 B2 | 4/2009 | Wäny |
| 7,541,602 B2 | 6/2009 | Metzger et al. |
| 7,560,701 B2 | 7/2009 | Oggier et al. |
| 7,586,077 B2 | 9/2009 | Lehmann et al. |
| 7,595,476 B2 | 9/2009 | Beer et al. |
| 7,620,445 B2 | 11/2009 | Tsujita |
| 7,622,704 B2 | 11/2009 | Wäny |
| 7,647,830 B2 | 1/2010 | Sfez et al. |
| 7,671,671 B2 | 3/2010 | Buettgen et al. |
| 7,701,028 B2 | 4/2010 | Kaufmann et al. |
| 7,706,862 B2 | 4/2010 | Alfano et al. |
| 7,733,742 B2 | 6/2010 | Gross et al. |
| 7,747,301 B2 | 6/2010 | Cheng et al. |
| 7,884,310 B2 | 2/2011 | Buettgen |
| 7,889,257 B2 | 2/2011 | Oggier et al. |
| 7,897,928 B2 | 3/2011 | Kaufmann et al. |
| 7,898,649 B2 | 3/2011 | Masumura |
| 7,917,312 B2 | 3/2011 | Wang et al. |
| 7,923,673 B2 | 4/2011 | Büttgen et al. |
| 8,017,858 B2 | 9/2011 | Mann |
| 8,044,999 B2 | 10/2011 | Mullen et al. |
| 8,103,329 B2 | 1/2012 | Fomitchov et al. |
| 8,106,472 B2 | 1/2012 | Kaufmann et al. |
| 8,108,022 B2 | 1/2012 | Balberg et al. |
| 8,115,158 B2 | 2/2012 | Buettgen |
| 8,126,524 B2 | 2/2012 | Balberg et al. |
| 8,143,605 B2 | 3/2012 | Metzger et al. |
| 8,190,245 B2 | 5/2012 | Mitra |
| 8,223,215 B2 | 7/2012 | Oggier et al. |
| 8,280,494 B2 | 10/2012 | Masumura |
| 8,289,502 B2 | 10/2012 | Yoshida |
| 8,299,504 B2 | 10/2012 | Seitz |
| 8,315,483 B2 | 11/2012 | Shuster |
| 8,326,567 B2 | 12/2012 | Masumura |
| 8,336,391 B2 | 12/2012 | Rokni et al. |
| 8,385,691 B2 | 2/2013 | Shuster |
| 8,400,149 B2 | 3/2013 | Stoughton et al. |
| 8,405,823 B2 | 3/2013 | Pfaff |
| 8,423,116 B2* | 4/2013 | Balberg ............ G01S 15/8968 600/407 |
| 8,450,674 B2 | 5/2013 | Yang et al. |
| 8,454,512 B2 | 6/2013 | Wang et al. |
| 8,462,355 B2 | 6/2013 | Vucinic et al. |
| 8,525,998 B2 | 9/2013 | Yaqoob et al. |
| 8,554,087 B2 | 10/2013 | Osterberg |
| 8,562,658 B2 | 10/2013 | Shoham et al. |
| 8,644,900 B2 | 2/2014 | Balberg et al. |
| 8,698,377 B2* | 4/2014 | Sinelnikov ............. A61N 7/02 310/326 |
| 8,717,574 B2 | 5/2014 | Yang et al. |
| 8,754,939 B2 | 6/2014 | Oggier et al. |
| 8,803,967 B2 | 8/2014 | Oggier et al. |
| 8,817,255 B2 | 8/2014 | Masumura |
| 8,830,573 B2 | 9/2014 | Cui et al. |
| 8,867,798 B2 | 10/2014 | Shuster |
| 8,917,442 B2 | 12/2014 | Baym et al. |
| 8,922,759 B2 | 12/2014 | Gassert et al. |
| 8,954,130 B2 | 2/2015 | Masumura |
| 8,958,622 B2 | 2/2015 | Vija et al. |
| 8,964,028 B2 | 2/2015 | Oggier |
| 8,976,433 B2 | 3/2015 | Masumura |
| 8,997,572 B2 | 4/2015 | Wang et al. |
| 9,000,349 B1 | 4/2015 | Lehmann et al. |
| 9,027,412 B2 | 5/2015 | Rokni et al. |
| 9,046,338 B2 | 6/2015 | Boccara et al. |
| 9,057,695 B2 | 6/2015 | Masumura |
| 9,076,709 B2 | 7/2015 | Felber et al. |
| 9,086,365 B2 | 7/2015 | Wang et al. |
| 9,117,712 B1 | 8/2015 | Oggier et al. |
| 9,131,170 B2 | 9/2015 | Mandelis et al. |
| 9,131,880 B2 | 9/2015 | Balberg et al. |
| 9,140,795 B2 | 9/2015 | Lehmann et al. |
| 9,164,033 B2 | 10/2015 | Edwards et al. |
| 9,195,041 B2 | 11/2015 | Redford |
| 9,200,887 B2 | 12/2015 | Potsaid et al. |
| 9,209,327 B2 | 12/2015 | Neukom et al. |
| 9,226,666 B2 | 1/2016 | Wang et al. |
| 9,232,896 B2 | 1/2016 | Baym et al. |
| 9,234,841 B2 | 1/2016 | Wang et al. |
| 9,237,850 B2 | 1/2016 | Metzger et al. |
| 9,282,931 B2 | 3/2016 | Tearney et al. |
| 9,304,490 B2 | 4/2016 | Masumura |
| 9,313,423 B2 | 4/2016 | Wang et al. |
| 9,329,035 B2 | 5/2016 | Oggier |
| 9,335,154 B2 | 5/2016 | Wax et al. |
| 9,335,605 B2 | 5/2016 | Wang et al. |
| 9,341,715 B2 | 5/2016 | Buettgen et al. |
| 9,351,705 B2 | 5/2016 | Wang et al. |
| 9,435,891 B2 | 9/2016 | Oggier |
| 9,442,196 B2 | 9/2016 | Buettgen et al. |
| 9,466,938 B2 | 10/2016 | Dupret et al. |
| 9,486,128 B1 | 11/2016 | Hannaford et al. |
| 9,488,573 B2 | 11/2016 | Edwards et al. |
| 9,528,966 B2 | 12/2016 | Wang et al. |
| 9,555,444 B2 | 1/2017 | Goodman et al. |
| 9,619,486 B2 | 4/2017 | Shuster |
| 9,655,527 B2 | 5/2017 | Wang et al. |
| 9,658,510 B2 | 5/2017 | Kiooelen et al. |
| 9,664,606 B2 | 5/2017 | Hajjarian et al. |
| 9,668,672 B2 | 6/2017 | Zalevsky et al. |
| 9,698,196 B2 | 7/2017 | Buettgen et al. |
| 9,713,448 B2 | 7/2017 | Caplan et al. |
| 9,720,505 B2 | 8/2017 | Gribetz et al. |
| 9,730,649 B1 | 8/2017 | Jepsen |
| 3,013,467 A1 | 12/2017 | Minsky |
| 9,839,365 B1 | 12/2017 | Homyk et al. |
| 10,016,137 B1* | 7/2018 | Yang ............... A61B 5/0042 |
| 10,203,274 B2* | 2/2019 | Ruan ............... A61B 5/0097 |
| 10,219,700 B1* | 3/2019 | Yang .............. G01B 9/02091 |
| 10,349,917 B2* | 7/2019 | Boctor ............... A61B 8/461 |
| 10,359,400 B2* | 7/2019 | Wang ............... A61B 5/0095 |
| 11,320,588 B1* | 5/2022 | Mazed ............... G16H 10/40 |
| 11,547,303 B2* | 1/2023 | Ruan ............... A61B 5/0066 |
| 2004/0080754 A1 | 4/2004 | Tobiason |
| 2005/0085725 A1 | 4/2005 | Nagar et al. |
| 2005/0143664 A1* | 6/2005 | Chen ............... A61B 5/6852 600/478 |
| 2005/0256403 A1 | 11/2005 | Fomitchov |
| 2006/0023621 A1 | 2/2006 | Hwang et al. |
| 2006/0025659 A1 | 2/2006 | Kiguchi |

(56) References Cited

U.S. PATENT DOCUMENTS

| | | | |
|---|---|---|---|
| 2006/0058614 A1* | 3/2006 | Tsujita | A61B 5/0073 600/407 |
| 2006/0063985 A1 | 3/2006 | Hogan | |
| 2006/0122475 A1 | 6/2006 | Balberg et al. | |
| 2006/0184042 A1 | 8/2006 | Wang et al. | |
| 2006/0184049 A1 | 8/2006 | Tsujita | |
| 2006/0187533 A1 | 8/2006 | Nielsen et al. | |
| 2006/0224053 A1 | 10/2006 | Black et al. | |
| 2006/0247506 A1 | 11/2006 | Balberg et al. | |
| 2006/0253007 A1 | 11/2006 | Cheng et al. | |
| 2006/0264717 A1 | 11/2006 | Pesach et al. | |
| 2007/0088206 A1* | 4/2007 | Peyman | A61B 5/14532 600/319 |
| 2007/0093702 A1 | 4/2007 | Yu et al. | |
| 2008/0024767 A1 | 1/2008 | Seitz | |
| 2008/0174785 A1 | 7/2008 | Seitz et al. | |
| 2008/0219584 A1 | 9/2008 | Mullen et al. | |
| 2008/0296514 A1 | 12/2008 | Metzger et al. | |
| 2008/0312533 A1 | 12/2008 | Balberg et al. | |
| 2009/0066949 A1 | 3/2009 | Masumura | |
| 2009/0069674 A1 | 3/2009 | Masumura et al. | |
| 2009/0069676 A1 | 3/2009 | Nishihara | |
| 2009/0069685 A1 | 3/2009 | Nishihara et al. | |
| 2009/0069687 A1 | 3/2009 | Igarashi | |
| 2009/0124902 A1 | 5/2009 | Herrmann | |
| 2009/0171210 A1 | 7/2009 | Wang | |
| 2009/0253989 A1 | 10/2009 | Caplan et al. | |
| 2009/0264722 A1 | 10/2009 | Metzger et al. | |
| 2009/0312628 A1* | 12/2009 | Igarashi | A61B 5/0073 356/51 |
| 2010/0000330 A1 | 1/2010 | Rokni et al. | |
| 2010/0069750 A1 | 3/2010 | Masumura | |
| 2010/0070233 A1 | 3/2010 | Masumura | |
| 2010/0073674 A1 | 3/2010 | Yoshida | |
| 2010/0152559 A1 | 6/2010 | Cheng et al. | |
| 2010/0152591 A1 | 6/2010 | Yu et al. | |
| 2010/0249562 A1* | 9/2010 | Zhang | G01B 9/0203 600/443 |
| 2010/0276573 A1 | 11/2010 | Duerksen | |
| 2010/0285518 A1 | 11/2010 | Viator et al. | |
| 2011/0071402 A1 | 3/2011 | Masumura | |
| 2011/0101241 A1 | 5/2011 | Cottier et al. | |
| 2011/0122416 A1* | 5/2011 | Yang | A61B 5/0059 29/428 |
| 2011/0172513 A1 | 7/2011 | Nakajima et al. | |
| 2011/0228097 A1 | 9/2011 | Motta | |
| 2011/0237956 A1 | 9/2011 | Edwards et al. | |
| 2011/0249912 A1 | 10/2011 | Shuster | |
| 2011/0282192 A1* | 11/2011 | Axelrod | A61B 5/0066 600/427 |
| 2012/0022381 A1 | 1/2012 | Tearney et al. | |
| 2012/0070817 A1 | 3/2012 | Wang et al. | |
| 2012/0127557 A1 | 5/2012 | Masumura | |
| 2012/0204648 A1* | 8/2012 | Wang | G01N 29/2418 359/305 |
| 2012/0275262 A1 | 11/2012 | Song et al. | |
| 2014/0088429 A1* | 3/2014 | Lomes | A61B 8/145 600/443 |
| 2014/0204389 A1 | 7/2014 | Mukoh | |
| 2014/0218748 A1 | 8/2014 | Wax et al. | |
| 2015/0238092 A1 | 8/2015 | Masumura | |
| 2015/0245771 A1 | 9/2015 | Wang et al. | |
| 2015/0320319 A1 | 11/2015 | Alfano et al. | |
| 2016/0058395 A1 | 3/2016 | Muser | |
| 2016/0187533 A1 | 6/2016 | Maucec et al. | |
| 2016/0235305 A1 | 8/2016 | Wang et al. | |
| 2016/0249812 A1 | 9/2016 | Wang et al. | |
| 2016/0299218 A1 | 10/2016 | Lehmann | |
| 2016/0305914 A1 | 10/2016 | Wang et al. | |
| 2017/0038000 A1 | 2/2017 | Fuchsle et al. | |
| 2017/0038300 A1 | 2/2017 | Dake et al. | |
| 2017/0038459 A1 | 2/2017 | Kubacki et al. | |
| 2017/0049326 A1 | 2/2017 | Alfano | |
| 2017/0065182 A1 | 3/2017 | Wang et al. | |
| 2017/0090018 A1 | 3/2017 | Buettgen et al. | |
| 2017/0105636 A1 | 4/2017 | Wang et al. | |
| 2017/0122915 A1 | 5/2017 | Vogt et al. | |
| 2017/0176250 A1 | 6/2017 | Rae et al. | |
| 2019/0313912 A1* | 10/2019 | Alford | G01N 21/49 |
| 2019/0336001 A1* | 11/2019 | Zhou | A61B 5/7257 |
| 2019/0336006 A1* | 11/2019 | Horstmeyer | A61B 5/6814 |
| 2019/0336007 A1* | 11/2019 | Ruan | A61B 5/0066 |
| 2019/0336060 A1* | 11/2019 | Shen | G01B 9/02091 |
| 2019/0391213 A1* | 12/2019 | Alford | G01R 33/0094 |
| 2020/0025844 A1* | 1/2020 | Alford | G01R 33/0094 |
| 2021/0275083 A1* | 9/2021 | Johnson | G06F 3/015 |
| 2021/0294884 A1* | 9/2021 | Lasser | H04L 9/3231 |

FOREIGN PATENT DOCUMENTS

| | | |
|---|---|---|
| CN | 104107051 | 10/2014 |
| CN | 104382558 | 3/2015 |
| EP | 1458087 | 10/2005 |
| EP | 1771844 | 4/2007 |
| EP | 2016891 | 1/2009 |
| EP | 2036487 | 3/2009 |
| EP | 2036488 | 3/2009 |
| EP | 2036490 | 3/2009 |
| EP | 2163189 | 3/2010 |
| EP | 1675501 | 9/2013 |
| EP | 1771882 | 9/2013 |
| EP | 2240798 | 8/2016 |
| EP | 2016891 | 10/2016 |
| EP | 2594959 | 1/2017 |
| EP | 2815251 | 3/2017 |
| JP | 2009501581 | 1/2009 |
| WO | WO2005025399 | 3/2005 |
| WO | WO2005025399 | 5/2005 |
| WO | WO2006025649 | 3/2006 |
| WO | WO2006093666 | 9/2006 |
| WO | WO2007035934 | 3/2007 |
| WO | WO2008040771 | 4/2008 |
| WO | WO2008040771 | 8/2008 |
| WO | WO2010043851 | 4/2010 |
| WO | WO2012080837 | 6/2012 |
| WO | WO2012080838 | 6/2012 |
| WO | WO2014106823 | 7/2014 |
| WO | WO2016138637 | 9/2016 |
| WO | WO2016193554 | 12/2016 |

OTHER PUBLICATIONS

Atlan,M. et al., Pulsed acousto-optic imaging in dynamic scattering media with heterodyne parallel speckle detection, Optics Letters, vol. 30, No. 11, Jun. 1, 2005, 1360-1362.

Blanc, et al., "Smart Pixels for Real-time Optical Coherence Tomography," Proceedings of SPIE—The International Society of Optical Engineering, 13 pages (2004).

Broussard GJ, Liang R, Tian L., Monitoring activity in neural circuits with genetically encoded indicators, Frontiers in molecular neuroscience, 2014;7.

Choma, Michael A. et al., Instantaneous quadrature low-coherence interferometry with 3 × 3 fiber-optic couplers, Optic Letters, vol. 28, No. 22, Nov. 15, 2003, 2162-2164.

D.S. Elson, et al. Ultrasound-mediated optical tomography: a review of current methods, Interface Focus, vol. 1, No. 4, Jun. 2, 2011, 632-648.

Dunsby C et al: "Techniques for Depth-Resolved Imaging Through Turbid Media Including Coherence-Gated Imaging", Journal of Physics D: Applied Physics, Institute of Physics Publishing Ltd, GB, vol. 36, Jan. 1, 2003 (Jan. 1, 2003), pp. R207-R227.

Franceschini MA, Fantini S, Toronov V, Filiaci ME, Gratton E., "Cerebral hemodynamics measured by near-infrared spectroscopy at rest and during motor activation". In Proceedings of the Optical Society of America in Vivo Optical Imaging Workshop 2000 (pp. 73-80), Optical Society of America.

Franceschini, MA and Boas, DA, "Noninvasive Measurement of Neuronal Activity with Near-Infrared Optical Imaging," Neuroimage, vol. 21, No. 1, pp. 372-386 (Jan. 2004)).

(56) References Cited

OTHER PUBLICATIONS

Giacomelli, Michael G. et al., Imaging beyond the ballistic limit in coherence imaging using multiply scattered light, Optics Express, Feb. 28, 2011, vol. 19, No. 5, 4268-4279.

Goense J, Merkle H, Logothetis NK, "High-resolution of fMRI reveals laminar differences in neurovascular coupling between positive and negative BOLD responses". Neuron, Nov. 8, 2012; 76(3):629-39.

Gratton G, Fabiani M., "Fast optical imaging of human brain function", Frontiers in human neuroscience, 2010;4.

Gratton Gabriele et al., "Dynamic brain imaging: Event-related optical signal (EROS) measures of the time course and localization of cognitive-related activity", Psychonomic Bulletin & Review, 1998, 5 (4), 535-563.

Guillaume, Emilie Benoit, et al. Acousto-optical coherence tomography with a digital holographic detection scheme, Optics Letters, vol. 37, No. 15, Aug. 1, 2012.

Hale, Thomas C. et al., Photorefractive optical lock-in vibration spectral measurement, Applied Optics, vol. 36, No. 31, Nov. 1, 1997, 8248-8258.

HeliCam C3, retrieved on Dec. 6, 2017 on the Internet at http://www.heliotis.ch/html/lockl nCameraC3.htm, 2 pages.

Heliotis: "High-speed Lock-IN CMOS camera with pixel-level signal processing", Nov. 25, 2015 (Nov. 25, 2015).

Horinaka H, Osawa M. Hashimoto K, Wada K, Cho Y., "Extraction of quasi-straightforward-propagating photons from diffused light transmitting through a scattering medium by polarization modulation". Optics Letters, Jul. 1, 1995; 20(13):1501-3.

Horstmeyer R., Ruan H, Yang C, "Guidestar-Assisted Wavefront-Shaping Methods for Focusing Light into Biological Tissue," Nature Photonics, vol. 9, No. 9, pp. 563-571 (Sep. 1, 2015).

Huang, Chuanyoung, et al., Ultrasound-enhanced optical coherence tomography: improved penetration and resolution, J. Opt. Soc. Am. A/vol. 25, No. 4/ Apr. 2008, p. 938-346.

Khoury, Jehad et al., Photorefractive optical lock-in detector, Optics Letters, vol. 16, No. 18, Sep. 15, 1991, 1442-1444.

Kim, "Biomedical Imaging Applications of Parallel Optical Coherence Tomography and Adaptive Optics," Jeehyum Kim dissertation, The University of Texas at Austin, 168 pages (2004).

Laforest T, Verdant A, Dupret G, Gigan S., Ramaz F, Tessier G, "Co-Integration of a Smart CMOS Image Sensor and a Spatial Light Modulator for Real-Time Optical Phase Modulation," Proc. of SPIE-IS&T, vol. 2014, 9022:90220N-1 (Mar. 2014).

Lange, et al., "Demodulation pixels in CCD and CMOS technologies for time-of-flight ranging," InProc. SPIE 3965:177-188 (2000).

Lesaffre, Max, et al. Experimental study of z resolution in Acousto-Optical Coherence Tomography using random phase jumps on ultrasound and light, Physics Optics, arXiv:1302.1343v1, Feb. 6, 2013 p. 1-9.

Leveque S, Boccara AC, Lebec M, Saint-Jalmes H, "Ultrasonic tagging of photon paths in scattering media: parallel speckle modulation processing". Optics Letters, Feb. 1, 1999; 24(3):181-3.

Li, Youzhi et al., Pulsed ultrasound-modulated optical tomography using spectral-hole burning as a narrowband spectral filter, Applied Physics Letter, 93, 011111 {2008).

Liu Y, Ma C, Shen Y, Wang LV, "Bit-Efficient, Sub-Millisecond Wavefront Measurement Using a Lock-In Camera for Time-Reversal Based Optical Focusing Inside Scattering Media," Optics Letters, vol. 41, No. 7, pp. 1321-1324, Apr. 1, 2016.

Liu Y, Shen Y, Ma C, Shi J, Wang LV, "Lock-in Camera Based Heterodyne Holography for Ultrasound-Modulated Optical Tomography Inside Dynamic Scattering Media," Applied Physics Letters, vol. 108, No. 23, 231106, Jun. 6, 2016.

Loic Blanchot, et al., "Low-coherence in-depth microscopy for biological tissue imaging: design of a real-time control system", PROC. SPIE, vol. 3194, Jan. 1, 1998 (Jan. 1, 1998), pp. 198-204.

Mahan GD, Engler WE, Tiemann JJ, Uzgiris E, "Ultrasonic Tagging of Light: Theory," Proceedings of the National Academy of Sciences, vol. 95, No. 24, pp. 14015-14019, Nov. 24, 1998.

Mao, Shu et al., Optical Lock-In Detection of FRET Using Synthetic and Genetically Encoded Optical Switches, Biophysical Journal, vol. 94, Jun. 2008, 4515-4524.

Marriott, Gerard et al. Optical lock-in detection imaging microscopy for contrast-enhanced imaging in living cells, PNAS, Nov. 18, 2008, vol. 105, No. 46, 17789-17794.

Matthews, Thomas E. et al. Deep tissue imaging using spectroscopic analysis of multiply scattered light, Optica, vol. 1, No. 2, Aug. 2014, 105-111.

Monte Carlo, extreme (MCX), retrieved on Dec. 16, 2017 from http://mcx.sourceforge.net/cgi-bin/index.cgi, 2 pages.

Patwardhan SV, Culver JP. Quantitative diffuse optical tomography for small animals using an ultrafast gated image intensifier. Journal of biomedical optics. Jan. 1, 2008; 13(1):011009.

PCT International Search Report and Written Opinion for International Appln. No. PCT/US2018/041324, Applicant HI LLC, forms PCT/ISA/210, 220 and 237 dated Oct. 18, 2018 (14 pages).

Powell S., Srridge SR, Leung TS, "Gradient-Based Quantitative Image Reconstruction in Ultrasound-Modulated Optical Tomography: First Harmonic Measurement Type in a Linearized Diffusion Formulation," IEEE Transactions on Medical Imaging, vol. 35, No. 2, pp. 456-467 (Feb. 2016).

Popescu, et al., "Optical coherence tomography: fundamental principles, instrumental designs and biomedical applications," Biophys Rev 3:155-169 (2011).

Puszka, Agathe et al., Time-resolved diffuse optical tomography using fast-gated single-photon avalanche diodes, Aug. 1, 2013, vol. 4, No. 8, DOI:10_1364/BOE.4.001351, Biomedical Optics Express, 1351-1365.

Qureshi MM, Brake J., Jeon HJ, Ruan H, Liu Y, Safi AM, Eom TJ, Yang C., Chung E, "In Vivo Study of Optical Speckle Decorrelation Time Across Depths in the Mouse Brain," Biomedical Optics Express, vol. 8, No. 11, pp. 4855-4864 (Nov. 1, 2017).

Ruan, Haowen et al., Pulsed ultrasound modulated optical tomography with harmonic lock-in holography detection, J. Opt. Soc. Am. A, vol. 30, No. 7, Jul. 2013, 1409-1416.

Sakadzic S, Wang LV, "High-Resolution Ultrasound-Modulated Optical Tomography in Biological Tissues," Optics Letters, vol. 29, No. 23, pp. 2770-2772, Dec. 1, 2004).

Schenk, John O., et al., Ultrasound induced improvement in optical coherence tomography (OCT) resolution, PNAS, Jul. 23, 2002 vol. 99 No. 15, p. 9761-9764.

Schmitt, JM, Gandjbackhche, AH, Bonner RF, "Use of polarized light to discriminate short-part photons in a multiply scattering medium". Applied Optics, Oct. 20, 1992; 31(30):6535-46.

Singh M. et al. Assessment of ultrasound modulation of near infrared light on the quantification of scattering coefficient, Medical Physics, vol. 37, No. 7, Jun. 28, 2010, 3744-3751.

Steinbrink J, Villringer A, Kempf F, Haux D. Boden S, Obrig H., "Illuminating the BOLD Signal: Combined fMRI-fNIRS Studies," Magnetic Resonance Imaging, vol. 24, No. 4, pp. 495-505, May 31, 2006).

Strauss, Charlie E.M. et al., Synthetic—array heterodyne detection: a single-element detector acts as an array, Oct. 15, 1994, vol. 19, No. 20, Optics Letters, 1609-1611.

Thrane, et al., "Complex decorrelation averaging in optical coherence tomography: a way to reduce the effect of multiple scattering and improve image contrast in a dynamic scattering medium," Opt Lett. 42(14):2738-2741 (2017).

Tucker-Schwartz, Jason M. et al., Photothermal optical lock-in optical coherence tomography for in vivo imaging, Jun. 1, 2015, vol. 6, No. 6, DOI:10.1364/BOE.6.002268, Biomedical Optics Express, 2268-2282.

Van der Laan JD, Wright JB, Scrymgeour DA, Kemme SA, Dereniak EL, "Evolution of circular and linear polarization in scattering environments", Optics Express, Dec. 14, 2015; 23(25):31874-88.

Yaqoob, Zahid et al., Harmonically-related diffraction gratings-based interferometer for quadrature phase measurments, Sep. 4, 2006, vol. 14, No. 18, Optics Express, 8127-8137.

Wang YM, Judkewitz B, DiMarzio CA, Yang C., "Deep-Tissue Focal Fluorescence Imaging with Digitally Time-Reversed Ultrasound-Encoded Light," Nature Communications, vol. 3, Article 928 (Jun. 16, 2012).

(56) References Cited

OTHER PUBLICATIONS

Wang, RK, Jacques SL, Ma Z, Hurst S, Hanson SR, Gruber A, Three dimensional optical angiography. Optics Express, Apr. 2, 2007; 15(7):4083-97.

Xu X, Liu H., Wang LV, "Time-Reversed Ultrasonically Encoded Optical Focusing into Scattering Media," Nature Photonics, vol. 5, No. 3, pp. 154-157 (Mar. 1, 2011).

* cited by examiner

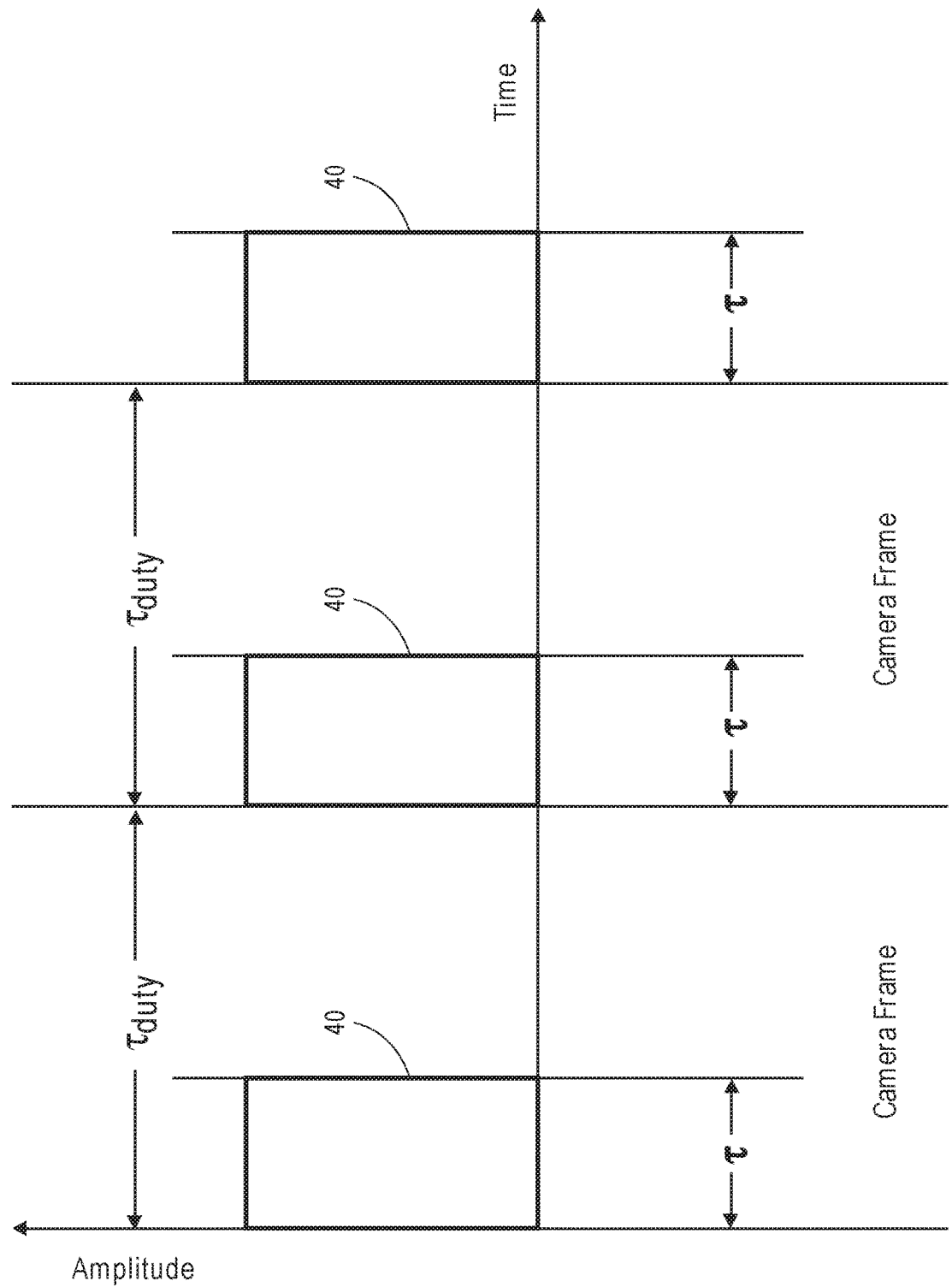

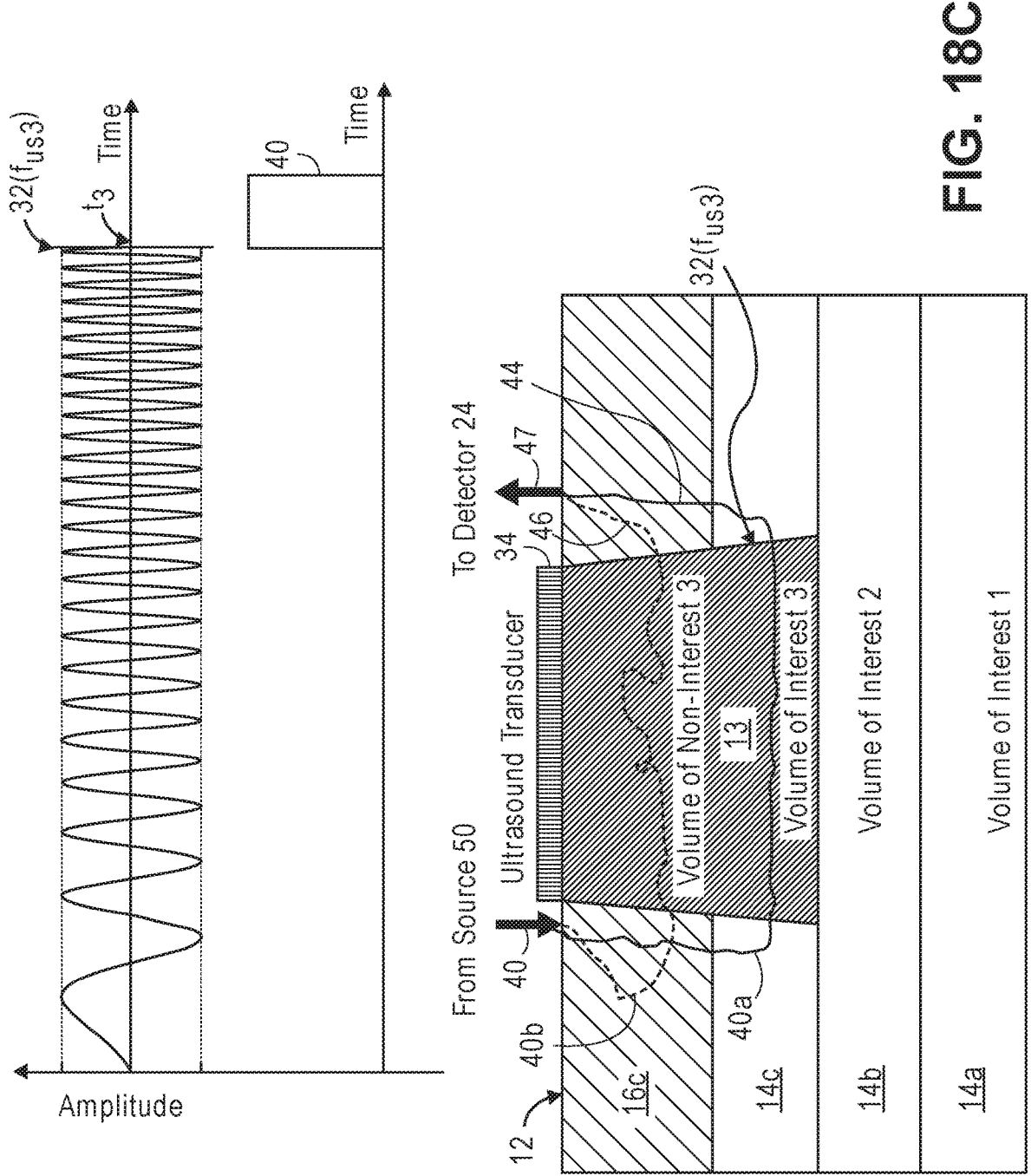

NON-INVASIVE OPTICAL DETECTION SYSTEM AND METHOD

RELATED APPLICATION DATA

This application claims the benefit of U.S. Provisional Patent Application 62/667,770, filed May 7, 2018, which is expressly incorporated herein by reference.

FIELD OF THE INVENTION

The present invention relates to methods and systems for detecting optical parameters in a scattering medium, and in particular, methods and systems related to non-invasively detecting physiologically dependent optical parameters in the human body, e.g., the brain.

BACKGROUND OF THE INVENTION

Measuring neural activity in the brain is useful for medical diagnostics, neuromodulation therapies, neuroengineering, or brain-computer interfacing. Conventional methods for measuring neural activity in the brain include diffusive optical imaging techniques, which employ moderate amounts of near-infrared or visible light radiation, thus being comparatively safe and gentle for a biological subject in comparison to X-Ray Computed Tomography (CT) scans, positron emission tomography (PET), or other methods that use higher-energy and potentially harmful radiation. Moreover, in contrast to other known methods, such as functional magnetic resonance imaging (fMRI), these optically-based imaging methods do not require large magnets or magnetic shielding, and thus, can be scaled to wearable or portable form factors, which is especially important in applications, such as brain-computer interfacing.

Optical Coherence Tomography (OCT) is one possible method to perform non-invasive measurement of brain activity using near-infrared light. In an OCT system, light from a light source is split into two paths along two different arms of an interferometer: a reference arm and a sample arm. In the sample arm, sample light is backscattered through a sample medium, and in the reference arm, reference light is back-reflected by a mirror where it recombines with the backscattered sample light at a coupler. An interference light pattern is formed by any sample light that has an optical path length that matches, within the coherence length of the optical source, the optical path length traveled by the reference light. The intensity of the backscattering sample light having that optical path length can then be detected within the interference light pattern. The optical path length of the reference light may be tuned by adjusting the position of the mirror, such that only sample light having the matching optical path length is selected for detection.

One primary difficulty, when applying OCT to imaging the human brain, is that the neural activity of interest produces a relatively small signal, which is masked behind a much larger background signal arising from light that does not reach the surface of the brain, but instead "wanders" in the scalp and skull before eventually being collected by a detector.

For example, as shown in FIG. 1, a rudimentary representation of a conventional OCT system 1 for use in brain imaging comprises, among other components, a paired optical source 2 and optical detector 3. The optical source 2 emits sample light 4 through the scalp 5 (including skin, aponeurosis, and periosteum), the skull 6, and into the grey matter 7, where it is passes through the target tissue voxel 8 within the grey matter 7 back through the grey matter 7, skull 6, and the scalp 5 to the optical detector 3. Although the sample light 4 will also traverse the meninges (dura mater, arachnoid, and pia mater) and cerebral spinal fluid (CSF) between the skull 6 and grey matter 7, these anatomical elements have not been illustrated for purposes of brevity in explanation.

Optimally, all of the sample light 4 received at the optical detector 3 will be back-scattered by the target tissue voxel 8. However, as shown in FIG. 2, the sample light 4 is highly scattered by the scalp 5, skull 6, and grey matter 7, such that the photons of the sample light 4 take various paths from the source 2 to the optical detector 3, a very small minority of which pass through the target tissue voxel 8.

As shown in FIG. 3, using path-length selection, an OCT technique may eliminate some of the photons that have not propagated through the target tissue voxel 8. However, due to the highly scattering properties of the skull 6, some of the photons that do not penetrate entirely through the skull 6, but wander in the scalp 5 and skull 6, may travel along an optical path that matches the optical path length of the targeted photons (i.e., the photons that propagate through the target tissue voxel 8) within the coherence length of the optical source 2, and thus, will serve as undesirable background contamination to the sample light 4 that is encoded with the optical parameters of the target tissue voxel 8.

That is, although the OCT technique separates photons based on optical path length, it fails to separate out photons that travel to the grey matter 7 in a relatively straight path (i.e., the "grey matter photons") and some of the photons that wander around the scalp 5 and skull 6 (i.e., the "skull photons") from each other, as further illustrated in FIG. 4. This is not a trivial issue as the ratio between the "straight-path" photons that return to the optical detector 3 from the target tissue voxel 8, and the number of photons that wander around the scalp 5 and skull 6 and then return to the optical detector 3, is roughly 1:1000.

In particular, using a Monte Carlo (MC) model (which is a computer simulation based on a pseudo-random number generator that models the random nature of the light as it diffuses through a scattering medium, such as the human skull and brain) of the scalp 5, skull 6, and grey matter 7, it can be shown that, given a geometric path length for a target tissue voxel 8 that is 12.0 mm deep, and a source-detector separation of 0.0 mm, the number of detected photons that pass through the target tissue voxel 8 and the number of detected photons that miss the target tissue voxel 8, each expressed as a fraction of the total photons emitted by the source 2, can be plotted against the optical path length, as illustrated in FIG. 5. At a targeted optical path length of 75 mm, the fractional number of detected skull photons is approximately $1 \times 10^{-6}$, whereas the fractional number of detected grey matter photons is approximately $1 \times 10^{-9}$, a ratio of approximately 1:1000.

Thus, the light that wanders around in the scalp 5 and skull 6 is much more intense than the light that returns from the target tissue voxel 8, and thus, may overwhelm the signal. One technique used by OCT systems to reduce the fraction of unwanted light from the scalp 5 and skull 6 is to separate the source 2 and the optical detector 3 a relatively long distance from each other (e.g., in the range of several centimeters). However, this solution results in a significant loss of detected photons and significantly decreases the imaging spatial resolution.

Ultrasound Modulated Optical Tomography (UOT) attempts to solve this problem by ultrasound "tagging" of the light that reaches the target tissue voxel within the brain while suppressing all untagged light in order to resolve only the tagged light (see U.S. Pat. No. 8,423,116; and Sakadzic S, Wang L V, "High-Resolution Ultrasound-Modulated Optical Tomography in Biological Tissues," Optics Letters, Vol. 29, No. 23, pp. 2770-2772, Dec. 1, 2004).

In UOT, an ultrasound beam with a highly localized focus, e.g., millimeter or sub-millimeter in size, is used to selectively perturb (i.e., "tag") light (e.g., light generated by a near-infrared coherent laser) passing through the target tissue voxel. Due to the acousto-optic effect, light passing through the ultrasonic beam undergoes a frequency shift defined by multiples of the ultrasonic frequency. By detecting the frequency-shifted light, i.e., the tagged light, spatial information characterizing the biological tissue within the voxel can be acquired.

One consideration that must be taken into account in the context of UOT, is that the size of the target tissue voxel in the brain depends on the focal size of the ultrasound beam. However, only relatively low-frequency ultrasound passes through to the brain, because the diffraction and attenuation mechanisms of the skull result in ultrasound losses. In this case, low frequency is roughly defined as any frequency equal to or below 1 MHz, while high frequency is roughly defined as any frequency above 1 MHz. As an approximate rule, ultrasound in the skull is attenuated at least 10 dB/cm/MHz. Thus, at 1 MHz, ultrasound experiences a 10-dB loss through one centimeter of skull; at 2 MHz, ultrasound experiences a 20-dB loss through one centimeter of skull; at 3 MHz, ultrasound experiences a 30-dB loss through one centimeter of skull; and so forth. As a result, there is a theoretical lower bound to the size of the target tissue voxel as it is difficult to focus ultrasound to less than one half of its wavelength, and in practice, it can typically only be focused to about 1 wavelength. The wavelength of ultrasound in brain tissue is about 1.5 mm for 1 MHz, so in practice, it is difficult to achieve resolution smaller than around 1.5 mm$^3$.

Another consideration that must be taken into account in the context of UOT is that, in practice, only a small percentage of the light that reaches the target tissue voxel is tagged with the ultrasound. This percentage is on the order of a few percent and scales with the size of the target tissue voxel. That is, the ultrasound tagging efficiency (i.e., the number of tagged photons relative to a number of untagged photons scattered by the target tissue voxel) varies inversely to the size of the target tissue voxel.

One disadvantage that has not been addressed in the context of UOT is that a relatively large, expensive, and complex transducer (e.g., a phased array of transducers) is required to focus the ultrasound at the relatively small target tissue voxel, and a bubble-free liquid ultrasound medium must typically be used to ensure that there is sufficient ultrasound coupling between the ultrasound transducer and the scalp.

Therefore, there remains a need to provide a non-invasive optical detection system that does not require focused ultrasound to tag a target tissue voxel within brain tissue, and still eliminates undesirable light from paths that remain largely outside of the brain, such as the skull photons, from the optical detected measurements.

SUMMARY OF THE INVENTION

In accordance with one aspect of the present inventions, a non-invasive optical detection system comprises an interferometer configured for delivering sample light, during a measurement period, into a scattering medium having a volume of interest and a volume of non-interest. A first portion of the sample light passing through the volume of interest exits the scattering medium as signal light, and a second portion of the sample light passing through the volume of non-interest exits the scattering medium as background light that is combined with the signal light to create a sample light pattern. The interferometer is further configured for combining reference light with the sample light pattern (e.g., using a homodyne technique or a heterodyne technique) to create at least one interference light pattern (e.g., a speckle light pattern), each having a holographic beat component. The interferometer may comprise an optical source configured for generating source light, and an optical beam splitter configured for splitting the source light into the sample light and reference light.

The interference light pattern(s) may comprise a plurality of phase-modulated interference light patterns, e.g., two phase-modulated interference light patterns having phases of 0 and $\pi$. The interferometer may be configured for concurrently combining the sample light pattern and reference light having different phases to respectively generate the phase-modulated interference light patterns.

In one embodiment, the interferometer comprises a reference arm along which the reference light propagates, and a sample arm along which the sample light propagates. The reference arm and sample arm have optical path lengths that match within a coherence length of the sample light, and the frequency of the sample light and the reference light are the same, such that the holographic beat component of each of the interference light pattern(s) is constant. In this embodiment, the optical path length of the reference arm of the interferometer may be adjustable, and a controller may be provided for operating the interferometer to adjust the optical path length of the reference arm.

The optical detection system further comprises an acoustic assembly configured for emitting ultrasound into the volume of non-interest that decorrelates at least a portion of the background light of the sample light pattern from the holographic beat component of each of the interference light pattern(s). In one embodiment, the acoustic assembly is configured for emitting ultrasound into the volume of non-interest that decorrelates substantially all of the background light of the sample light pattern from the holographic beat component of each of the interference light pattern(s). In another embodiment, the acoustic assembly is configured for emitting ultrasound into the volume of non-interest that decorrelates at least ninety-nine percent of the background light of the sample light pattern from the holographic beat component of each of the interference light pattern(s).

In one embodiment, the acoustic assembly comprises a single-element ultrasound transducer (e.g., a thin-film ultrasound transducer, such as, e.g., a capacitive micromachined ultrasound transducer (CMUT) or a piezo micromachined ultrasound transducers (PMUT)) configured for emitting the ultrasound into the volume of non-interest. The ultrasound may have a frequency greater than 1 MHz, e.g., in the range of 5-20 MHz, and be unfocused.

In one embodiment, the ultrasound has a uniform frequency, a uniform amplitude, and a uniform phase during the measurement period. In another embodiment, the optical detection system further comprises a controller configured for operating the acoustic assembly to vary at least one, and perhaps even two or more, of a frequency, an amplitude, and a phase during the measurement period. If the controller is configured for operating the acoustic assembly to vary the frequency of the ultrasound during the measurement period, the controller may be configured for operating the acoustic assembly to sweep the frequency of the ultrasound during the measurement period or randomly vary the frequency of the ultrasound during the measurement period.

In one embodiment, the ultrasound is continuous wave (CW) ultrasound that has a frequency, such that all of the ultrasound emitted into the scattering medium during the measurement period is substantially confined within the volume of non-interest. In another embodiment, the ultrasound is pulsed wave (PW) ultrasound that has a frequency that allows it to penetrate into the volume of interest. In this case, the optical detection system may further comprise a controller configured for operating the interferometer and the acoustic assembly to pulse the sample light and the ultrasound in synchrony during the measurement period, such that all of the ultrasound emitted into the scattering medium during the measurement period is substantially confined within the volume of non-interest.

The optical detection system further comprises at least one detector configured for detecting the holographic beat component of each of the interference light pattern(s) during the measurement period. In one embodiment, each of the interference light pattern(s) comprises spatial components, and each the detector(s) comprises an array of detector pixels respectively configured for detecting intensities of the spatial components of the interference light pattern(s).

The optical detection system further comprises a processor configured for determining an optical parameter of the volume of interest based on detected holographic beat component of each of the interference light pattern(s). In one embodiment, the scattering medium is an anatomical structure, in which case, the volume of interest may comprise a target tissue voxel within the anatomical structure, and the optical parameter may be a physiologically-dependent optical parameter of the target tissue voxel, e.g., a level of deoxygenated and/or oxygenated hemoglobin concentration or relative abundance. If the target tissue voxel comprises grey matter of a brain matter, the volume of non-interest may comprise a scalp and skull, and the processor may be further configured for determining neural activity within the target tissue voxel based on the determined physiologically-dependent optical parameter. In this case, the physiologically-dependent optical parameter may be a fast-optical signal.

In an optional embodiment, the volume of interest is a first volume of interest, the volume of non-interest is a first volume of non-interest, the measurement period is a first measurement period, the sample light is a first sample light, and the interference light pattern(s) is a first interference light pattern(s). The interferometer is configured for emitting the sample light into the scattering medium having a second volume of interest and a second volume of non-interest during a second measurement period. A first portion of the second sample light passing through the second volume of interest exits the scattering medium as signal light, and a second portion of the second sample light passing through the second volume of non-interest exits the scattering medium as background light that is combined with the signal light to create a second sample light pattern. The interferometer is further configured for combining the reference light with the second sample light pattern to create a second at least one interference light pattern, each having a holographic beat component. The acoustic assembly is configured for emitting the ultrasound into the second volume of non-interest in a manner that decorrelates at least a portion of the background light of the sample light pattern from the holographic beat component of each of the second interference light pattern(s). The detector(s) is configured for detecting the holographic beat component of each of the second interference light pattern(s) during the second measurement period. The processor is configured for determining an optical parameter of the second volume of interest based on detected holographic beat component of each of the second interference light pattern(s).

In this optional embodiment, the first volume of non-interest may have a first depth in the scattering medium, the second volume of non-interest may have a second depth in the scattering medium greater than the first depth. In this case, if the ultrasound is continuous wave (CW) ultrasound, the optical detection system may further comprise a controller configured for operating the acoustic assembly to vary a frequency of the ultrasound to have a first frequency, such that all of the ultrasound emitted into the scattering medium during the first measurement period is substantially confined within the first volume of non-interest, and to have a second frequency that allows all of the ultrasound emitted into the scattering medium in the second measurement period to be substantially confined within the second volume of non-interest. If the ultrasound is pulsed wave (PW) ultrasound that has a frequency that allows it to penetrate into the first volume of interest and the second volume of interest, the optical detection system may further comprise a controller configured for operating the interferometer and the acoustic assembly to pulse the sample light and the ultrasound in synchrony, such that all of the ultrasound emitted into the scattering medium during the first measurement period is substantially confined within the first volume of non-interest, and all of the ultrasound emitted into the scattering medium during the second measurement period is substantially confined within the second volume of non-interest.

In accordance with a second aspect of the present inventions, a non-invasive optical detection method comprises delivering sample light, during a measurement period, into a scattering medium having a volume of interest and a volume of non-interest. A first portion of the sample light passing through the volume of interest exits the scattering medium as signal light, and a second portion of the sample light passing through the volume of non-interest exits the scattering medium as background light that is combined with the signal light to create a sample light pattern. The method further comprises combining reference light with the sample light pattern (e.g., using a homodyne technique or a heterodyne technique) to create at least one interference light pattern (e.g., a speckle light pattern), each having a holographic beat component. The method may further comprise generating source light, and splitting the source light into the sample light and the reference light.

The interference light pattern(s) may comprise a plurality of phase-modulated interference light patterns, e.g., two phase-modulated interference light patterns having phases of 0 and $\pi$. The sample light pattern and reference light having different phases may be concurrently combined to respectively generate the phase-modulated interference light patterns. In one method, reference light and sample light have optical path lengths that match within a coherence length of the sample light, and the frequency of the sample light and the reference light are the same, such that the holographic beat component of each of the interference light pattern(s) is constant. This method may further comprise adjusting the optical path length of the reference light.

The method further comprises emitting ultrasound into the volume of non-interest that decorrelates at least a portion of the background light of the sample light pattern from the holographic beat component of each of the interference light pattern(s). In one method, the ultrasound is emitted into the volume of non-interest in that decorrelates substantially all of the background light of the sample light pattern from the holographic beat component of each of the interference light pattern(s). In another method, the ultrasound is emitted into the volume of non-interest in that decorrelates at least ninety-nine percent of the background light of the sample light pattern from the holographic beat component of each of the interference light pattern(s).

In one method, the ultrasound emitted from a single-element ultrasound transducer (e.g., a thin-film ultrasound transducer, such as, e.g., a capacitive micromachined ultrasound transducer (CMUT) or a piezo micromachined ultrasound transducers (PMUT)) into the volume of non-interest. The ultrasound may have a frequency greater than 1 MHz, e.g., in the range of 5-20 MHz, and be unfocused.

In one method, the ultrasound has a uniform frequency, a uniform amplitude, and a uniform phase during the measurement period. Another method further comprises varying at least one, and perhaps even two or more, of a frequency, an amplitude, and a phase during the measurement period. If the frequency of the ultrasound is varied during the measurement period, the frequency of the ultrasound may be swept during the measurement period or may be randomly varied during the measurement period In one method, the ultrasound is continuous wave (CW) ultrasound that has a frequency, such that all of the ultrasound emitted into the scattering medium during the measurement period is substantially confined within the volume of non-interest. In another method, the ultrasound is pulsed wave (PW) ultrasound that has a frequency that allows it to penetrate into the volume of interest. In this case, the optical detection system may further comprise a controller configured for operating the interferometer and the acoustic assembly to pulse the sample light and the ultrasound in synchrony during the measurement period, such that all of the ultrasound emitted into the scattering medium during the measurement period is substantially confined within the volume of non-interest.

The method further comprises detecting the holographic beat component of each of the interference light pattern(s) during the measurement period. Each of the interference light pattern(s) may comprise spatial components, in which case, detecting the interference light pattern(s) may comprise detecting intensities of the spatial components of the interference light pattern(s).

The method further comprises determining an optical parameter of the volume of interest based on detected holographic beat component of each of the interference light pattern(s). In one method, the scattering medium is an anatomical structure, in which case, the volume of interest may comprise a target tissue voxel within the anatomical structure, and the optical parameter may be a physiologically-dependent optical parameter of the target tissue voxel, e.g., a level of deoxygenated and/or oxygenated hemoglobin concentration or relative abundance. If the target tissue voxel comprises grey matter of a brain matter, the volume of non-interest may comprise a scalp and skull, and the processor may be further configured for determining neural activity within the target tissue voxel based on the determined physiologically-dependent optical parameter. In this case, the physiologically-dependent optical parameter may be a fast-optical signal.

In an optional method, the volume of interest is a first volume of interest, the volume of non-interest is a first volume of non-interest, the measurement period is a first measurement period, the sample light is a first sample light, and the interference light pattern(s) is a first interference light pattern(s). In this case, the optical detection method further comprises delivering the sample light into the scattering medium having a second volume of interest and a second volume of non-interest during a second measurement period. A first portion of the second sample light passing through the second volume of interest exits the scattering medium as signal light, and a second portion of the second sample light passing through the second volume of non-interest exits the scattering medium as background light that is combined with the signal light to create a second sample light pattern. This method further comprises combining the reference light with the second sample light pattern to create a second at least one interference light pattern, each having a holographic beat component. The method further comprises emitting the ultrasound into the second volume of non-interest in a manner that decorrelates the background light of the sample light pattern from the holographic beat component of each of the second interference light pattern(s), detecting the holographic beat component of each of the second interference light pattern(s) during the second measurement period, and determining an optical parameter of the second volume of interest based on detected holographic beat component of each of the second interference light pattern(s).

In this optional method, the first volume of non-interest may have a first depth in the scattering medium, the second volume of non-interest may have a second depth in the scattering medium greater than the first depth. If the ultrasound is continuous wave (CW) ultrasound, the method may further comprise varying a frequency of the ultrasound to have a first frequency, such that all of the ultrasound emitted into the scattering medium during the first measurement period is substantially confined within the first volume of non-interest, and to have a second frequency that allows all of the ultrasound emitted into the scattering medium in the second measurement period to be substantially confined within the second volume of non-interest. If the ultrasound is pulsed wave (PW) ultrasound that has a frequency that allows it to penetrate into the first volume of interest and the second volume of interest, the method may further comprise pulsing the sample light and the ultrasound in synchrony, such that all of the ultrasound emitted into the scattering medium during the first measurement period is substantially confined within the first volume of non-interest, and all of the ultrasound emitted into the scattering medium during the second measurement period is substantially confined within the second volume of non-interest.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 10b is a top view of the ultrasound transducer of FIG. 10a;

FIG. 11b is a top view of the ultrasound transducer of FIG. 11a;

FIG. 14 is a diagram illustrating an exemplary relationship between the delivery of pulses of sample light and the frame rate of the optical detection system of FIG. 6;

FIGS. 18a-18c are diagrams illustrating yet another exemplary technique used by the optical detection system of FIG. 6 to confine an optical masking zone created by CW ultrasound with multiple volumes of non-interest;

DETAILED DESCRIPTION OF THE EMBODIMENTS

Figure 1:
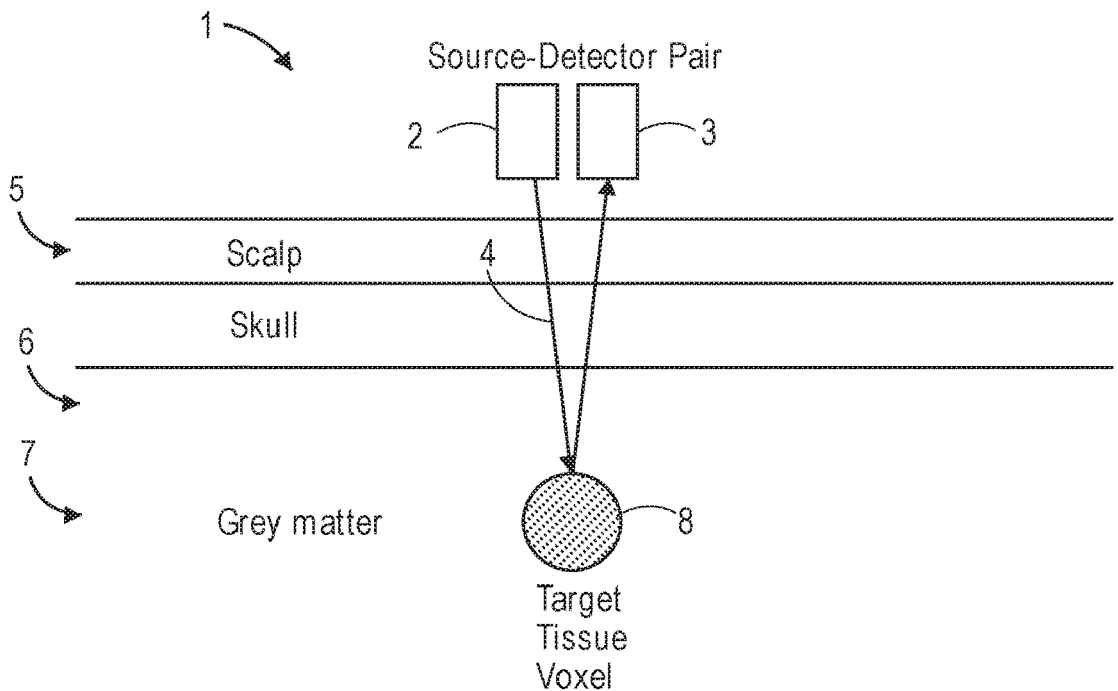
FIG. 1 is a diagram of a prior art optical coherent tomography (OCT) system for detecting an optical parameter in a target tissue voxel of a brain.
Figure 2:
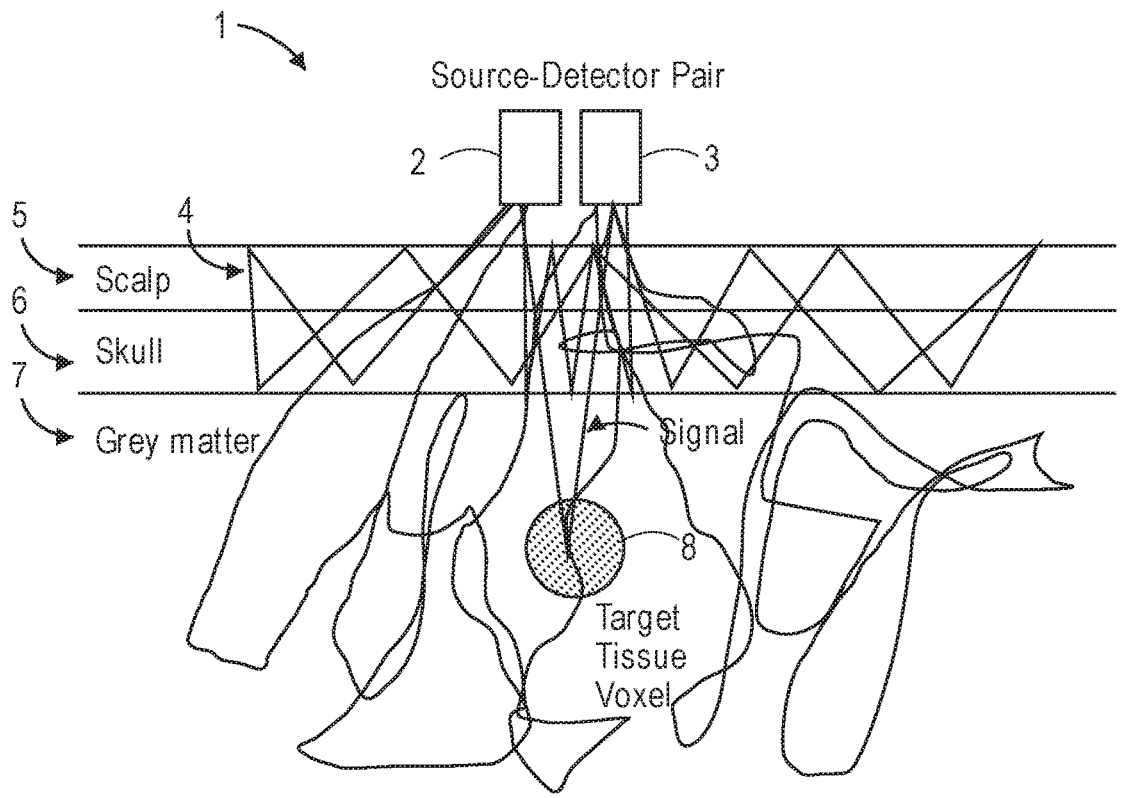
FIG. 2 is a diagram illustrating the various optical paths taken by sample light emitted and detected by the prior art OCT system of FIG. 1 prior to path-length selection.
Figure 3:
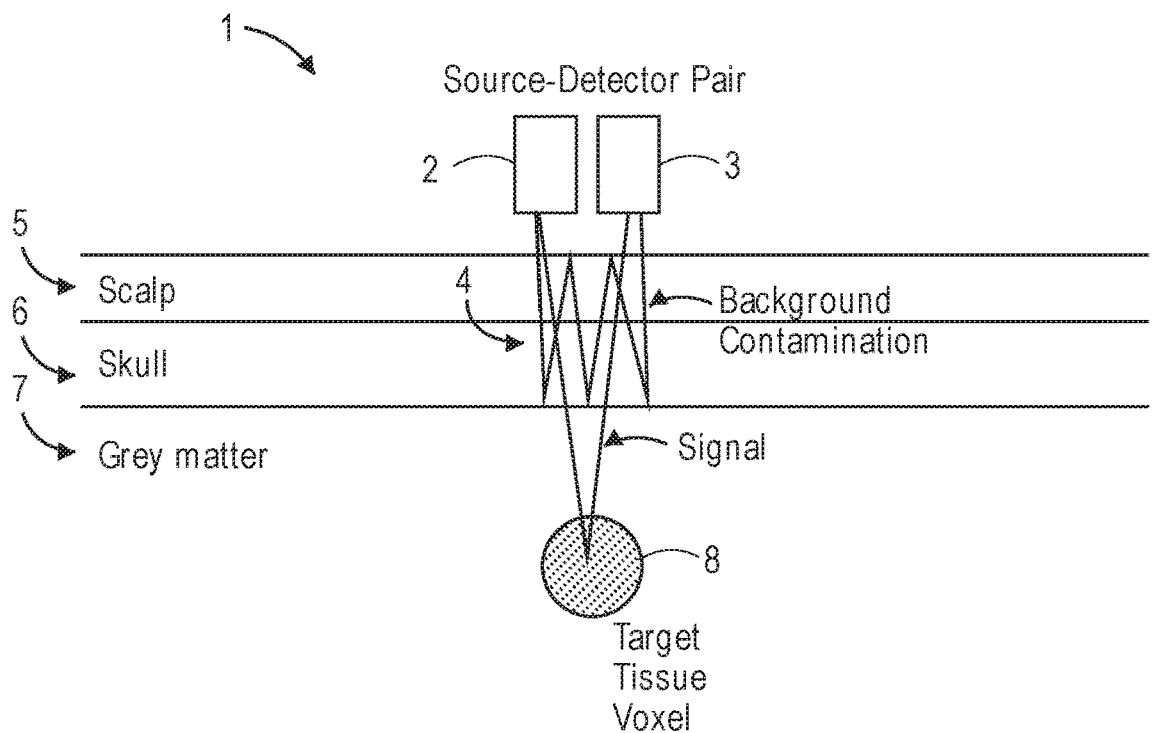
FIG. 3 is a diagram illustrating the optical paths taken by the sample light after being emitted and detected by the prior art OCT system of FIG. 2 after path-length selection.
Figure 4:
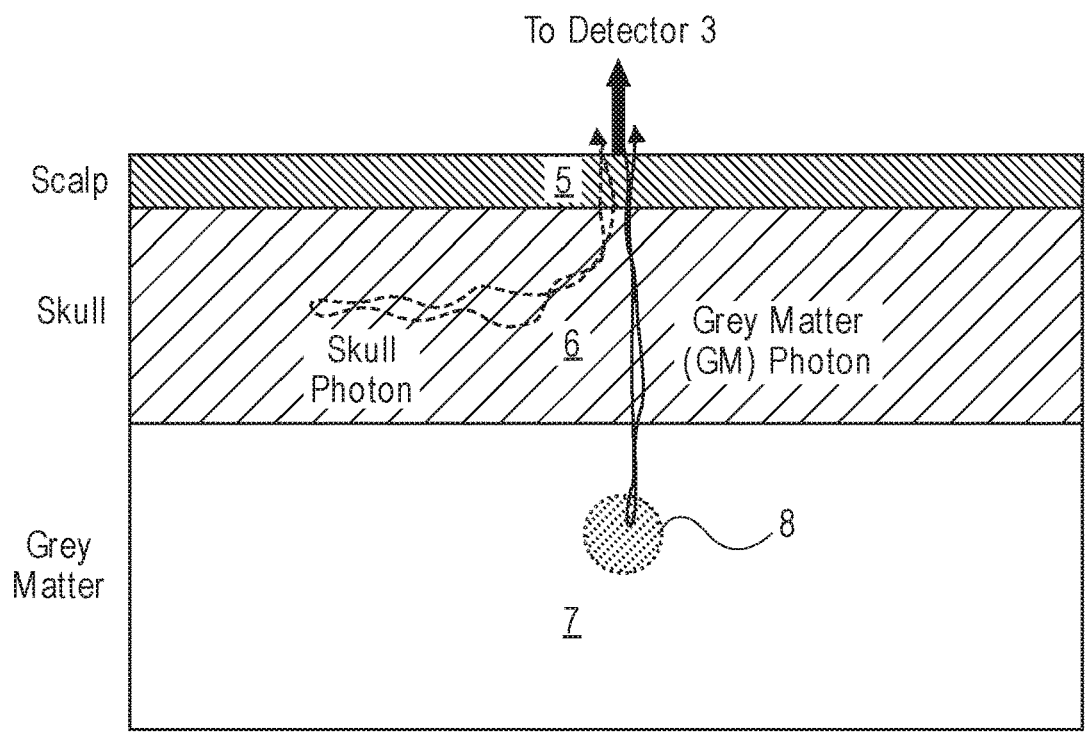
FIG. 4 is a diagram illustrating the matching optical paths taken by a skull photon and a grey matter (GM) photon detected by the detector of the prior art OCT system of FIG. 1.
Figure 5:
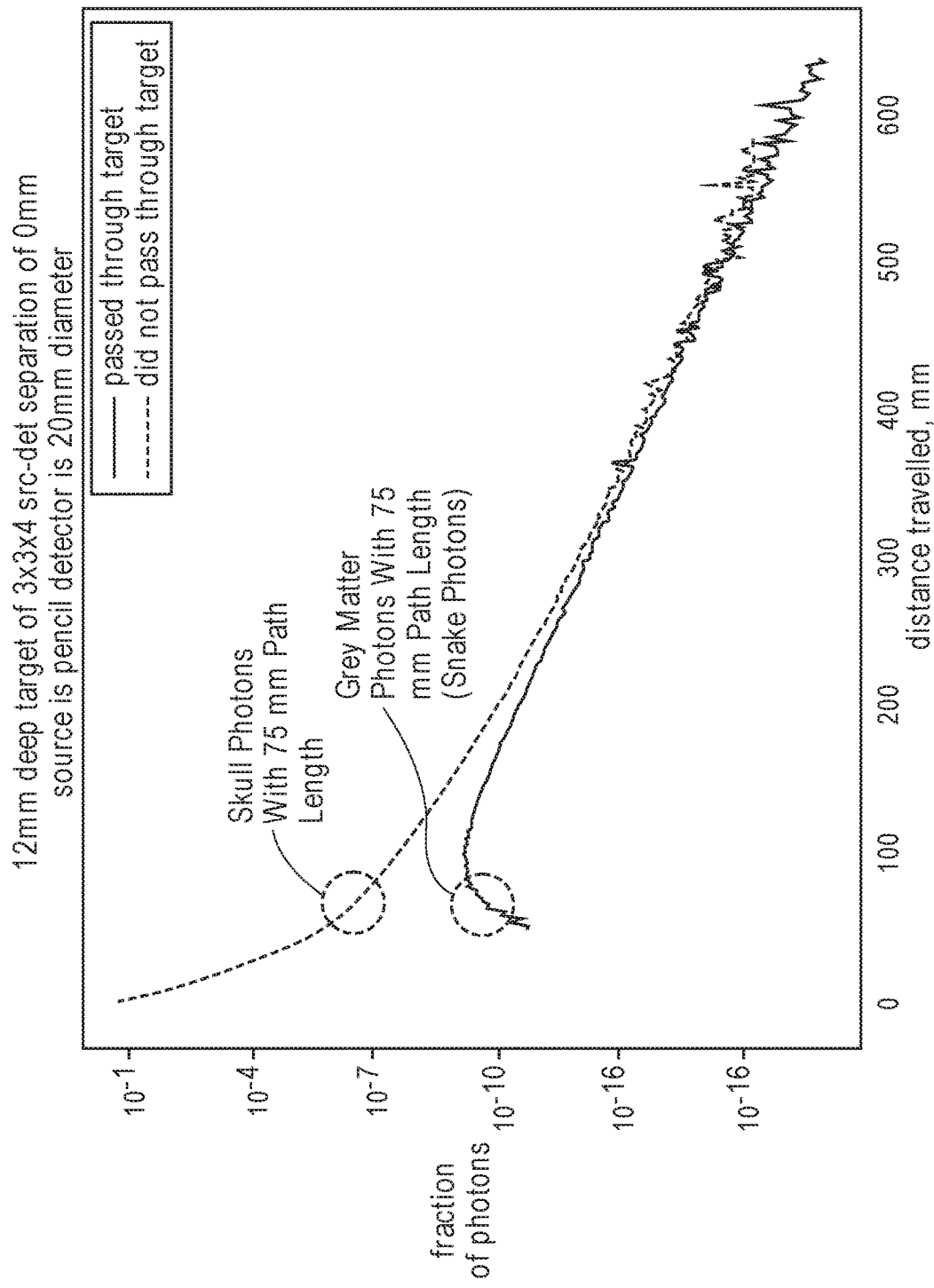
FIG. 5 is a plot illustrating the fraction of photons that pass through a target tissue voxel in the brain versus the fraction of photons that do not pass through the target tissue voxel in the brain, plotted against optical path length.
Figure 6:
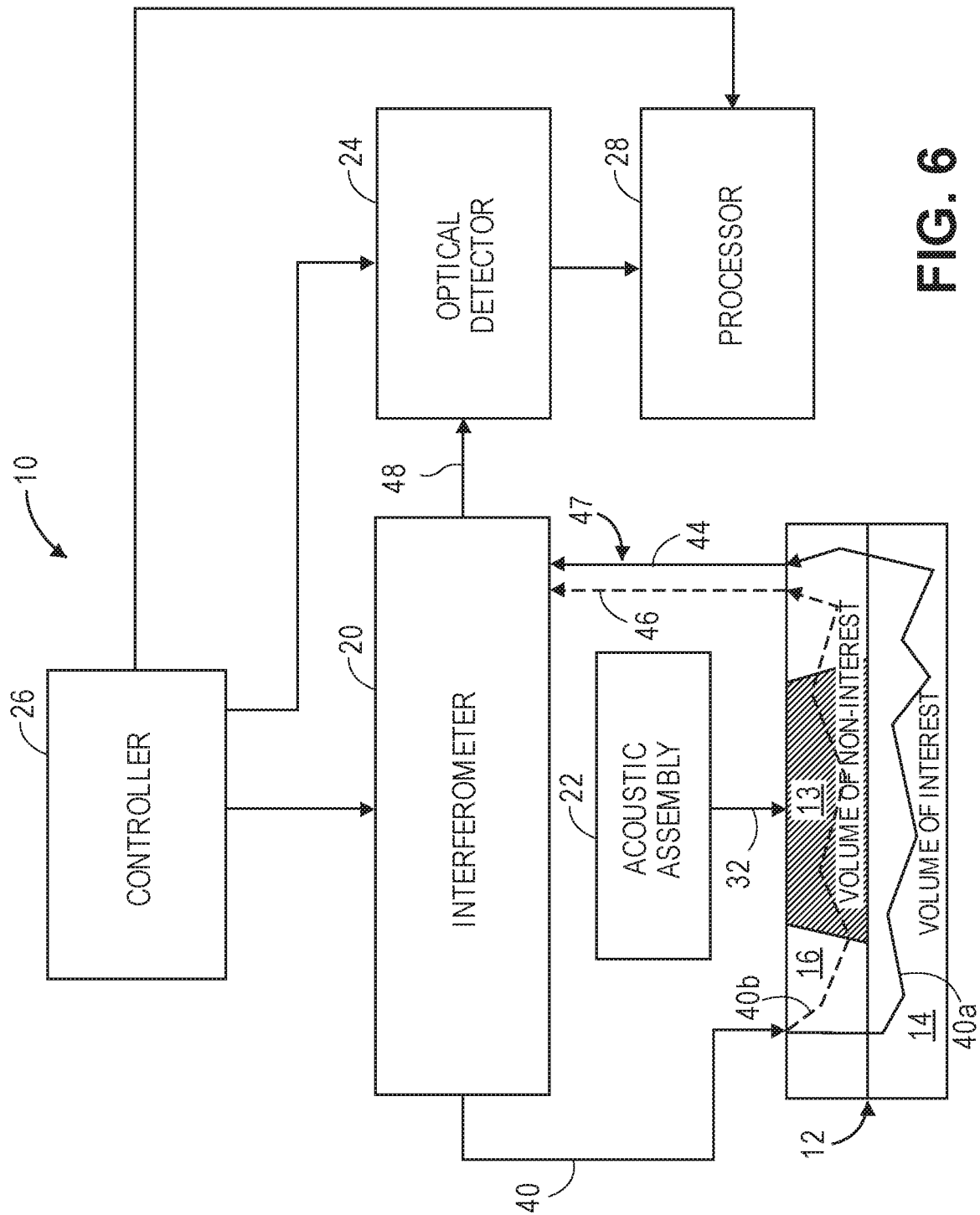
FIG. 6 is a block diagram of a non-invasive optical detection system constructed in accordance with one embodiment of the present inventions.

Referring to FIG. 6, a non-invasive optical detection system 10 constructed in accordance with one embodiment of the present inventions is designed to detect an optical parameter of a first volume of interest 14 in a scattering medium 12 (examples of volume of interest and different types of scattering mediums are defined below). Significantly, the optical detection system 10 uses ultrasound 32 to create an "optical masking zone" 13 in a second volume of non-interest 16 that masks out photons passing through the second volume of non-interest 16 from contributing to the detected optical parameter of the first volume of interest 14, thereby minimizing or at least lessening background noise, and as a result, maximizing or at least increasing the signal-to-noise ratio of the detected optical parameter of the first volume of interest 14 while also increasing the spatial resolution. The fundamental principle is that light that intersects the optical masking zone 13 is rejected due to its interaction with the ultrasound 32 in the masking zone 13, while light that does not intersect the optical masking zone 13 is accepted for subsequent detection, as described in further detail below. Throughout the specification, the "first volume of interest 14" within the scattering medium 12 will also be referred to as "volume of interest 14"; and the "second volume of non-interest 16" within the scattering medium 12 will be referred to as "volume of non-interest 16."

Although the optical detection system 10 can be used for any application where it is desirable to detect an optical parameter in a volume of interest 14 of a scattering medium 12, as will be described in further detail below, the optical detection system 10 particularly lends itself well to anatomical detection applications, and in particular, the detection or imaging of anatomical parts of a human body, an animal body, and/or biological tissue. In this case, the scattering medium 12 may be an anatomical structure, such as, the intact head of a person, including the scalp, skull, and brain, with the volume of interest 14 being the brain, and the volume of non-interest 16 being the scalp and skull. When used to detect neural activity within a head, the optical detection system 10 essentially renders the skull optically transparent by combining the optical masking zone 13 to the scalp and skull to mask out the photons that do not penetrate through the skull into the brain, but instead wander around in the scalp and skull.

Thus, as will be described in further detail below, the optical detection system 10 may take the form of an anatomical detection system, in which case, the detected optical parameter may be a physiologically-dependent optical parameter. As will be described herein, the optical detection system 10 can be used as an optical coherence tomography (OCT) system, although the optical detection system 10 can be used in other systems, such as an ultrasound modulated optical tomography (UOT) system, e.g., as described in U.S. patent application Ser. No. 15/844,370, entitled "Pulsed Ultrasound Modulated Optical Tomography Using Lock-In Camera," which is expressly incorporated herein by reference; a holography system, e.g., as described in U.S. U.S. patent application Ser. No. 16/299,067, entitled "Non-Invasive Optical Detection Systems and Methods in Highly Scattering Medium," which is expressly incorporated herein by reference; and off-axis holography systems, etc.

Information and acquired neural data related to the detected physiologically-dependent optical parameter may be used (e.g., computed, processed, stored, etc.) internally within the anatomical detection system to adjust the detection parameters of the detection system, such as increasing or decreasing the strength of the optical source and/or data compression and/ or analysis, such a Fast Fourier Transform (FFT) and/or statistical analysis; or may be transmitted to external programmable devices for use therein, e.g., medical devices, entertainment devices, neuromodulation stimulation devices, lie detection devices, alarm systems, educational games, brain interface devices, etc.

In a practical implementation, the optical detection system 10 will acquire data from multiple target voxels ("data voxels") spatially separated from each other within the volume of interest 14, as will be described in further detail below. A "voxel" may be defined as a contiguous sub-volume of space that is targeted for imaging or detecting within the scattering medium 12. For purposes of brevity, the optical detection system 10 is primarily described herein as acquiring one data voxel (i.e., data representative of an optical parameter of the data voxel), e.g., by using a single paired source-detector arrangement, although it should be understood that the optical detection system 10 may be capable of acquiring more than one data voxel from the volume of interest 14 of the scattering medium 12, e.g., by using a multiple paired source-detector arrangement or by moving the single paired source-detector arrangement between the acquisition of data voxels, or by having multiple detectors for a single source, as will be described in further detail with respect to FIGS. 27 and 28.

Returning to FIG. 6, the optical detection system 10 generally includes an interferometer 20, an acoustic assembly 22, a detector 24, a controller 26, and a processor 28, which uniquely interact with each other to detect the optical parameter of the volume of interest 14 while masking out the undesirable photons passing through the volume of non-interest 16 from the detected optical parameter of the volume of interest 14.

The interferometer 20 is, for example a Mach-Zehnder type interferometer, comprising a sample arm that passes through the scattering medium 12 and a reference arm (described in further detail below with respect to FIG. 7) that operate together to create an interference light pattern 48. In the illustrated embodiment, the interference light pattern 48 takes the form of a speckle light pattern, which can be defined as an intensity pattern produced by the mutual interference of a set of scattered wavefronts. That is, a speckle light pattern results from the interference of many waves, but having different phases and amplitudes, which add together to give a resultant wave whose amplitude, and therefore intensity and phase, varies randomly.

The interferometer 20 is configured for delivering sample light 40 into the scattering medium 12 along the sample arm during a measurement period. As the sample light 40 scatters diffusively through the scattering medium 12, various portions of the sample light 40 will take different paths through the scattering medium 12. For purposes of brevity, only a first sample light portion 40a traveling along one optical path through the volume of interest 14, and a second sample light portion 40b traveling along another optical path exclusively through the volume of non-interest 16 are illustrated, although it should be appreciated that the diffused sample light 40 will travel along many more paths through the scattering medium 12. The first sample light portion 40a passing through the volume of interest 14 will exit the scattering medium 12 as signal light 44, and the second sample light portion 40b passing through the volume of non-interest 16 will exit the scattering medium 12 as background light 46. The signal light 44 and background light 46 combine to create a sample light pattern 47, which is encoded with optical parameters of the volume of interest 14 by the signal light 44 for detection by the optical detector 24, as will be described in further detail below.

It should be appreciated that, although not all of the sample light pattern 47 exiting the scattering medium 12 will be detected, it is only important that enough of the sample light pattern 47 be detected, such that the optical parameters encoded in the signal light 44 within the sample light pattern 47 can be extracted. It should also be appreciated that, as illustrated in FIG. 6, because the depth of the volume of interest 14 is greater than the depth of the volume of non-interest 16 within the scattering medium 12 in this particular example, as a practical matter, some of the scattered sample light 40 may pass through both the volume of interest 14 and the volume of non-interest 16 to create the signal light 44, in which case, it is desirable that such scattered sample light 40 be treated as the first sample light portion 40a that exits the volume of interest 14 as signal light 44. That is, once the sample light 40 passes into the volume of interest 14 from the volume of non-interest 16, it is desirable that the light that exits the scattering medium from such sample light 40 be treated as signal light 44. Thus, only the sample light 40 that is exclusively confined to the volume of non-interest 16, without ever passing into or out of the volume of interest 14, will be treated as background light 46. As will be described in further detail below, in such a case, the ultrasound 32 is delivered into the scattering medium 12, such that one or more optical ports 17 (shown in FIGS. 10a-10b and 11a-11b) are created within the volume of non-interest 16 adjacent the optical masking zone 13 to allow both ingress and egress of the first sample light portion 40a to and from the volume of interest 12 without being undesirably masked by the optical masking zone 13 from the detected optical parameter within the volume of interest 14.

The interferometer 20 combines the sample light pattern 47 with reference light 42 (shown in FIG. 7) to create the interference light pattern 48, which has a holographic beat component that can be detected by the optical detector 24 as the signal component during the measurement period, as will be discussed in further detail below with respect to FIGS. 20-24.

The interferometer 20 amplifies the signal light 44 in the sample light pattern 47 by combining the signal light 44 and the reference light 42 using, depending on the particular implementation, a homodyne technique or a heterodyne technique. For the purposes of this specification, the term "homodyne," when referring to the combination of signal light 44 and reference light 42, means that the signal light 44 and reference light 42 have the same frequency when combined to generate interference terms having DC holographic beat components, as opposed to the term "heterodyne," which means that the signal light 44 and reference light 42 have different frequencies when combined to generate interference terms with AC holographic beat components. Thus, if the signal light 44 and reference light 42 have the same frequency (i.e., they are combined using a homodyne technique), the holographic beat component of the interference light pattern 48 will be constant. In contrast, if the signal light 44 and reference light 42 having different frequencies (i.e., they are combined using a heterodyne technique), the holographic beat component of the interference light pattern 48 will have a frequency equal to the difference between the frequencies of the signal light 44 and reference light 42.

Figure 23:
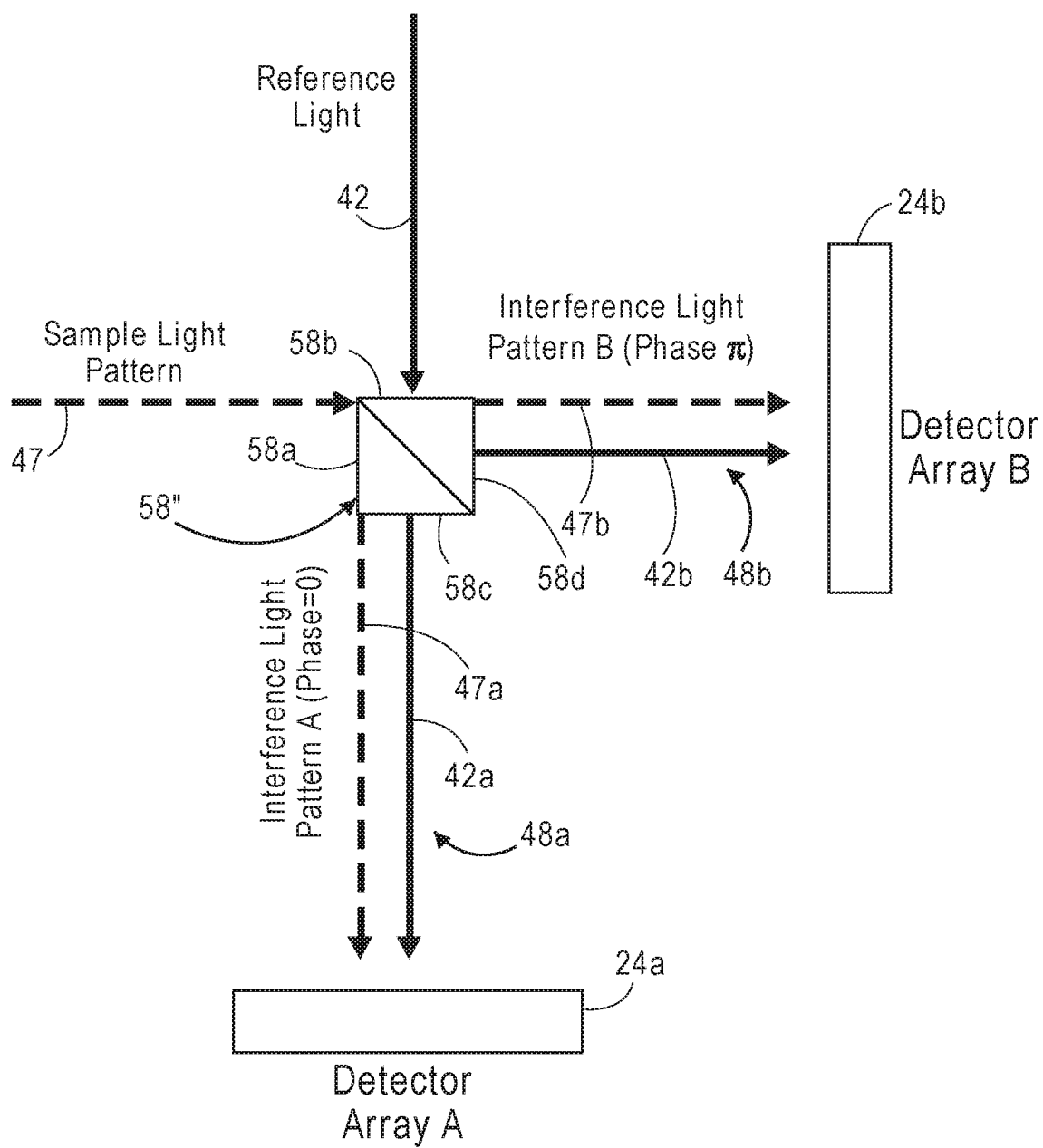
FIG. 23 is a block diagram of another specific embodiment of an optical beam combiner of an interferometer and detector array that can be used in the optical detection system of FIG. 6.
Figure 24:
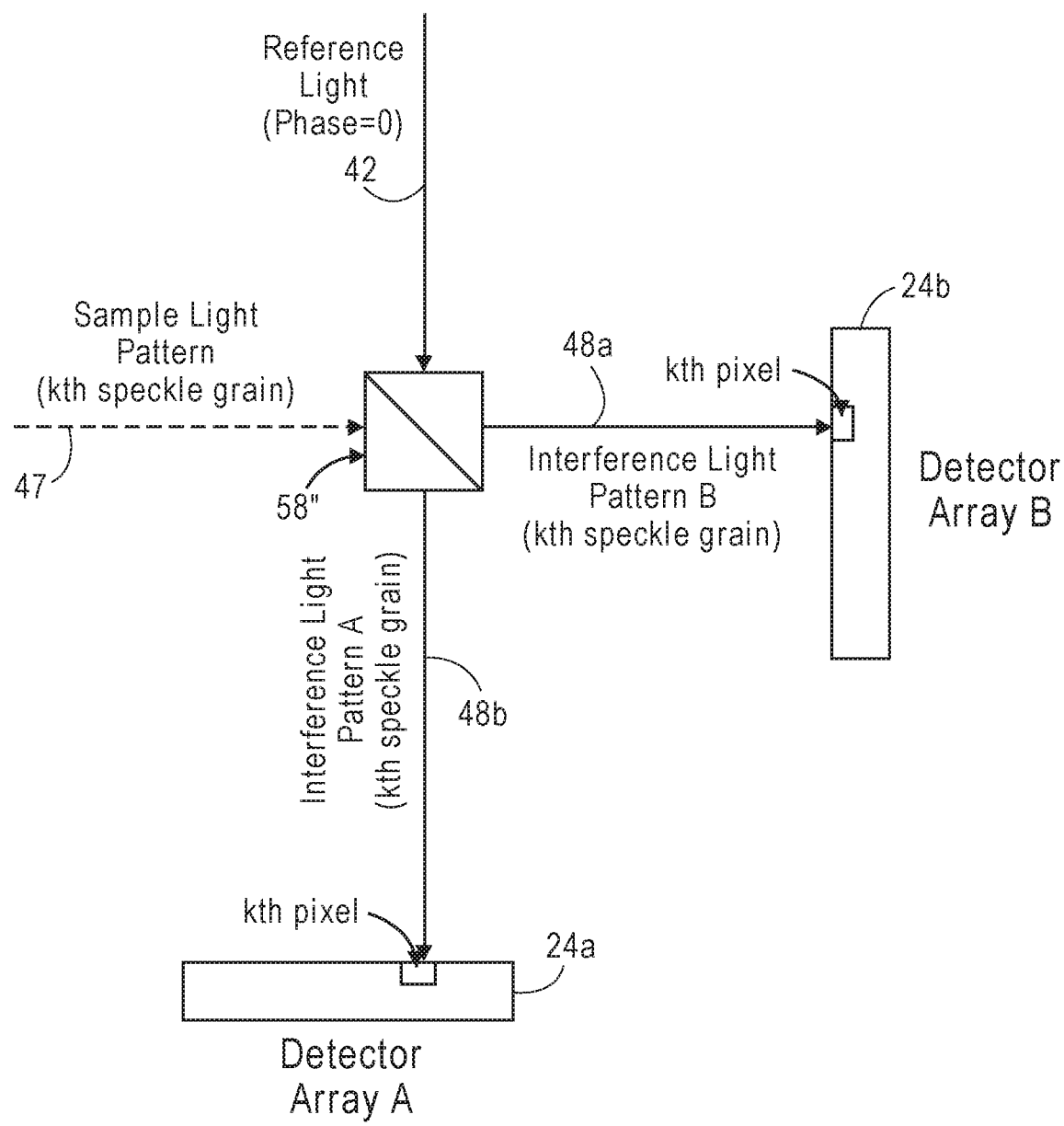
FIG. 24 is a block diagram of the optical beam combiner of an interferometer and detector array of FIG. 23, particularly showing the generation and detection of a kth speckle grain of an interference light pattern.

It should be noted that although the interferometer 20, for purposes of brevity, is described in FIG. 6 as only creating one interference light pattern 48 from the sample light pattern 47 and reference light 42 for each measurement period, and further describes the optical detection system 10 as only having one detector 24 for detecting such interference light pattern 48, the interferometer 20 may create multiple interference light patterns 48 (typically phase-modulated) from the sample light pattern 47 and reference light 42 for each measurement period, in which case, the optical detection system 10 may have an equal number of detectors 24 for detecting such interference light patterns 48, as will be described in further detail below with respect to FIGS. 23 and 24.

Figure 7:
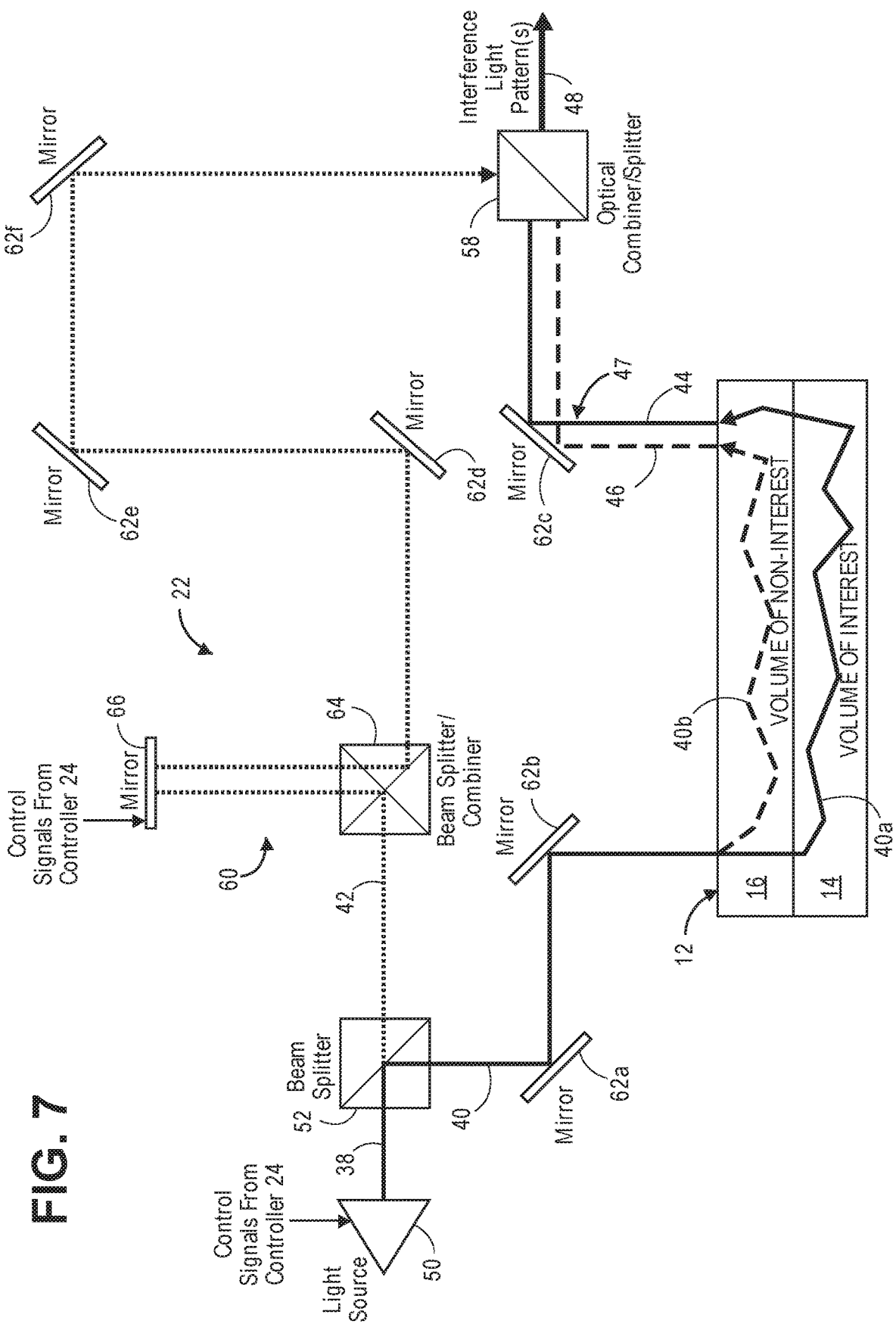
FIG. 7 is a block diagram of one embodiment of an interferometer used in the optical detection system of FIG. 6.

With reference now to FIG. 7, one embodiment of an interferometer 20 that can be used in the optical detection system 10 of FIG. 6 will now be described. The interferometer 20 includes an optical source 50, an optical beam splitter 52, an optical beam splitter/combiner 58, a path length adjustment mechanism 60, and a mirror arrangement 62 (which comprises, e.g., mirrors 62a, 62b, 62c, 62d, 62e, and 62f). Depending on the specific implementation of the detecting techniques of the optical detection system 10, the interferometer 20 may comprise an optical frequency shifter (not shown) for shifting the frequency of the sample light 40 and reference light 42 relative to each other, as further described in U.S. patent application Ser. No. 15/844,370, entitled "Pulsed Ultrasound Modulated Optical Tomography Using Lock-In Camera," and U.S. patent application Ser. No. 16/299,067, entitled "Non-Invasive Optical Detection Systems and Methods in Highly Scattering Medium," which are both expressly incorporated herein by reference.

The optical source 50 is configured for generating source light 38, and may take the form of, e.g., a super luminescent diode (SLD), a light emitting diode (LED), a Ti:Saph laser, a white light lamp, a diode-pumped solid-state (DPSS) laser, a laser diode (LD), a super luminescent light emitting diode (sLED), a titanium sapphire laser, and/or a micro light emitting diode (mLED), or a distributed feedback (DFB) laser or similar laser to achieve very narrow linewidths and extremely high amplitude stability, among other optical sources.

The wavelength of light generated by the optical source 50 may be, e.g., in the range of 350 nm-1500 nm, and/or may be ultraviolet (UV) light, visible light, and/or near-infrared and infrared light. The optical source 50 may generate monochromatic light comprising a single-wavelength light, or light having multiple wavelengths (e.g., white light). In some variations, the optical source 50 can emit a broad optical spectrum or emit a narrow optical spectrum that is then rapidly swept (e.g., changed over time) to functionally mimic or create an effective broad optical spectrum. In alternative embodiments, multiple optical sources may be used to generate the source light 38 at multiple distinct wavelengths, e.g., one generating source light 38 within the range of 605 nm to 800 nm, and another generating source light 38 within the range of 800 nm to 1300 nm.

The optical source 50 may be a continuous wave (CW) or a pulsed wave (PW) optical source with either a predefined coherence length or a variable coherence length Preferably, the optical source 50 is a high-coherence optical source (i.e., a laser), although in alternative embodiments, the optical source 50 may be a low-coherence light source. If the optical detection system 10 utilizes OCT techniques, as will be described in further detail below, the optical source 50 may be configured for generating source light 38 having a coherence length selected to correspond to the desired level of path-length selectivity, e.g., from about 75 μm to about 200 μm, e.g., about 100 μm for detecting optical properties at depths of 6-10 mm below the surface of scattering medium 12, and in the case illustrated below, the scalp, through the skull, and into the brain.

The optical source 50 may receive power from a drive circuit (not shown). The optical source 50, itself, may include control inputs, or a separate optical acoustic modulator (not shown) may include control inputs, for receiving control signals from the controller 26 that cause the optical source 50 to emit the source light 38 at a selected time, duration, and intensity, and if variable, a coherence length. Thus, the controller 26 (shown in FIG. 6) may selectively pulse the source light 38, and thus the sample light 40 and reference light 42. It should be noted that, because the optical detection system 10 does not rely solely on heterodyne suppression of the background light 46 (as, e.g., compared to UOT), the interferometer 20 is highly tolerant to instability in the optical source 50 and waveform shape within the measurement period.

The optical beam splitter 52 is configured for splitting the source light 38 into the sample light 40 that propagates along a sample arm of the interferometer 20 and the reference light 42 that propagates along a reference arm of the interferometer 20. In the illustrated embodiment, the optical beam splitter 52 (e.g., a partially transparent mirror) splits the source light 38 via amplitude division by reflecting a portion of the source light 38 as the sample light 40, and transmitting the remaining portion of the source light 38 as the reference light 42, although the optical beam splitter 52 may alternatively reflect a portion of the source light 38 as the reference light 42, and transmit the remaining portion of the source light 38 as the sample light 40. In alternative embodiments, the optical beam splitter 52 may split the source light 38 via wavefront division by splitting a portion of the wavefront into the sample light 40 and splitting the remaining portion of the wavefront into the reference light 42. In either case, the optical beam splitter 52 may not necessarily split the source light 38 equally into the sample light 40 and reference light 42, and it may actually be more beneficial for the optical beam splitter 52 to split the source light 38 unevenly, such that the amplitude of the sample light 40 is less than the amplitude of the reference light 42 (e.g., 10/90 power ratio) in order to comply with tissue safety standards. That is, the amplitude of the sample light 40 will preferably be relatively low to avoid damaging the tissue, whereas the amplitude of the reference light 42, which will be used to boost the sample light pattern 47 in the interference light pattern 48, will be relatively high.

The optical beam splitter/combiner 58 is configured for combining the reference light 42 with the sample light pattern 47 via superposition to generate the interference light pattern(s) 48. The optical beam splitter/combiner 58 can take the form of, e.g., a combiner/splitter mirror. Variations of the optical beam splitter/combiner 58 will be described in further detail below with respect to FIGS. 21-24.

The path length adjustment mechanism 60 is configured for adjusting the optical path length of the reference arm to nominally match the expected optical path length of the sample arm. The path length adjustment mechanism 60 may include control inputs for receiving control signals from the controller 26 to cause the path length adjustment mechanism 60 to adjust the optical path length of the reference arm. The path length adjustment mechanism 60 includes an optical beam splitter/combiner 64 and an adjustable mirror 66 that can be displaced relative to the optical beam splitter/combiner 64. The beam/splitter combiner 64 is configured for redirecting the reference light 42 at a ninety-degree angle towards the mirror 66, and redirecting the reference light 42 reflected back from the mirror 66 at a ninety-degree angle towards the optical beam splitter/combiner 58. Thus, adjusting the distance between the mirror 66 and the optical beam splitter/combiner 64 will adjust the optical path length of the reference arm to match the optical path length of the sample arm.

Figure 8:
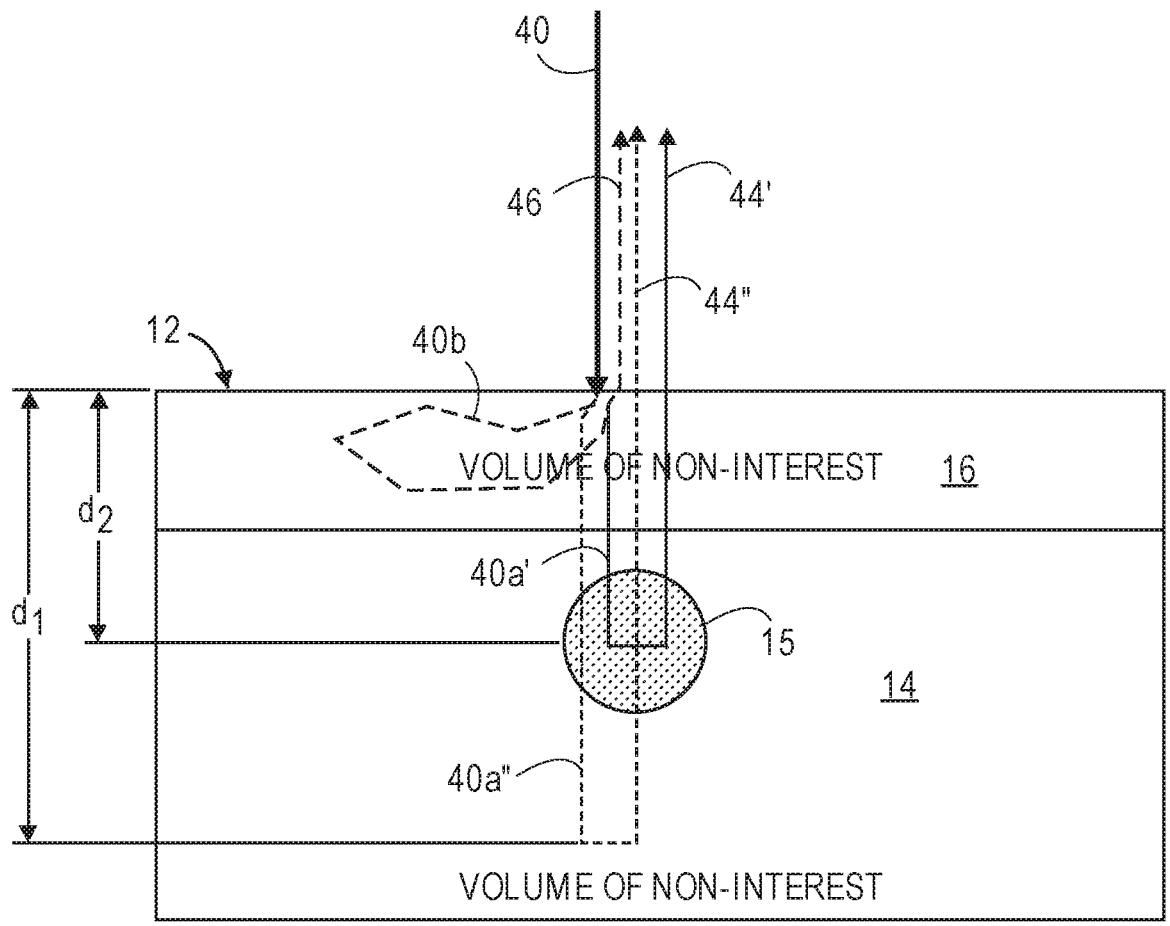
FIG. 8 is diagram illustrating an exemplary path-length selection technique employed by the optical detection system of FIG. 6.

Referring further to FIG. 8, in the case where the optical detection system 10 takes the form of an OCT system, the path length adjustment mechanism 60 may be adjusted to select the path length of the sample light 40 for detection of optical parameters within a tissue voxel 15 within the volume of interest 14 of the scattering medium 12, as illustrated in FIG. 8. In particular, the system 10 uses path-length selection to distinguish between a first sample light portion 40*a'* and a second sample light portion 40*a"*, the first sample light portion 40*a* having a first optical path length being backscattered by the tissue voxel 15 as signal light 44', and thus encoded with the optical parameters of the tissue voxel 15, and the second sample light portion 40*b'* having a second optical path length different from the first optical path length and being backscattered by a region of the volume of interest 14 not coincident with the tissue voxel 15, and thus not encoded with the optical parameters of the target tissue voxel 15. As shown, because the tissue voxel 15 has a fixed depth $d_2$ compared to tissue at different other depths (e.g., depth $d_1$), the tissue voxel 15 may be selectively targeted for detecting by the optical detection system 10.

That is, the path length adjustment mechanism 60 is adjusted, such that the optical path length of the first sample light portion 40*a'* (in contrast to the optical path length of the second sample light portion 40*a"*) matches the optical path length of the reference light 42 within the optical coherence length of the sample light 40, such that only the signal light 44' resulting from the first sample light portion 40*a'* that is backscattered by the tissue voxel 15 contributes to the timing-varying interference component of the interference light pattern 48. Thus, depending on the location of the particular target tissue voxel 15, the path length adjustment mechanism 60 can be adjusted to target that target tissue voxel 15. For example, if a different target tissue voxel (not shown) at a depth $d_1$ is desired to be detected, the path length adjustment mechanism 60 can be adjusted, such that the optical path length of the second sample light portion 40*a"* (in contrast to the optical path length of the first sample light portion 40*a'*) matches the optical path length of the reference light 42 within the optical coherence length of the sample light 40, such that only the signal light 44" resulting from the second sample light portion 40*a"* that is backscattered by the different tissue voxel contributes to the timing-varying interference component of the interference light pattern 48. Further details describing OCT systems are set forth in U.S. patent application Ser. No. 15/853,538, entitled "Systems and Methods for Quasi-Ballistic Photon Optical Coherence Tomography in Diffusive Scattering Media Using a Lock-In Camera Detection" (now U.S. Pat. No. 10,219,700), which is expressly incorporated herein by reference.

Referring back to FIG. 7, the mirror assembly 62 is configured for confining the optical light paths in the interferometer 20 into a small form factor. In the illustrated embodiment, the mirror assembly 62 includes a first tilted, completely reflective, mirrors 62*a*, 62*b* configured for redirecting the sample light 40 from the optical beam splitter 52 towards the scattering medium 12; a tilted completely reflective, mirror 62*c* configured for redirecting the resulting sample light pattern 47 exiting the scattering medium 12 towards one face of the optical beam splitter/combiner 58, and three tilted, completely reflective, mirrors 62*d*-62*f* configured for redirecting the reference light 42 from the optical beam splitter/combiner 64 towards another face of the optical beam splitter/combiner 58. In an alternative embodiment, rather than using mirrors in the reference arm, a fiber optical waveguide can be used between the optical beam splitter/combiner 64 and the optical beam combiner 58, e.g., to more easily satisfy the form factor requirements of a wearable device.

Referring back to FIG. 6, the acoustic assembly 22 is configured for emitting ultrasound 32 into the volume of non-interest 16. Preferably, the frequency of the ultrasound 32 is selected (e.g., in the range of 100 KHz-20 MHz), such that the ultrasound 32 can pass efficiently through the volume of non-interest 16, thereby masking photons propagating through the volume of non-interest 16 from contributing to the detected optical parameter of the volume of interest 14; although as will be described in further detail with respect to FIG. 9, it is preferable that the frequency of the ultrasound 32 be greater than 1 MHz. In the illustrated embodiment, such masking of photons is accomplished by decorrelating at least a portion of the background light 46 in the sample light pattern 47 from the holographic beat component of the interference light pattern 48. For the purposes of this specification, background light 46 is decorrelated from the holographic beat component of the interference light pattern 48 if it is prevented contributing to the holographic beat component of interference light pattern 48. In the illustrated embodiment, the background light 46 is decorrelated from the holographic beat component of the interference light pattern 48 by scrambling the background light 46, such that the background light 46 will have a continuously randomized phase in comparison to the reference light 42, and thus, cannot be holographically amplified by the reference light 42 to create a coherent signal, as discussed in further detail below. As such, the background light 46 will not significantly contribute to the holographic beat component of the interference light pattern 48, as will be discussed in further detail below.

Although the ultrasound 32 will decorrelate at least a portion of the background light 46 of the sample light pattern 47 from the holographic beat component of interference light pattern 48, it is preferred that the ultrasound 32 be delivered into the volume of non-interest 16, such that substantially all of the background light 46 of the sample light pattern 47 be decorrelated from the holographic beat component of interference light pattern 48 (for the purposes of this specification, defined as at least 90 percent of background light 46 in the sample light pattern 47 being decorrelated, determined at the beginning of the pulse of sample light 40), and more preferably, such that at least 99 percent of the background light 46 of the sample light pattern 47 be decorrelated from the holographic beat component of interference light pattern 48, determined at the beginning of the pulse of sample light 40. At the same time, it is also preferable that the ultrasound 32 not decorrelate the signal light 46 of sample light pattern 47 from the holographic beat component of the interference light pattern 48, determined at the beginning of the pulse of sample light 40.

Thus, it is important that, during the beginning of the measurement period, the optical masking zone 13 extend through the entire thickness of the volume of non-interest 16 without extending into the volume of interest 14. Put another way, during the delivery of the sample light 40 into the scattering medium 12, it is preferred that all of the ultrasound 32 emitted by the ultrasound transducer 34 (whether CW or PW) into the scattering medium 12 be substantially confined within the volume of non-interest 16 (defined as at least 90 percent of the all of the ultrasound 32 emitted by the ultrasound transducer 34 confined within the volume of non-interest 16) at the beginning of the measurement period, and in this case, during the delivery of the sample light 40 into the scattering medium 12. More preferably, at least 99 percent of all of the ultrasound 32 emitted by the ultrasound transducer 34 into the scattering medium 12 be confined within the volume of non-interest 16 at the beginning of the measurement period. It is also preferred that the ultrasound 32 (and thus the optical masking zone 13) span the entire width of the volume of non-interest 16 at the beginning of the measurement period to ensure that all of the background light 46 is decorrelated from the holographic beat component of the interference light pattern 48.

Figure 9:
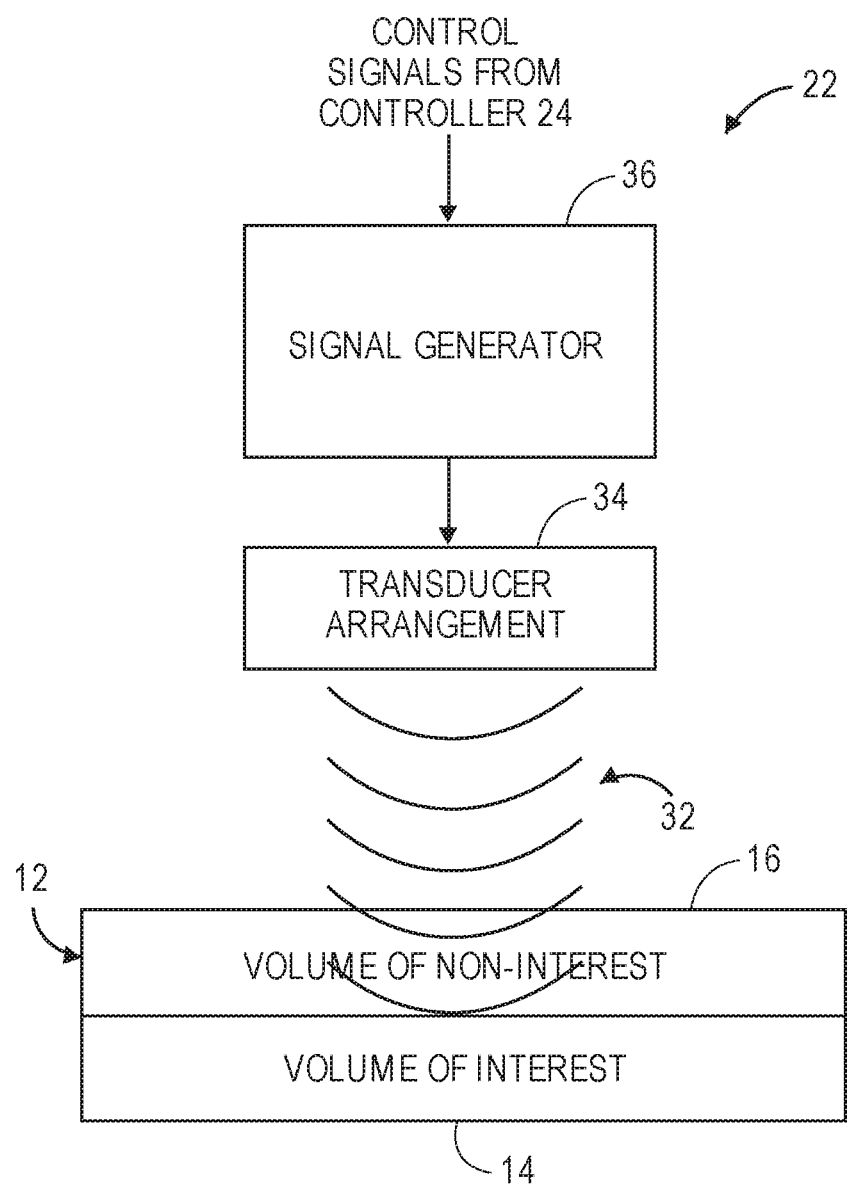
FIG. 9 is a block diagram of one embodiment of an acoustic assembly used in the optical detection system of FIG. 6.

Referring further to FIG. 9, one embodiment of the acoustic assembly 20 includes an ultrasound transducer 34 and a signal generator 36. The ultrasound transducer 34 may take the form of any device that emits ultrasound 32 at a defined amplitude, frequency, phase, and/or duration in response to a controlled drive signal. Significantly, although the ultrasound transducer 34 may be complex, e.g., a piezoelectric phased array capable of emitting ultrasound beams with variable direction, focus, duration, and phase, an array of pressure generating units (e.g., silicon, piezoelectric, polymer or other units), an ultrasound probe, or even an array of laser generated ultrasound (LGU) elements, the ultrasound transducer 34 can be very simple, e.g., a single acoustic element configured for emitting ultrasound beams, since the ultrasound 32 need not be focused. Furthermore, in contrast to ultrasound transducers that need to be relatively large in order to focus the ultrasound to a small voxel in the brain, the ultrasound transducer 34 can be made as small as the "footprint" of the optical masking zone 13, and therefore, can be integrated into a small form-factor device.

Furthermore, for anatomical applications, and in particular, imaging or the detection of optical properties within of the head, because the ultrasound 32 need not penetrate through the skull into the brain in the case where the volume of non-interest 16 is confined to the scalp and skull, its frequency can be much higher (e.g., much greater than 1 MHz, e.g., 5-20 MHz). As such, the ultrasound transducer 34 can be manufactured using much cheaper, modern thin-film transducer fabrication processes, e.g., capacitive micromachined ultrasound transducer (CMUT) technology and piezo micromachined ultrasound transducers (PMUT) technology.

The signal generator 36 is configured for generating alternating current (AC) signals for driving the ultrasound transducer 34 at a defined amplitude, frequency, phase, and duration. The AC drive signal may be electrical or optical, depending on the nature of the ultrasound transducer arrangement. Because a simple acoustic element can be used for the ultrasound transducer 34, the signal generator 36 may comprise a single-channel transmitter, although in the case where the ultrasound transducer 34 comprises a phase-array or multi-channel, the signal generator 36 may comprise a multi-channel transmitter, which could provide more uniform masking of the background light 46. For example, the use of multiple ultrasound elements allows the acoustic waves to be shaped, for instance, that lead to sharper boundaries, correct for skull aberrations, or generally create better defined shapes of ultrasound, whereas a single-element transducer only makes acoustic waves having one basic shape that is subject to distortion by the skull. The signal generator 36 includes control inputs (not shown) for receiving control signals from the controller 26 that cause the ultrasound transducer 34 to emit the ultrasound 32 at the defined amplitude, frequency, phase, and duration. Thus, as will be described in further detail below with respect to FIGS. 16a-16c and 17a-17c), the controller 26 may selectively pulse the ultrasound 32 in certain embodiments.

As briefly discussed above, the ultrasound 32 emitted by the ultrasound transducer 34 creates an optical masking zone 13 in the volume of non-interest 16 that masks out photons exclusively passing through the volume of non-interest 16 from contributing to the detected optical parameter of the volume of interest 14. The mechanism of the masking out of photons occurs via ultrasonic tagging of the photons, which shifts their frequency, causing their interference with the reference light to rapidly oscillate as a fast beat rather than a DC beat in the homodyne case or much faster than an AC beat in the heterodyne case, and thus to integrate out of the detection process by summing to approximately zero. It thus relies on a similar ultrasonic tagging mechanism as UOT, but instead of leading to collection of the tagged photons, it leads to the masking of the tagged photons out of the measurement, leaving only the untagged photons, which did not pass through or minimally passed through the optical masking zone 13 defined by the spatial arrangement of the ultrasound waves in the scattering medium 12.

Figure 10A:
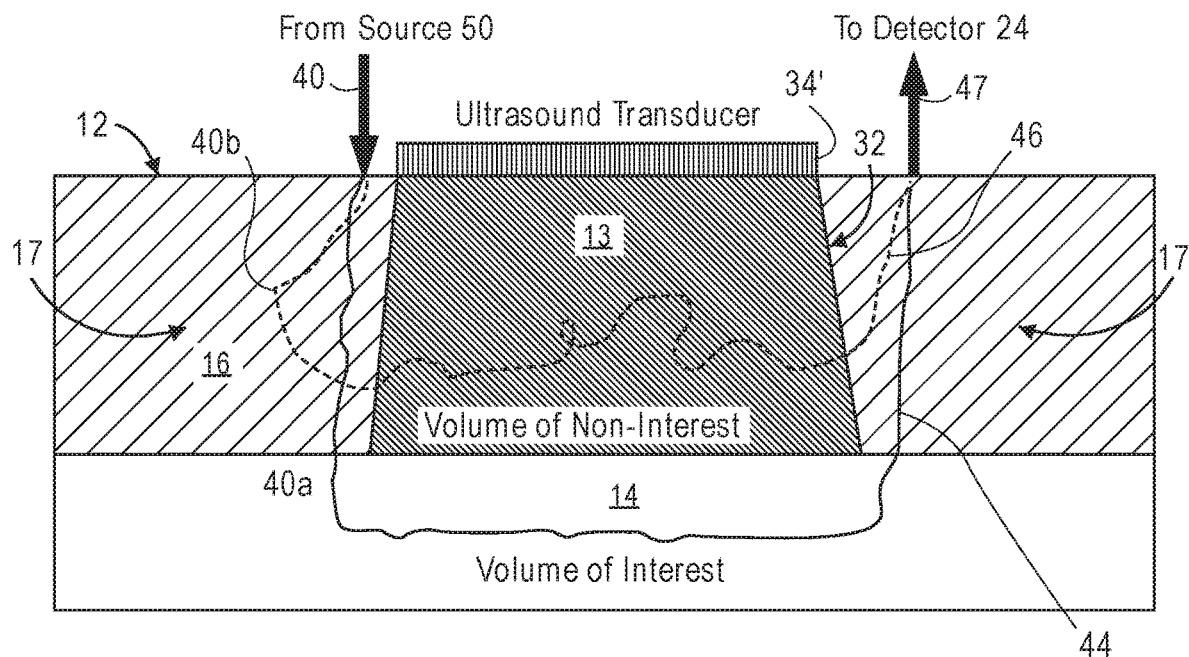
FIG. 10a is a cross-sectional view of one embodiment of an ultrasound transducer of the acoustic assembly of FIG. 9, which can create an optical masking zone in a volume of non-interest.
Figure 10B:
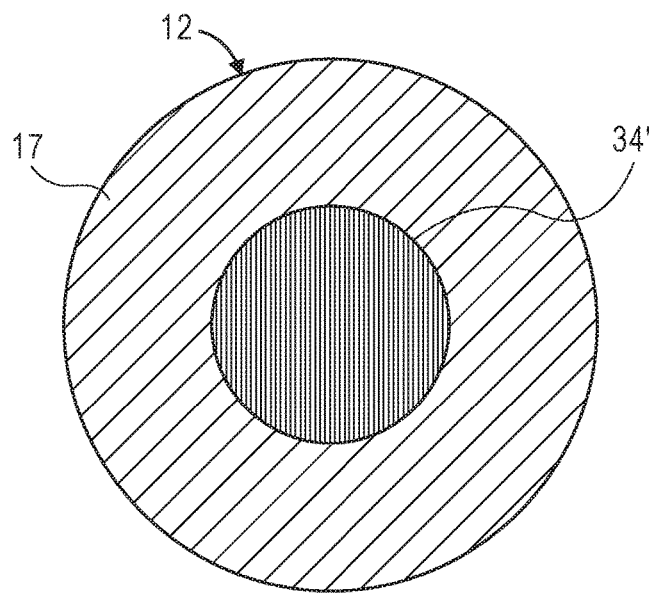

One embodiment of an ultrasound transducer 34' is disc-shaped, as illustrated in FIGS. 10a and 10b. The ultrasound transducer 34' is configured for emitting the ultrasound 32 into the scattering medium 12 to create a cylindrical or frustoconical-shaped optical masking zone 13 that suppresses the second sample light portion 40b that passes through the volume of non-interest 16 as the background light 46. An annular-shaped optical port 17 is created around the optical masking zone 13 in which the sample light 40 can be delivered to the scattering medium 12 for propagation through the volume of interest 14 as the first sample light portion 40a and from which the sample light portion 40a can exit the scattering medium 12 as the signal light 44.

In the illustrated embodiment, the ultrasound transducer 34' is sized to fit between the optical source 50 and the optical detector 24 (both shown in FIG. 6) that are clocked 180 degrees from each other, such that the sample light 40 is delivered through the annular-shaped optical port 17 adjacent one side of the optical masking zone 13, and the resulting signal light 44 exits from the annular-shaped optical port 17 adjacent the opposite side of the optical masking zone 13, as best shown in FIG. 10a. However, the optical source 50 and optical detector 24 can be oriented relative to each other in any suitable manner, such that sample light 40 is delivered through the annular-shaped optical port 17 and the resulting signal light 44 exits from the annular-shaped optical port 17 at any relative angular positions along the annular-shaped optical port 17. It should also be appreciated that the ultrasound transducer 34 need not be disk-shaped, but can be any shape, for example, rectangular, triangular, octagonal, etc., to create a similarly-shaped optical port 17 that surrounds the optical masking zone 13.

Figure 11A:
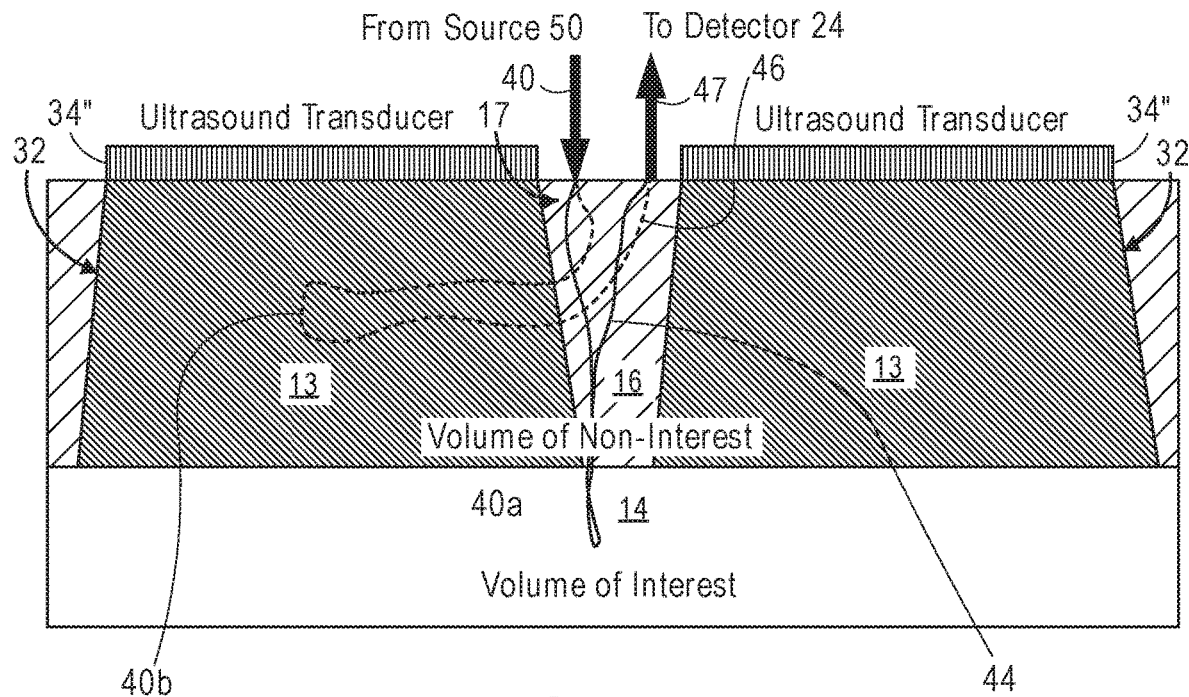
FIG. 11a is a cross-sectional view of another embodiment of an ultrasound transducer of the acoustic assembly of FIG. 9, which can create an optical masking zone in a volume of non-interest.
Figure 11B:
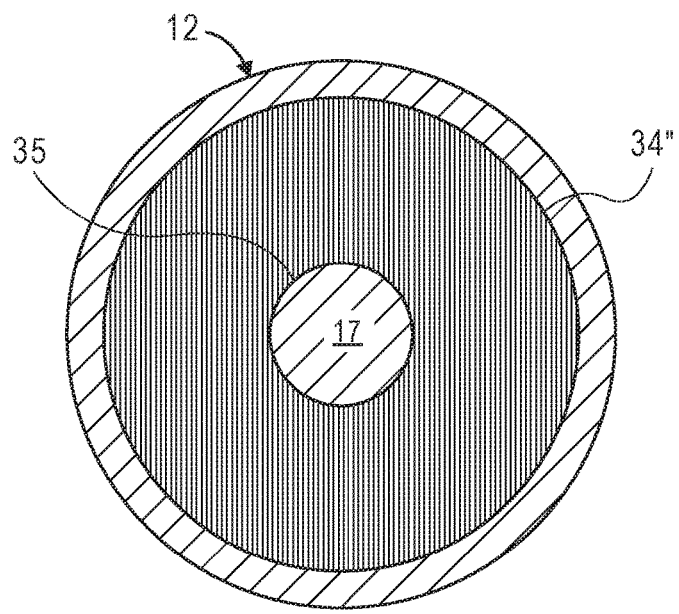

Another embodiment of an ultrasound transducer 34" is disc-shaped, but has a central aperture 35, as illustrated in FIGS. 11a and 11b. The ultrasound transducer 34" is configured for emitting the ultrasound 32 into the scattering medium 12 to create an annular-shaped optical masking zone 13 that suppresses the second sample light portion 40b that passes within and then back out the volume of non-interest 16 as the background light 46. A cylindrical or frustoconical-shaped optical port 17 is created within the optical masking zone 13 in which the sample light 40 can be delivered to the scattering medium 12 for propagation within the volume of interest 14 as the first sample light portion 40a and back out of the volume of interest 14 as the signal light 44, as best illustrated in FIG. 11a.

In the illustrated embodiment, the central aperture 35 of the ultrasound transducer 34" is sized to accommodate a closely spaced or collocated optical source 50 and optical detector 24 (both shown in FIG. 6), such that the sample light 40 is delivered through the optical port 17 and the resulting signal light 44 exits from the optical port 17. It should also be appreciated that the ultrasound transducer 34 need not be disk-shaped, but can be any shape, for example, rectangular, triangular, octagonal, etc. Similarly, the central aperture 35 need not be circular, but can be any shape, for example, rectangular, triangular, octagonal, etc.

It should be appreciated that the arrangement of the ultrasound transducer 34, optical source 50, and detector 24 illustrated in FIGS. 11a and 11b lends itself well to OCT techniques that rely on the backscattering of the "straight path" photons at a selected depth within the scattering medium 12. Furthermore, because the background light 46 has been suppressed by the optical masking zone 13, the optical source and detector of such OCT system need not be separated a relatively long distance from each other in order to reduce the fraction of background light 46 relative to the signal light 44, but instead, can be adjacent to each other or even co-located at the center aperture 35 of the ultrasound transducer 34, thereby maximizing the amount of signal light 44 detected by the optical detector 26, and further improving imaging spatial resolution.

It should be appreciated that the extent to which the background light 46 is decorrelated from the holographic beat component of the interference light pattern 48 is dependent on the frequency of ultrasound 32 and the duration of the sample light 40 within the measurement period. That is, the more cycles of ultrasound 32 per duration of the sample light 40, the more the background light 46 is decorrelated from the holographic beat component. Although it is desirable to select a frequency of the ultrasound 32 that is high as possible and a duration of the sample light 40 as low as possible to maximize decorrelation of the background signal from the holographic beat component, it should be appreciated that selection of a higher frequency ultrasound 32 must be balanced against the requirement that the frequency of the ultrasound 32 be low enough to allow sufficient penetration of the ultrasound 32, as discussed above, and the duration of the sample light 40 must be balanced against the requirement that the duration of the sample light 40 be less than the decorrelation time of the tissue, as discussed below with respect to FIG. 14.

It can be shown that, assuming the mechanism of masking the background light 46 that travels through the volume of non-interest 16 is decorrelation time "scrambling" by the ultrasound 32 (i.e., the addition of phase information at high frequency (in this case, the frequency of the ultrasound 32)), there will be several orders of suppression of the background light 46.

Figure 12:
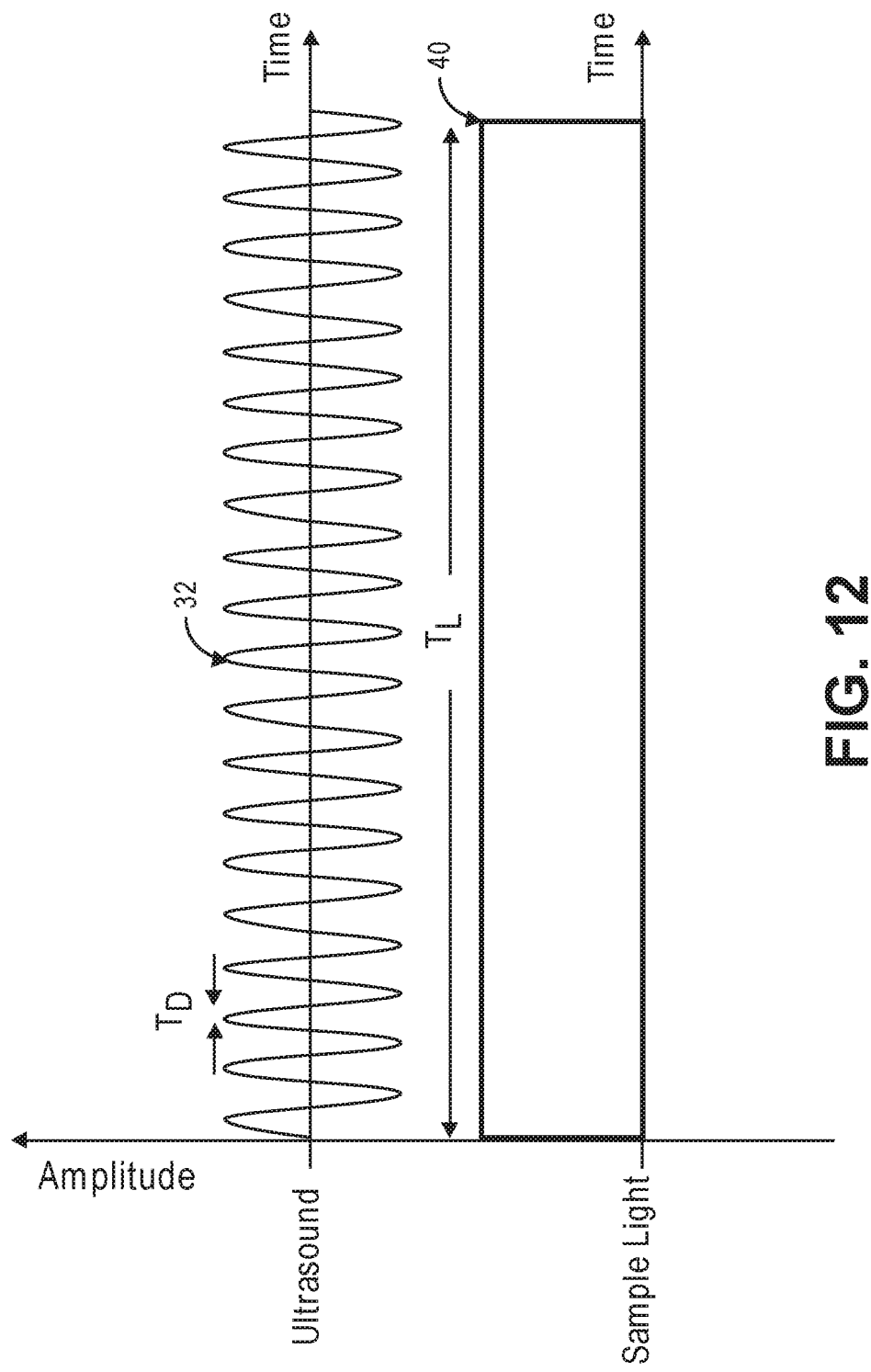
FIG. 12 is a diagram illustrating an exemplary relationship between a frequency of ultrasound emitted by the acoustic assembly of FIG. 9, and the duration of a pulse of sample light delivered by the interferometer of FIG. 7, for masking background light.

For example, referring to FIG. 12, if the ultrasound 32 has an exemplary frequency that defines a decorrelation time $T_D$, which can be assumed to be one-quarter the period of the ultrasound 32, and the sample light 40 has an exemplary duration $T_L$, the suppression of the background light 46 can be approximated as:

$$\text{Suppression} = T_D/T_L. \qquad [2]$$

For example, if the sample light 40 has a duration $T_L$ set to 10 μs, and the frequency of the ultrasound is 20 MHz, such that decorrelation time $T_D$ is 12.5 ns (i.e., one-quarter of the period (50 ns) of the ultrasound 32), then, using equation [2], the suppression of the background light 46 will be $T_D/T_L = 12.5$ ns/10 μs = 1/800, which is nearly three orders of magnitude of suppression of the background light 40. As dictated by equation [2], as the frequency of the ultrasound 32 increases, the decorrelation time $T_D$ will decrease, thereby increasing the decorrelation of the background light 46 from the holographic beat component of the interference light pattern 48.

If the mechanism of masking the background light 46 is acoustic encoding by the ultrasound 32 (i.e., merely frequency shifted by the ultrasound 32 in contrast to scrambling), the suppression of the background light 46 can be approximated as:

$$\text{Suppression} = 1/(T_L * 2\pi * f_{us}). \quad [3]$$

Again, assuming that the sample light 40 has a duration $T_L$ set to 10 μs, and the frequency of the ultrasound is 20 MHz, then, using equation [3], the suppression of the background light 46 will be $1/(T_L * 2\pi * f_{us}) = 1/(10\mu s * 2\pi * 20 \text{ MHz}) = 1/1200$, which is three orders of magnitude of suppression of the background light 46. As dictated by equation [3], as the frequency $f_{us}$ of the ultrasound 32 increases, the decorrelation of the background light 46 from the holographic beat component of the interference light pattern 48 will likewise increase.

Although decorrelation of the background light 46 from the holographic beat component of the interference light pattern 48 has been shown to increase with the frequency of the ultrasound 32 (preferably within the range of 5-20 MHz when used to detect optical properties of the brain through the skull), it should be noted that this advantage must be balanced with the penetration of the ultrasound 32 into the scattering medium 12, which decreases as the frequency of the ultrasound 32 increases, as described in further detail below. Thus, it is desirable to set the frequency of the ultrasound 32 as high as possible, while achieving the desired penetration of the ultrasound 32 into the scattering medium 12.

Figure 13A:
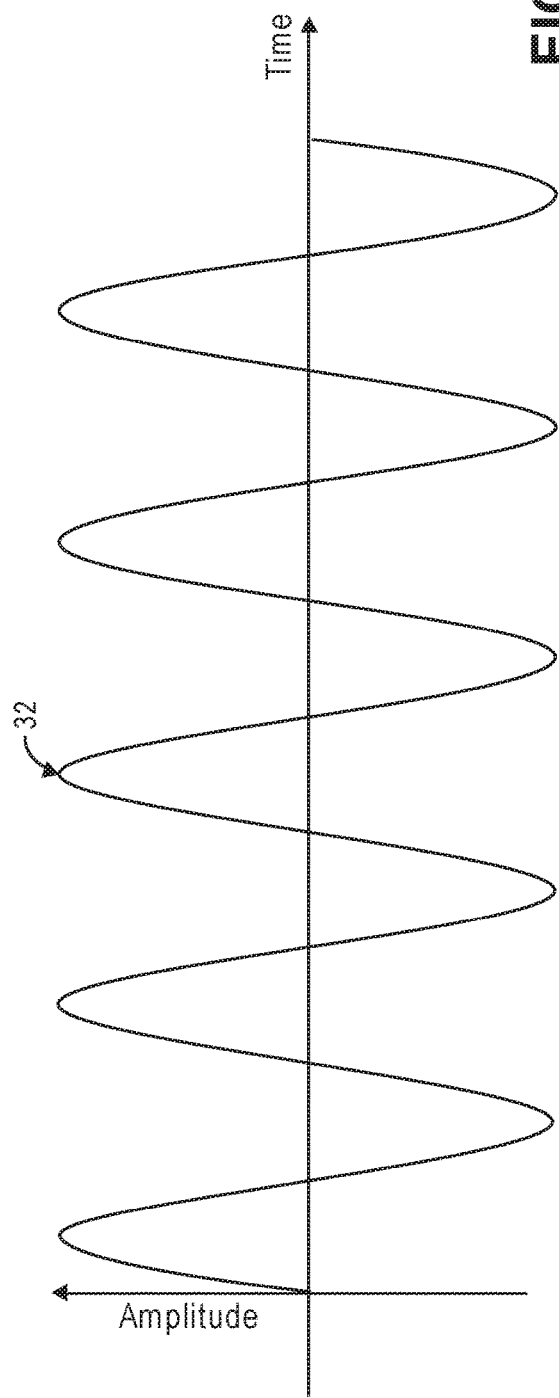
FIG. 13a is a first exemplary waveform of the ultrasound emitted by the acoustic assembly of FIG. 9.

Although the ultrasound 32 may have a uniform frequency, a uniform amplitude, and a uniform phase during the measurement period, as illustrated in FIG. 13*a*, it should be appreciated that the masking of the background light 46 from the detected optical parameter of the volume of interest 14 can be further increased by varying at least one of the frequency, the amplitude, and the phase of the ultrasound 32 during the measurement period.

Figure 13B:
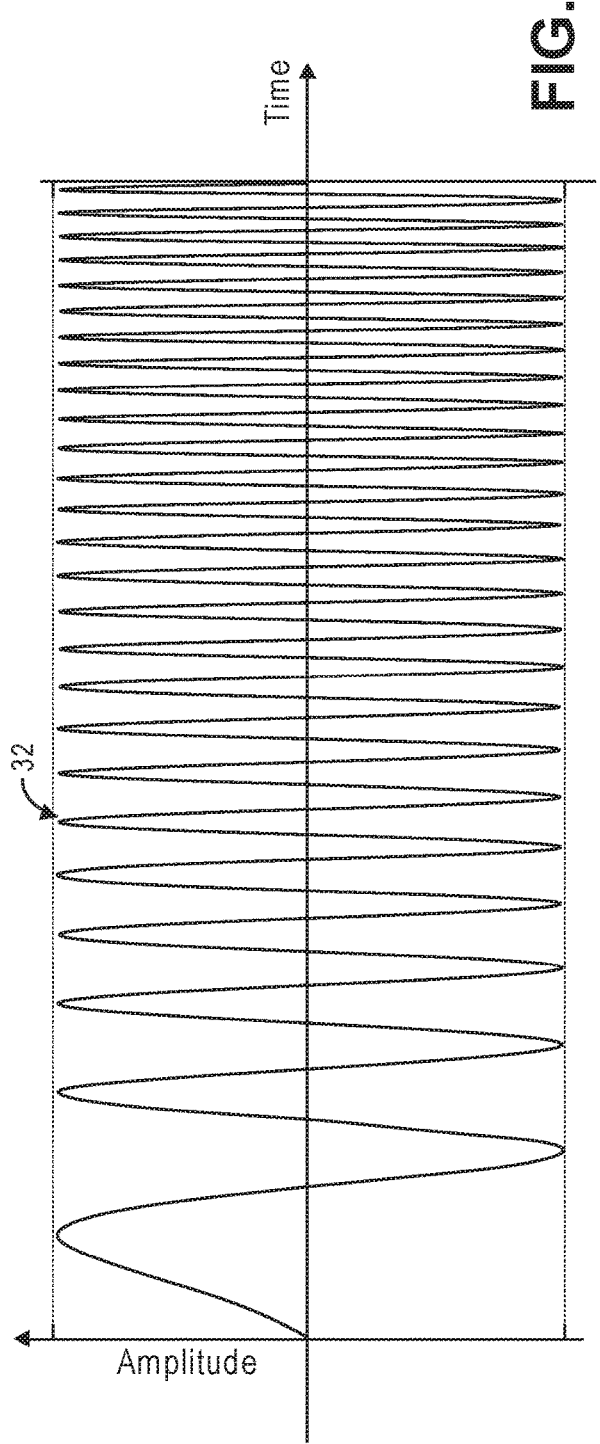
FIG. 13b is a second exemplary waveform of the ultrasound emitted by the acoustic assembly of FIG. 9.
Figure 13C:
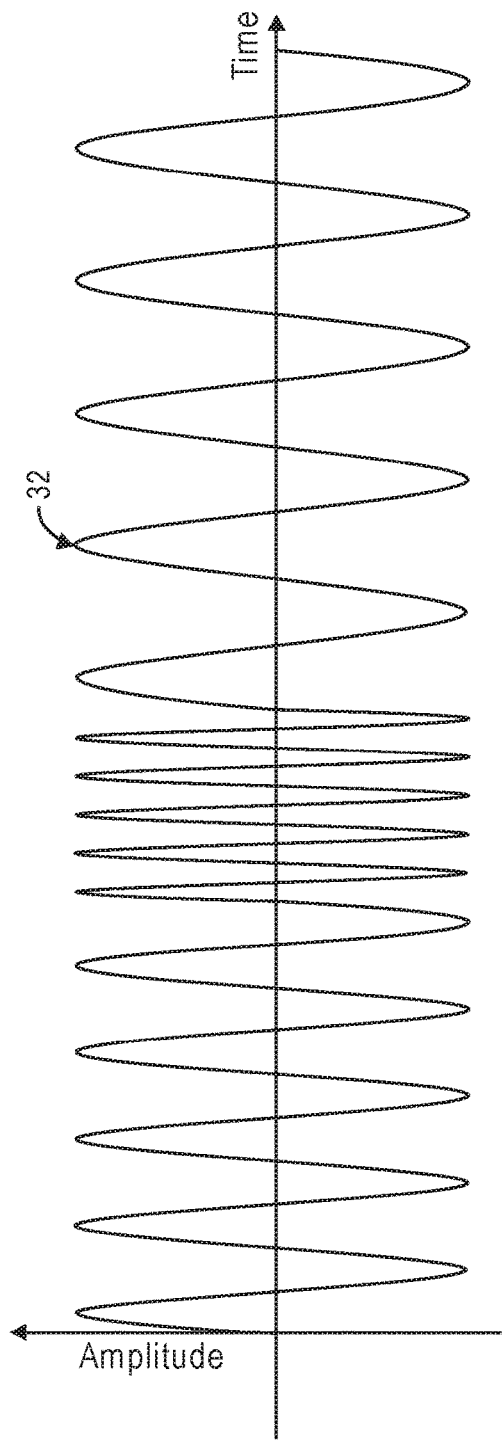
FIG. 13c is a third exemplary waveform of the ultrasound emitted by the acoustic assembly of FIG. 9.
Figure 13D:
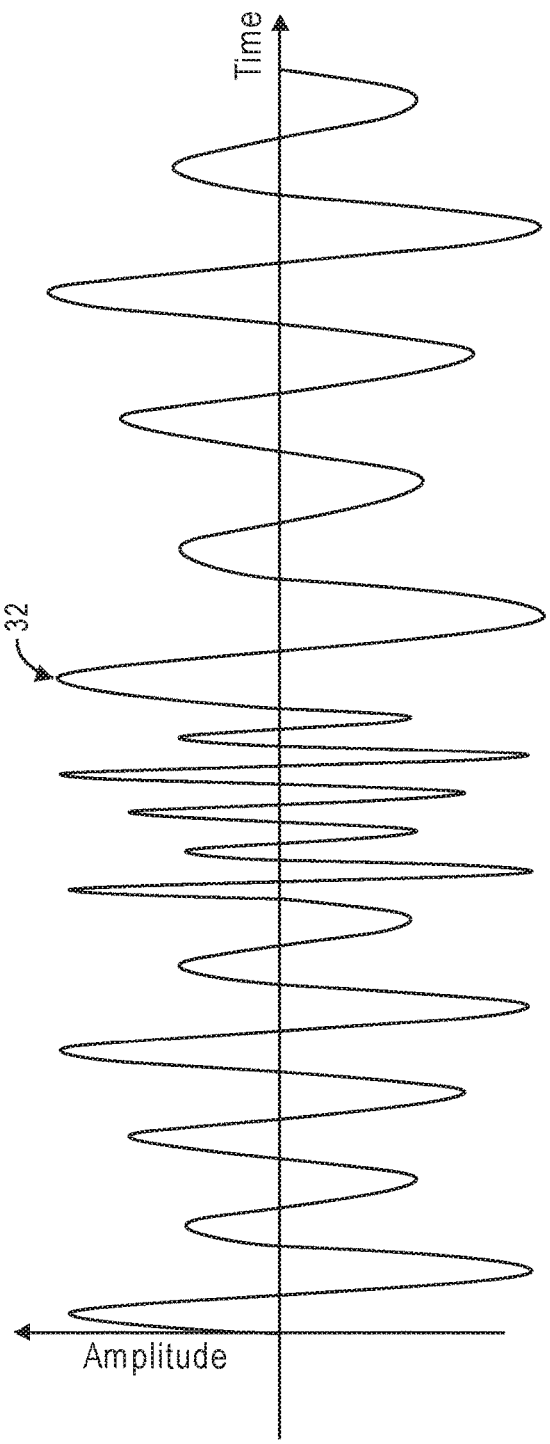
FIG. 13d is a fourth exemplary waveform of the ultrasound emitted by the acoustic assembly of FIG. 9.
Figure 13E:
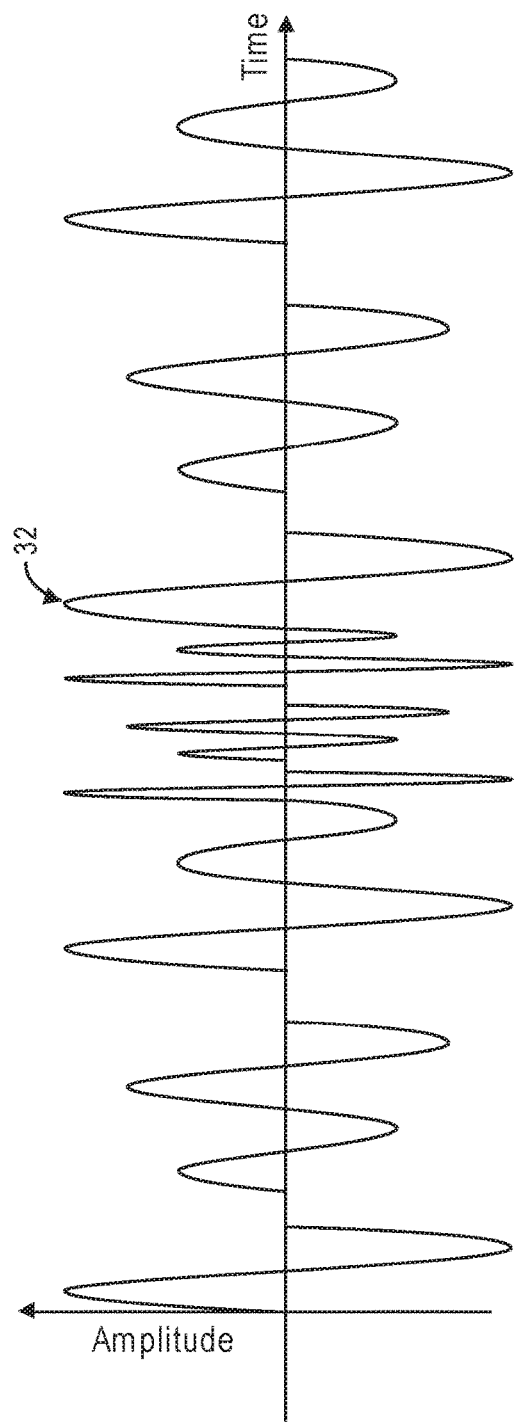
FIG. 13e is a fifth exemplary waveform of the ultrasound emitted by the acoustic assembly of FIG. 9.
Figure 13F:
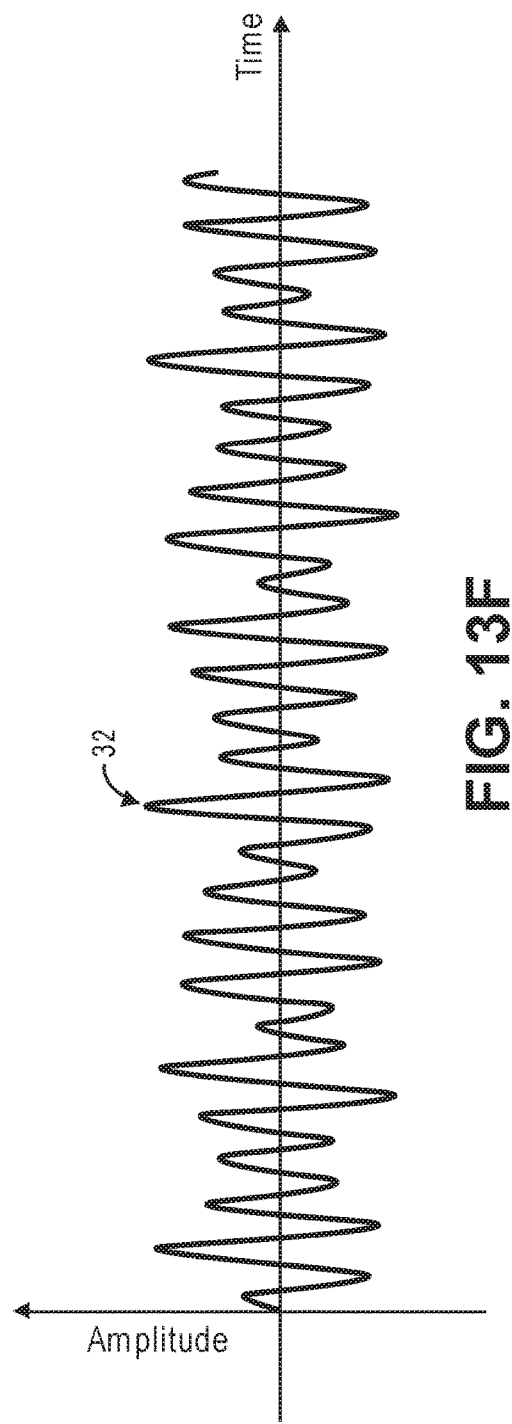
FIG. 13f is a sixth exemplary waveform of the ultrasound emitted by the acoustic assembly of FIG. 9.

For example, the frequency of the ultrasound 32 may be varied by sweeping it across a range of frequencies (i.e., the frequency is gradually or incrementally changed), as illustrated in FIG. 13*b*, or the frequency of the ultrasound 32 may be varied by switching it between different random frequencies (i.e., by jumping from one frequency to another frequency), as illustrated in FIG. 13*c*. Notably, sweeping the frequency of the ultrasound 32 is easier to implement in the hardware (e.g., the transducer 34, driver, amplifier, etc.), although switching the frequency of the ultrasound 32 between random frequencies may be more effective in masking the background light 46 from the detected optical parameter of the volume of interest 14. Two or more of the frequency, the amplitude, and the phase of the ultrasound 32 may be varied during the measurement period to further mask the background light 46 from the detected optical parameter of the volume of interest 14. For example, as illustrated in FIG. 13*d*, both the amplitude and frequency of the ultrasound 32 may be varied, and as illustrated in FIG. 13*e*, all three of the amplitude, frequency, and phase of the ultrasound 32 may be varied. The background light 46 can also be further masked from the detected optical parameter of the volume of interest 14 by using an arbitrary waveform selected for maximum masking of the background light 46, as illustrated in FIG. 13*f*.

Referring now to FIG. 14, the relationship between the pulses of sample light 40, the measurement period τ, and the active period of the optical detector 24 (in the case where the optical detector 24 is a camera, a single camera frame) (exposure or readout time)), will be discussed. During the acquisition of data characterizing the volume of interest 14, one or more pulses of the sample light 40 is delivered into the scattering medium 12 during each measurement period τ. Although, in the embodiment illustrated in FIG. 14, only a single rectangular pulse of the sample light 40 is delivered into the scattering medium 12 during each measurement period τ, it should be appreciated that other sample light pulse shapes and number of sample light pulses can be used in each measurement period τ, including, e.g., double Gaussian or even arbitrarily-shaped pulses, as illustrated in U.S. patent application Ser. No. 16/299,067, entitled "Non-Invasive Optical Detection Systems and Methods in Highly Scattering Medium," which is expressly incorporated herein by reference.

In this example, the respective measurement period t is equal to the duration of a single pulse of the sample light 40 to maximize the data acquisition speed, although in alternative embodiments, the measurement period t may extend over multiple pulses of the sample light 40. In the illustrated embodiment, the duty cycle $\tau_{duty}$ of the pulsed sample light 40 is selected to match the frame rate of the optical detector 24 (in the case where the optical detector 24 is a camera), such that there is only one measurement period τ for each frame of the optical detector 24, although the duty cycle $\tau_{duty}$ of the pulsed sample light 40 may be selected, such that there are multiple measurement periods τ for each frame of the optical detector 24. The frame rate of the optical detector 24 may be much slower than the pulse of sample light 40, and can be turned on prior to the pulse of sample light 40 and turned off after the pulse of sample light 40.

The measurement period τ, and in this case, the duration of the pulse of sample light 40, is preferably selected to be no longer than the speckle decorrelation time of the scattering medium 12. The speckle decorrelation time is due to the scatterers' motion inside the scattering medium 12, and rapidly decreases with the depth at which the scattering medium 12 is to be detected, and in particular, scales super-linearly with the depth into the scattering medium at which the volume of interest 14 is located, falling to microseconds or below as the detected depth extends to the multi-centimeter range.

It should also be noted that although the measurement period τ is illustrated as being on the order of a single active period of the optical detector 24, as shown in FIG. 14, the measurement period τ may be much less than the duration of a single active period of the optical detector 24. In particular, if the optical detector 24 is a camera, due to its limited frame rate, the duration of each camera frame may be much greater than the decorrelation speckle time of the scattering medium 12, thus dictating that the measurement period τ be much less than the duration of each camera frame.

Depending on the implementation of the optical detection system 10, the ultrasound 32 may be either continuous wave (CW) or pulsed wave (PW).

Assuming that the volume of interest 14 is deeper in the scattering medium 12 than the volume of non-interest 16, if the ultrasound 32 is CW, it is preferred that the frequency of the ultrasound 32 be selected, such that it initially passes through the volume of non-interest 16 without substantially penetrating into the volume of interest 14. In this manner, all of the ultrasound 32 delivered by the ultrasound transducer 34 into the scattering medium 12 will be substantially confined within the volume of non-interest 16, as described above.

In this manner, the background light 46 passing through the volume of non-interest 16 will be decorrelated from the holographic beat component of the interference light pattern 48, while not decorrelating the signal light 44 passing through the volume of interest 14 from the holographic beat component of the interference light pattern 48. That is, the frequency of the ultrasound 32 should be low enough such that it passes through the volume of non-interest 16, but high enough, such that it is suppressed to almost zero at the interface between the volume of interest 14 and the volume of non-interest 16.

Figure 15:
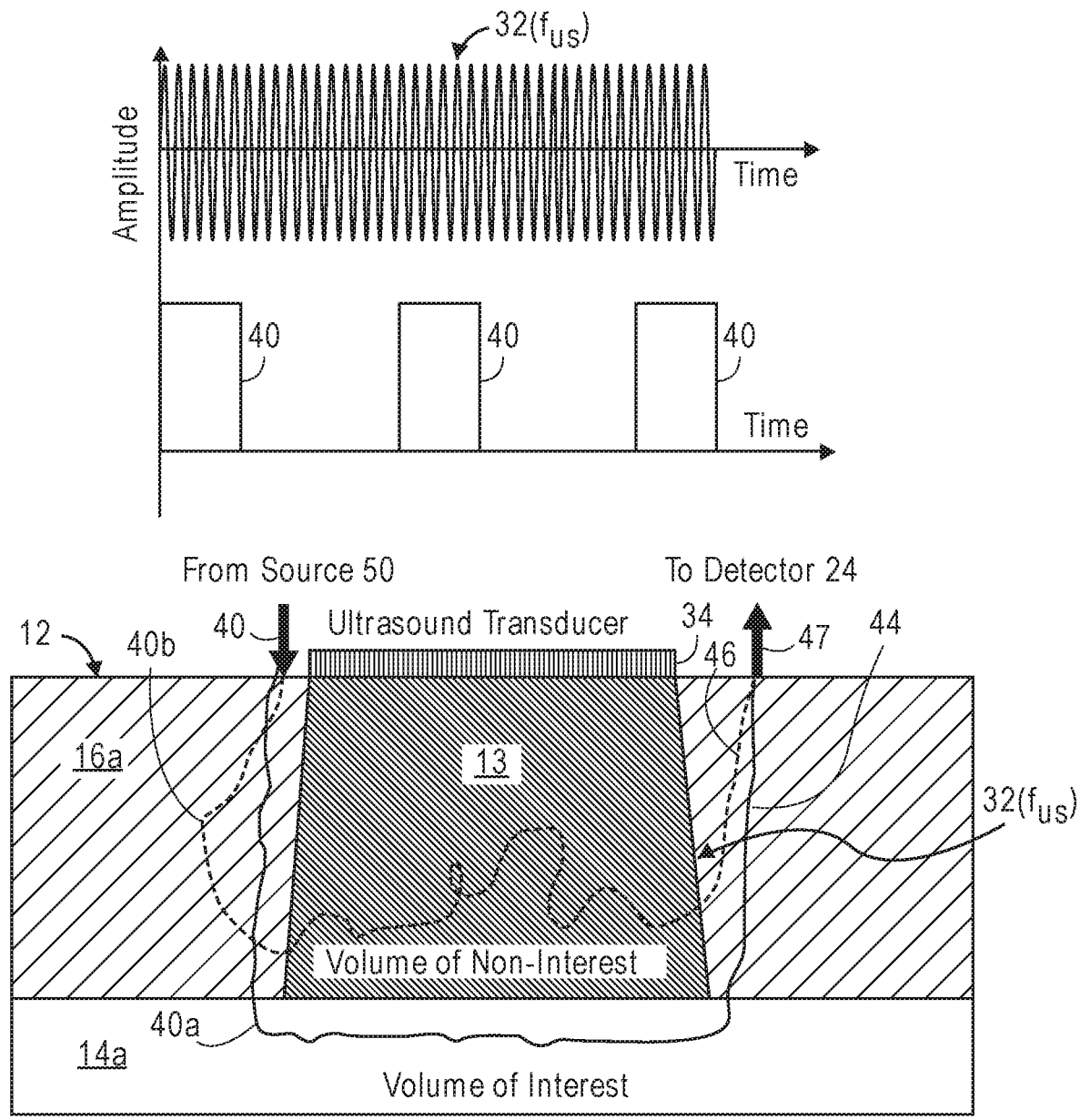
FIG. 15 is a diagram illustrating one exemplary technique used by the optical detection system of FIG. 6 to confine an optical masking zone created by continuous wave (CW) ultrasound within a volume of non-interest.

For example, as illustrated in FIG. 15, pulses of the sample light 40 (three shown) are delivered into the scattering medium 12 from the optical source 50 of the interferometer 20 during the continuous delivery of the ultrasound 32 from the ultrasound transducer 34 of the acoustic assembly 22. The ultrasound 32 emitted by the ultrasound transducer 34 is optimally shown passing through the volume of non-interest 16, but not passing into the volume of interest 14, creating an optical masking zone 13 that is confined within the volume of non-interest 16.

As such, the first sample light portion 40a, which does not pass through the optical masking zone 13, and exits the scattering medium 12 as signal light 44, is not affected by the ultrasound 32, and thus, will be correlated with the holographic beat component of the interference light pattern 48, whereas the second sample light portion 40b, which does pass through the optical masking zone 13, and exits the scattering medium 12 as background light 46, will be affected by the ultrasound 32 in the manner described above, and thus, will be decorrelated from the holographic beat component of the interference light pattern 48.

In this case, it is preferred that the frequency $f_{us}$ of the ultrasound 32 be uniform during the entire measurement period, such that the extent that the ultrasound 32 penetrates into the scattering medium 12 remains consistent during the delivery of the sample light 40 into the scattering medium 12, thereby providing a stable and predictable optical masking zone 13 that does not change in size or location over time.

If the ultrasound 32 is PW, the frequency of the ultrasound 32 may be selected, such that it passes through both the volume of non-interest 16 and the volume of interest 14. In this case, the controller 26 will operate both the interferometer 20 and the acoustic assembly 22, such that the pulse of sample light 40 is only applied when no portion of the ultrasound 32 is disposed within the volume of interest 14, thus confining the optical masking zone 13 within the volume of non-interest 16. In this manner, all of the ultrasound 32 delivered by the ultrasound transducer 34 into the scattering medium 12 will be substantially confined within the volume of non-interest 16, as described above. Thus, the orientation of the volume of interest 14 and volume of non-interest 16 relative to the ultrasound transducer 34 may be arbitrary.

Figure 16A:
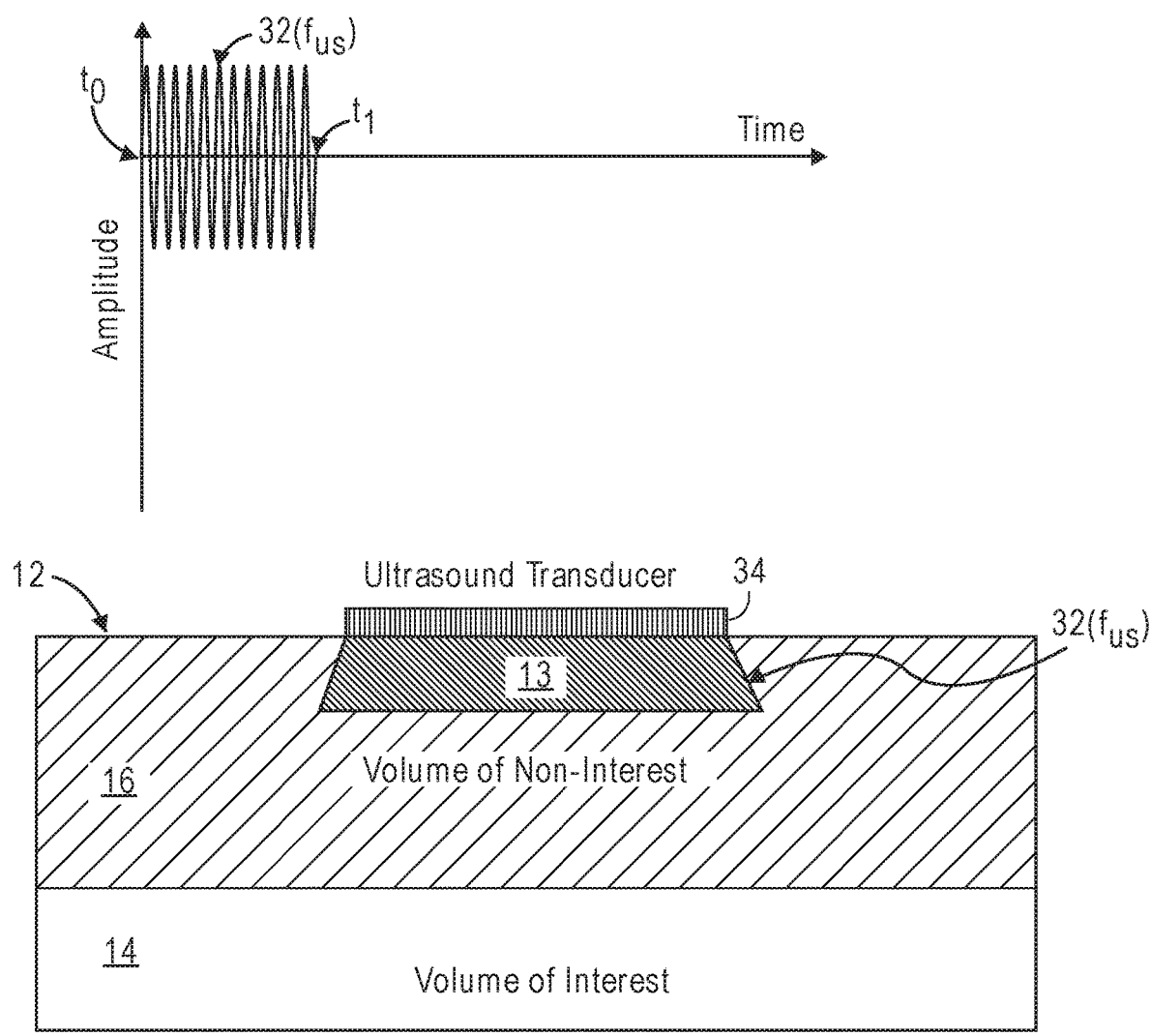
FIGS. 16a-16c are diagrams illustrating another exemplary technique used by the optical detection system of FIG. 6 to confine an optical masking zone created by pulsed wave (PW) ultrasound within a volume of non-interest.
Figure 16B:
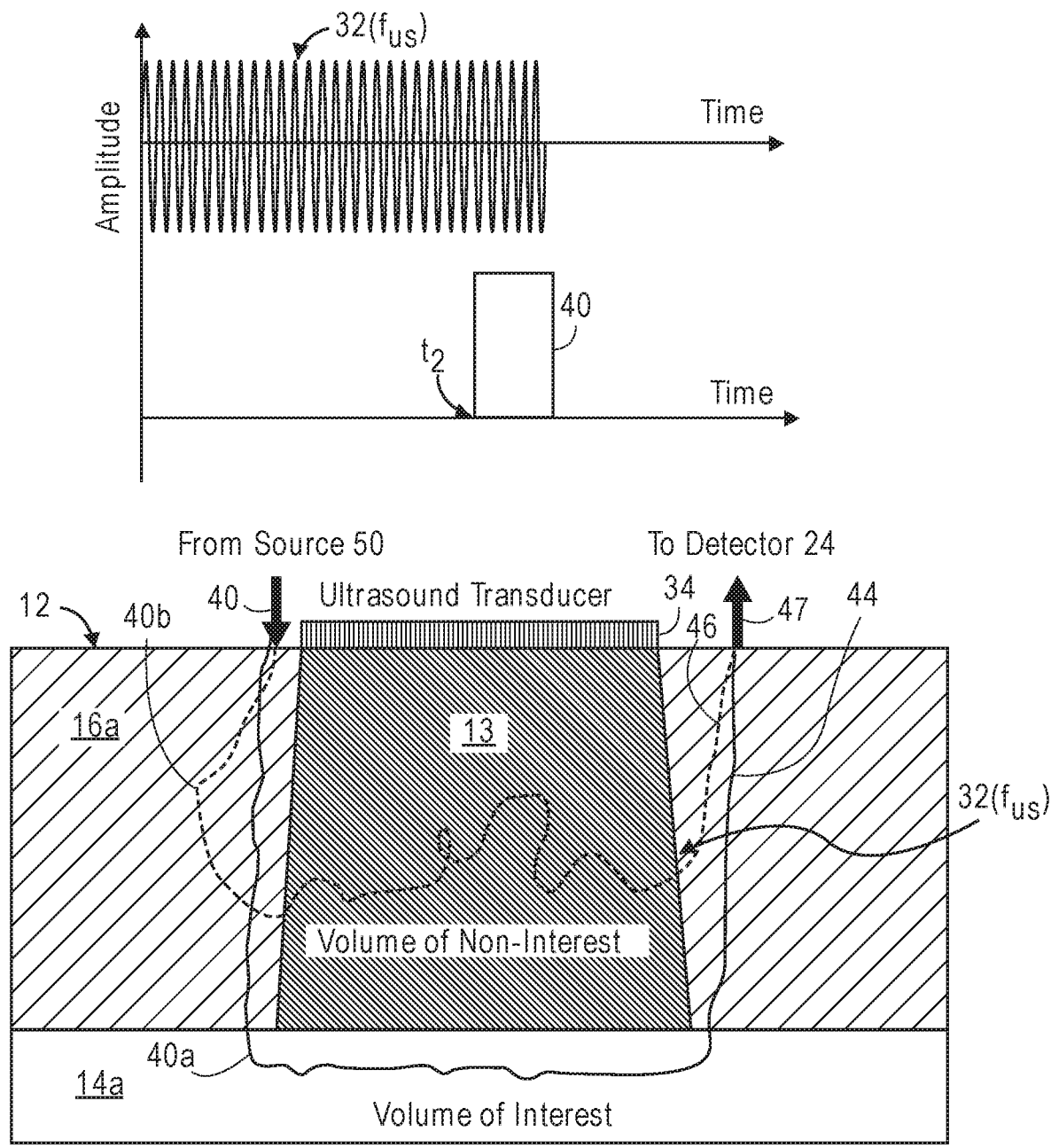
Figure 16C:
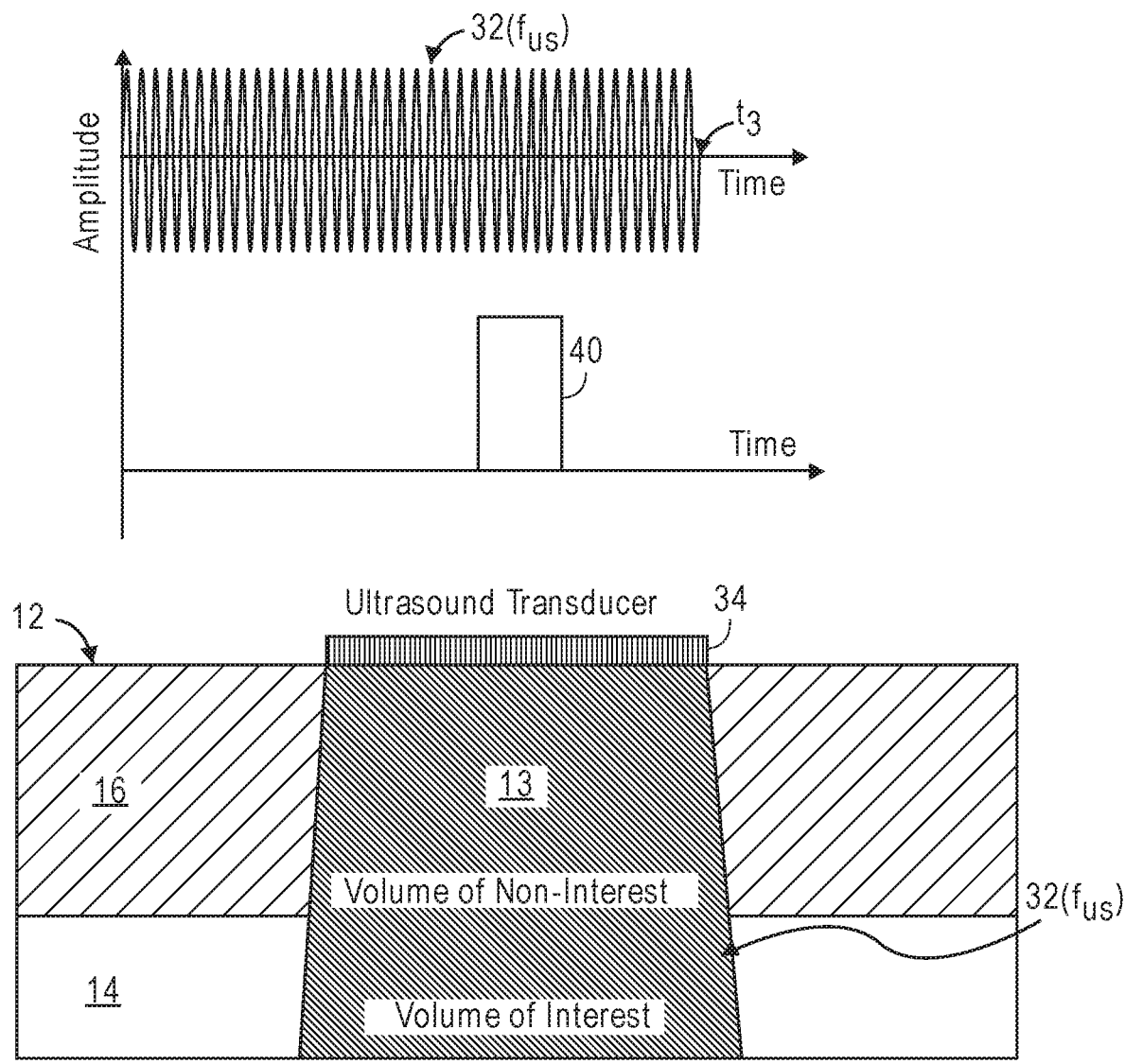

As illustrated in FIGS. 16a-16c, the ultrasound transducer 34 is closer to the volume of non-interest 16 than to the volume of interest 14 (i.e., the volume of interest 14 is deeper in the scattering medium 12 than the volume of non-interest 16 is in the scattering medium 12). In this case, the pulse of ultrasound 32 will first be delivered to the scattering medium 12 at time $t_0$, and at time $t_1$, the pulse of ultrasound 32 begins to enter the volume of non-interest 16, as illustrated in FIG. 16a. At time $t_2$, the pulse of sample light 40 will subsequently be delivered to the scattering medium 12 just before the pulse of ultrasound 32 enters the volume of interest 14, as illustrated in FIG. 16b. Although delivery of the pulse of ultrasound 32 is illustrated as continuing after time $t_2$, it should be appreciated that delivery of the pulse of ultrasound 32 can be ceased at time $t_2$.

Because the speed of light is many orders greater than the speed of ultrasound, the first sample light portion 40a will, in effect, pass through the volume of interest 14 before the pulse of ultrasound 32 reaches the volume of interest 14. Thus, at time $t_2$, the optical masking zone 13 resulting from the ultrasound 32 will be confined within the volume of non-interest 16. As such, the first sample light portion 40a, which does not pass through the optical masking zone 13, exits the scattering medium 12 as the signal light 44 that is not affected by the ultrasound 32, and thus, will be correlated with the holographic beat component of the interference light pattern 48, whereas the second sample light portion 40b, which passes through the optical masking zone 13, exits the scattering medium 12 as background light 46 that will be affected by the ultrasound 32, and thus, will be decorrelated from the holographic beat component of the interference light pattern 48. After the pulse of sample light 40 is delivered to the scattering medium 12 (in effect, the optical parameter in the volume of interest 14 has already been detected), the pulse of ultrasound 32 passes through the volume of interest 14 at time $t_3$, as illustrated in FIG. 16c.

Figure 17A:
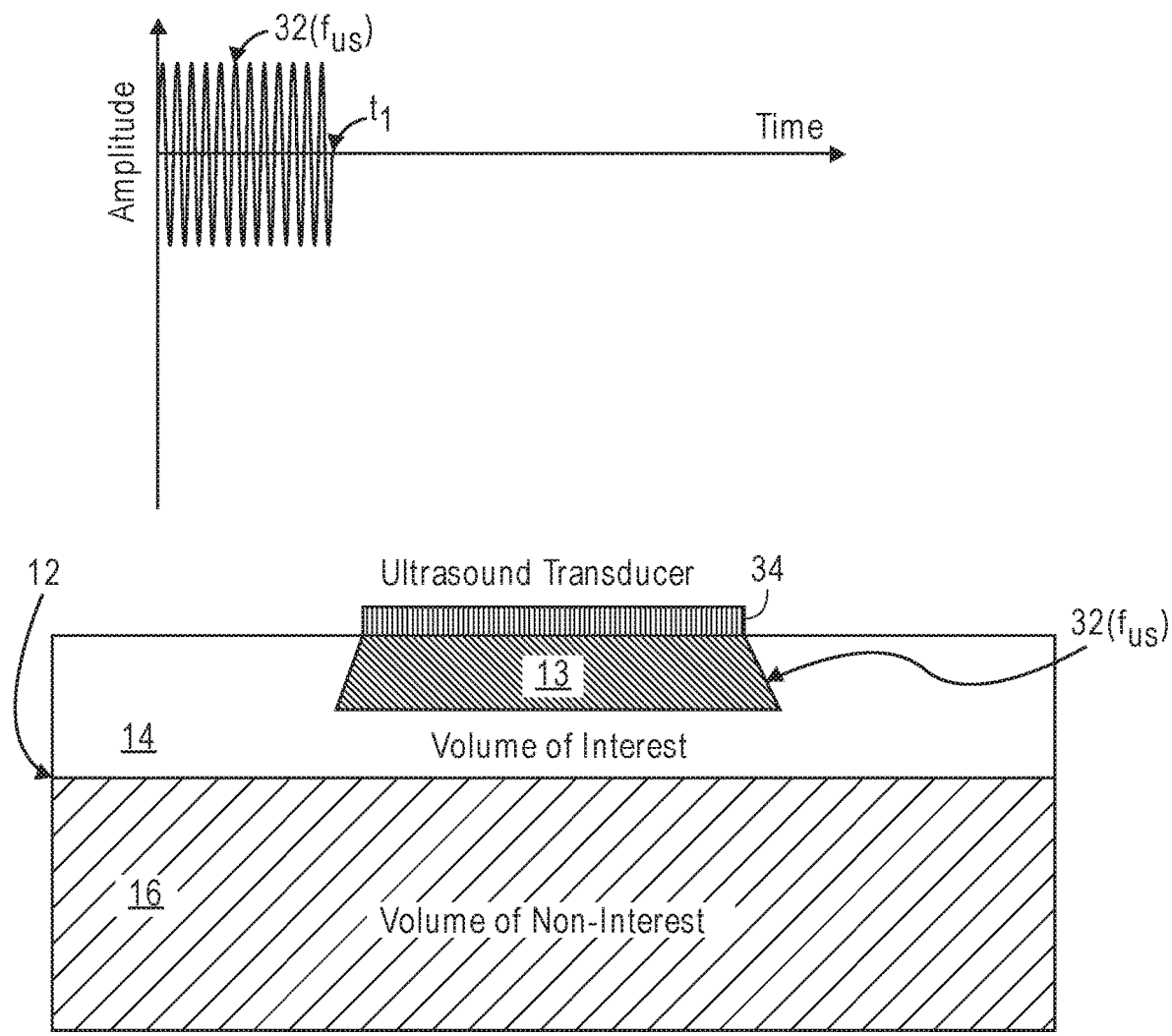
FIGS. 17a-17c are diagrams illustrating still another exemplary technique used by the optical detection system of FIG. 6 to confine an optical masking zone created by PW ultrasound within a volume of non-interest.
Figure 17B:
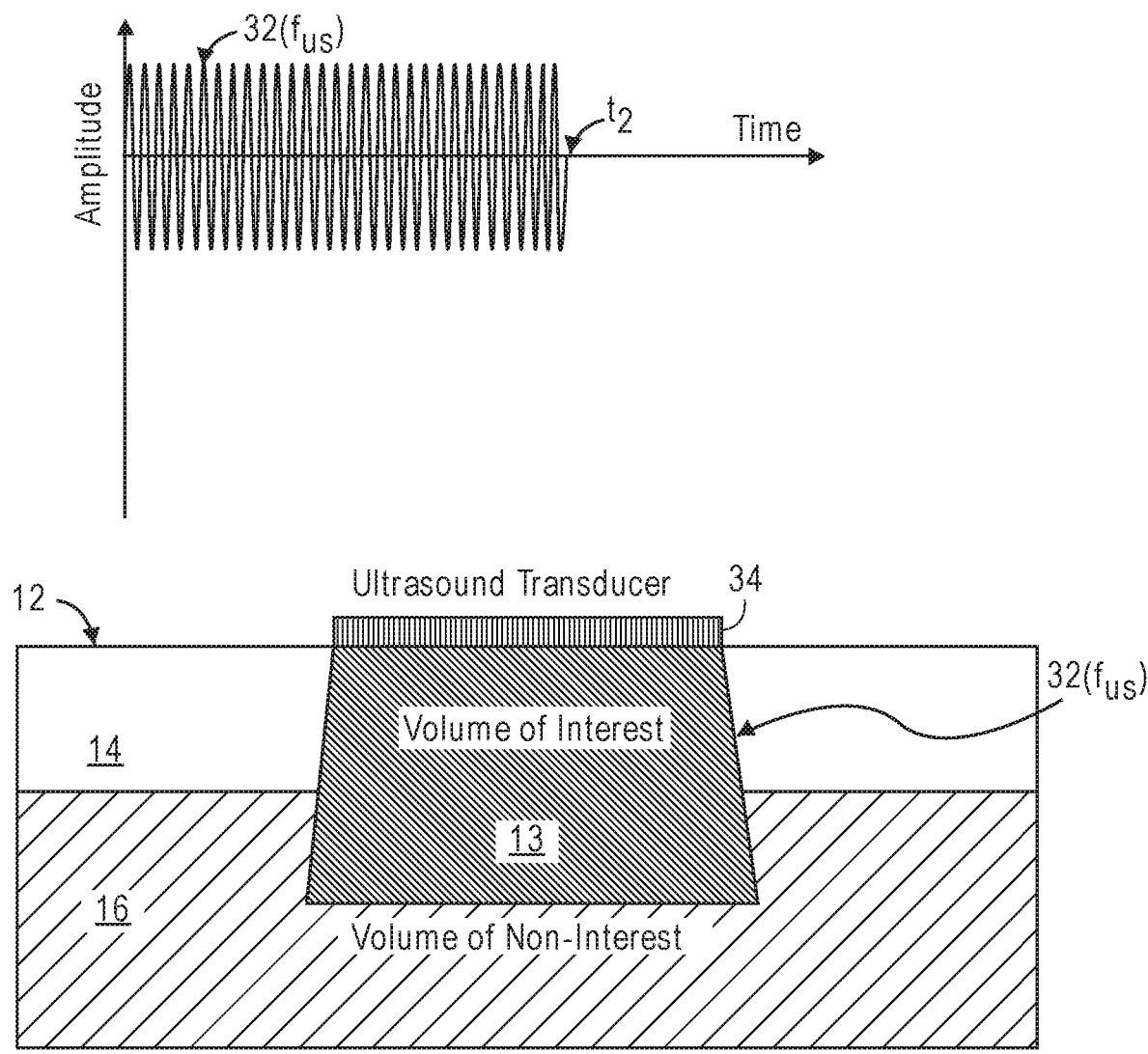
Figure 17C:
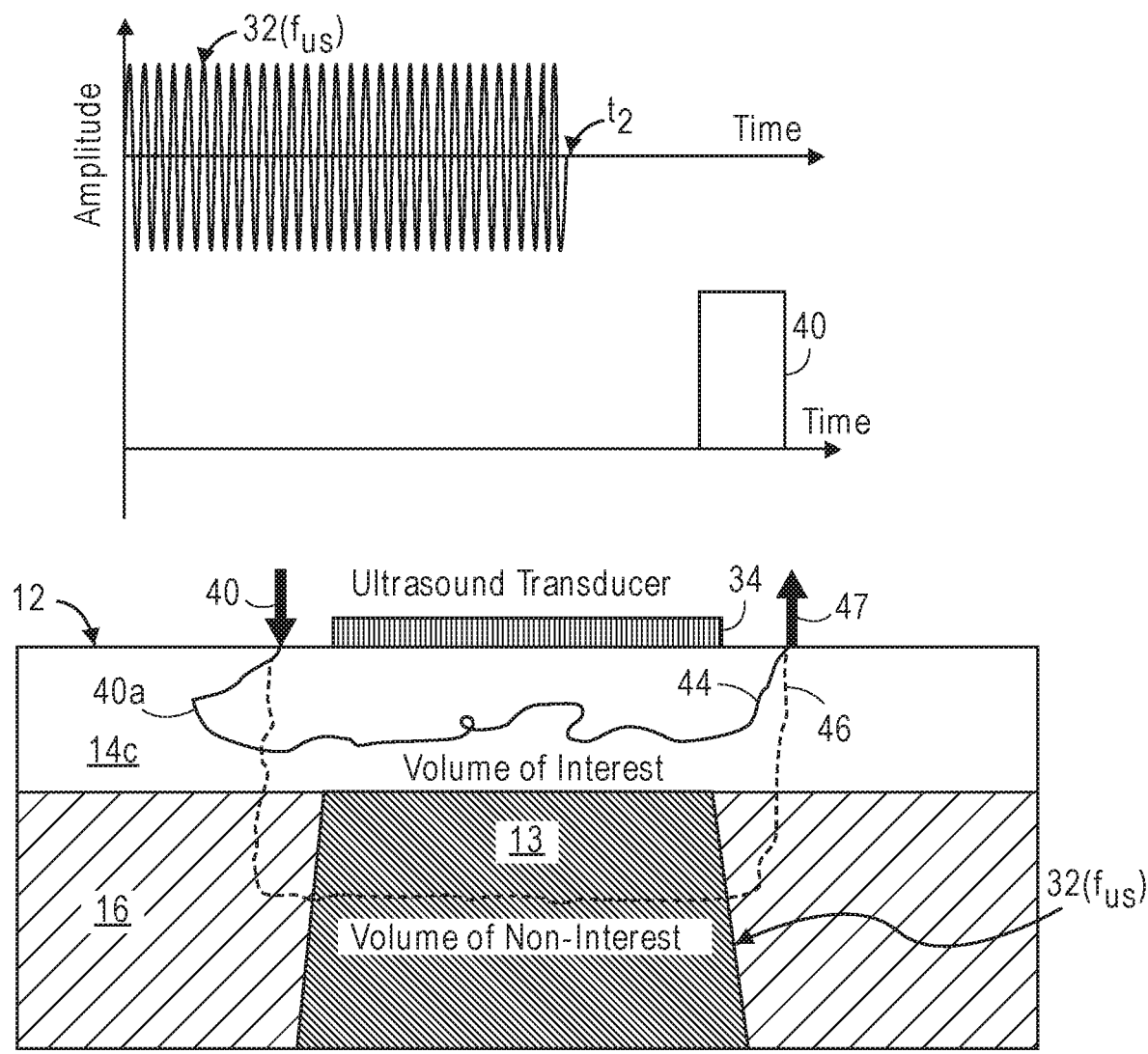

As illustrated in FIGS. 17a-17c, the ultrasound transducer 34 is closer to the volume of interest 14 than to the volume of non-interest 16 (i.e., the volume of interest 14 is shallower than the volume of non-interest 16). In this case, the pulse of ultrasound 32 will first be delivered to the scattering medium 12 at time $t_0$, and at time $t_1$, the pulse of ultrasound 32 enters the volume of interest 14, as illustrated in FIG. 17a. At time $t_2$, delivery of the pulse of ultrasound 32 into the scattering medium 12 ceases, as illustrated in FIG. 17b. The interval between time $t_1$ and $t_2$ is selected, such that the ultrasound 32 completely spans the width of the volume of non-interest 16 when the pulse of ultrasound 32 completely exits the volume of interest 14 at time $t_3$, at which time the pulse of sample light 40 is delivered to the scattering medium 12 as illustrated in FIG. 17c.

Because the speed of light is many orders greater than the speed of ultrasound, the second sample light portion 40b will, in effect, pass through the volume of non-interest 16 before the pulse of ultrasound 32 exits the volume of non-interest 16. Thus, at time $t_2$, the optical masking zone 13 resulting from the ultrasound 32 will be confined within the volume of non-interest 16. As such, the first sample light portion 40a, which does not pass through the optical masking zone 13, will exit the scattering medium 12 as signal light 44 that is not affected by the ultrasound 32, and thus, will be correlated with the holographic beat component of the interference light pattern 48, whereas the second sample light portion 40b, which passes through the optical masking zone 13, will exit the scattering medium 12 as background light 46 that will be affected by the ultrasound 32, and thus, will be decorrelated from the holographic beat component of the interference light pattern 48.

It should be appreciated that in the case where the ultrasound 32 is PW, the pulse of sample light 40 may only be applied when no portion of the ultrasound 32 is disposed within the volume of interest 14, thus confining the optical masking zone 13 within the volume of non-interest 16 at the beginning of the measurement period, the ultrasound 32 may slightly transgress into the volume of the interest by the end of the measurement period. For example, if the duration of the measurement period (i.e., in this case the duration of the pulse of sample light 40) is on the order of one microsecond, then the ultrasound 32 will travel about 1.5 millimeters, resulting in the blurring of the detected signal light 44 within the holographic beat component of the interference light pattern 48. Thus, the optical masking zone 13 may not have a sharp edge during the duration of the measurement period.

The optical detection system 10 may conveniently be configured for detecting different volumes of interest 14 simply by varying the frequency of the ultrasound 32 if delivered in a CW mode or varying the timing of the pulses of ultrasound 32 and sample light 40 if the ultrasound 32 is delivered in the PW mode. For example, in the context of detecting neural activity within the brain, the shallow neural areas of the brain (which would be a first volume of interest) could be detected, while masking the light in the scalp and skull (as a first volume of non-interest) during a first measurement period; then deeper neural areas of the brain (which would be a second volume of interest of interest), while masking the light in the scalp and skull, as well as the light in the shallower neural areas of the brain (as a second volume of non-interest); and so forth.

Figure 18A:
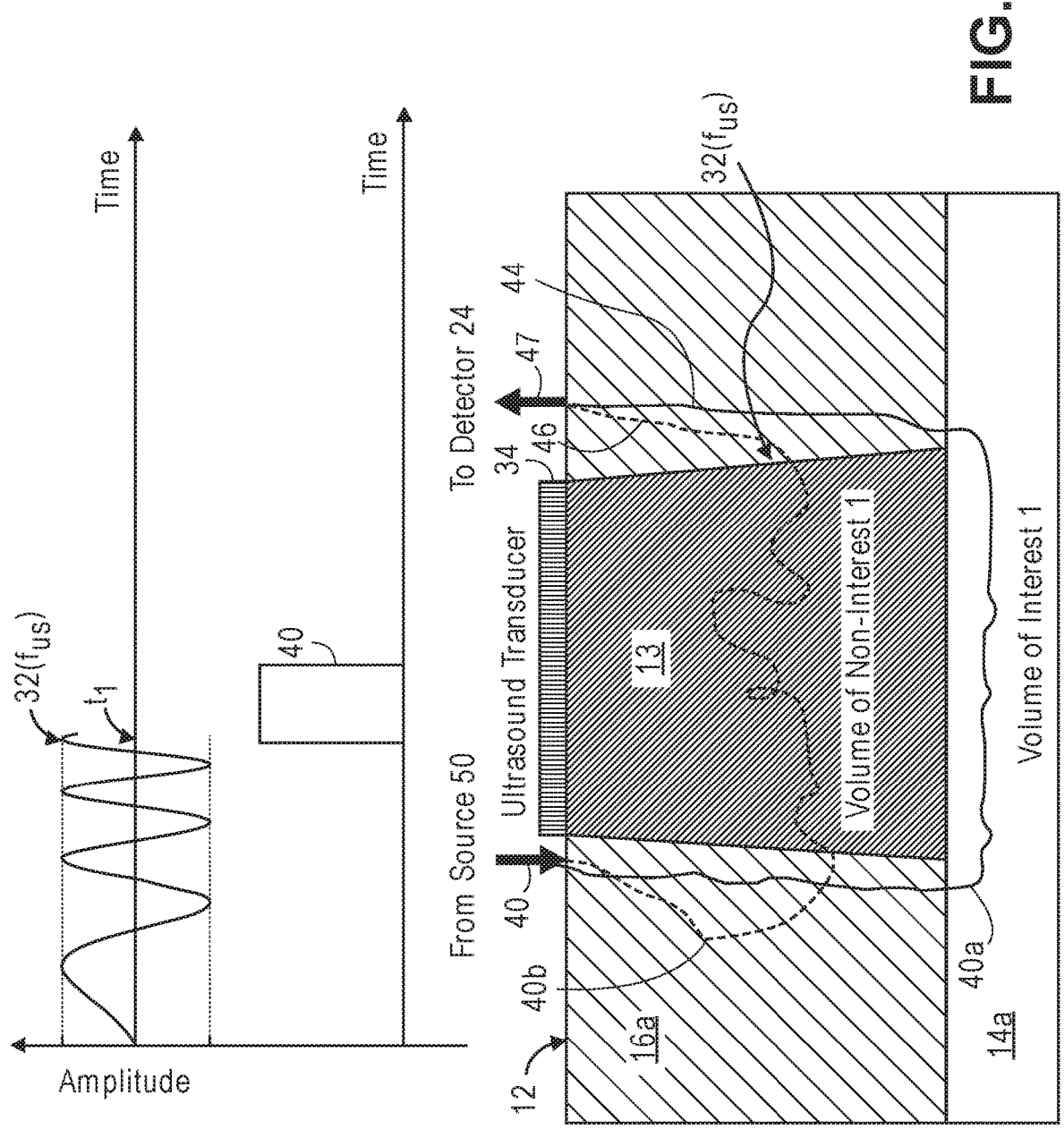
Figure 18B:
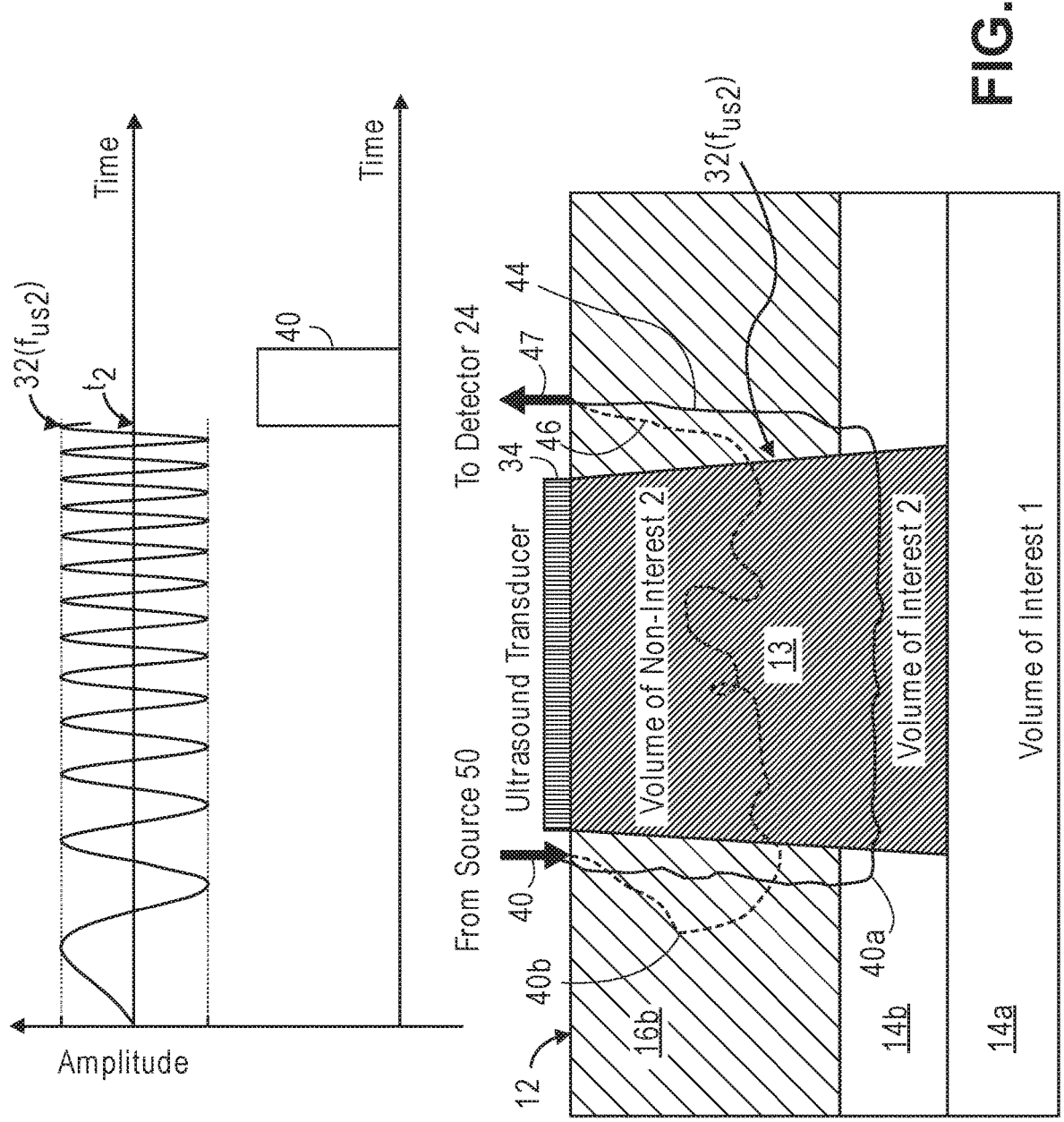

For example, referring first to FIG. 18*a*-18*c*, the ultrasound 32, when delivered in the CW mode, can be swept from a relatively low frequency $f_{us1}$ at time $t_1$ (see FIG. 18*a*), to a relatively medial frequency $f_{us2}$ at time $t_2$ (see FIG. 18*b*), to a relatively high frequency $f_{us3}$ at time $t_3$ (see FIG. 18*c*). Of course, instead of sweeping, the ultrasound 32 may alternatively be discretely changed between the low frequency $f_{us1}$t, medial frequency $f_{us2}$, and high frequency $f_{us3}$.

At the low frequency $f_{us1}$, the ultrasound 32 penetrates at deeper depths into the scattering medium 12 through a first relatively thick volume of non-interest 16*a* without substantially passing into a relatively deep first volume of interest 14*a* (see FIG. 18*a*). In this manner, the second sample light portion 40*b*, which passes through the first volume of non-interest 16*a*, exits the scattering medium 12 as background light 46 that will be decorrelated from the holographic beat component of the interference light pattern 48, while the first sample light portion 40*a*, which passes through the first volume of interest 14*a*, exits the scattering medium 12 as background light 46 that will be decorrelated from the holographic beat component of the interference light pattern 48.

At the medial frequency $f_{us2}$, the ultrasound 32 penetrates shallower into the scattering medium 12 through a less thick second volume of non-interest 16*b* without substantially passing into a shallower second volume of interest 14*b* (see FIG. 18*b*). In this manner, the second sample light portion 40*b*, which passes through the second volume of non-interest 16*b*, exits the scattering medium 12 as background light 46 that will be decorrelated from the holographic beat component of the interference light pattern 48, while the first sample light portion 40*a*, which passes through the second volume of interest 14*b*, exits the scattering medium 12 as background light 46 that will be decorrelated from the holographic beat component of the interference light pattern 48.

At the high frequency $f_{us3}$, the ultrasound 32 penetrates even less deep into the scattering medium 12 through an even less thick third volume of non-interest 16*c* without substantially passing into a third volume of interest 14*c* (see FIG. 18*c*). In this manner, the second sample light portion 40*b*, which passes through the third volume of non-interest 16*c*, exits the scattering medium 12 as background light 46 that will be decorrelated from the holographic beat component of the interference light pattern 48, while the first sample light portion 40*a*, which passes through the third volume of interest 14*c*, exits the scattering medium 12 as background light 46 that will be decorrelated from the holographic beat component of the interference light pattern 48.

Thus, it can be appreciated that, in this manner, the scattering medium 12 can be progressively detected from a greater depth to a shallower depth. Of course, the ultrasound 32 can be swept to a relatively high frequency $f_{us3}$, to a relatively medial frequency $f_{us2}$, to a relatively low frequency $f_{us3}$, such that the scattering medium 12 can be progressively detected from a shallower depth to a greater depth. Alternatively, the ultrasound 32 may alternatively be discretely changed between the low frequency $f_{us1}$, medial frequency $f_{us2}$, and high frequency $f_{us3}$ in any order.

Figure 19A:
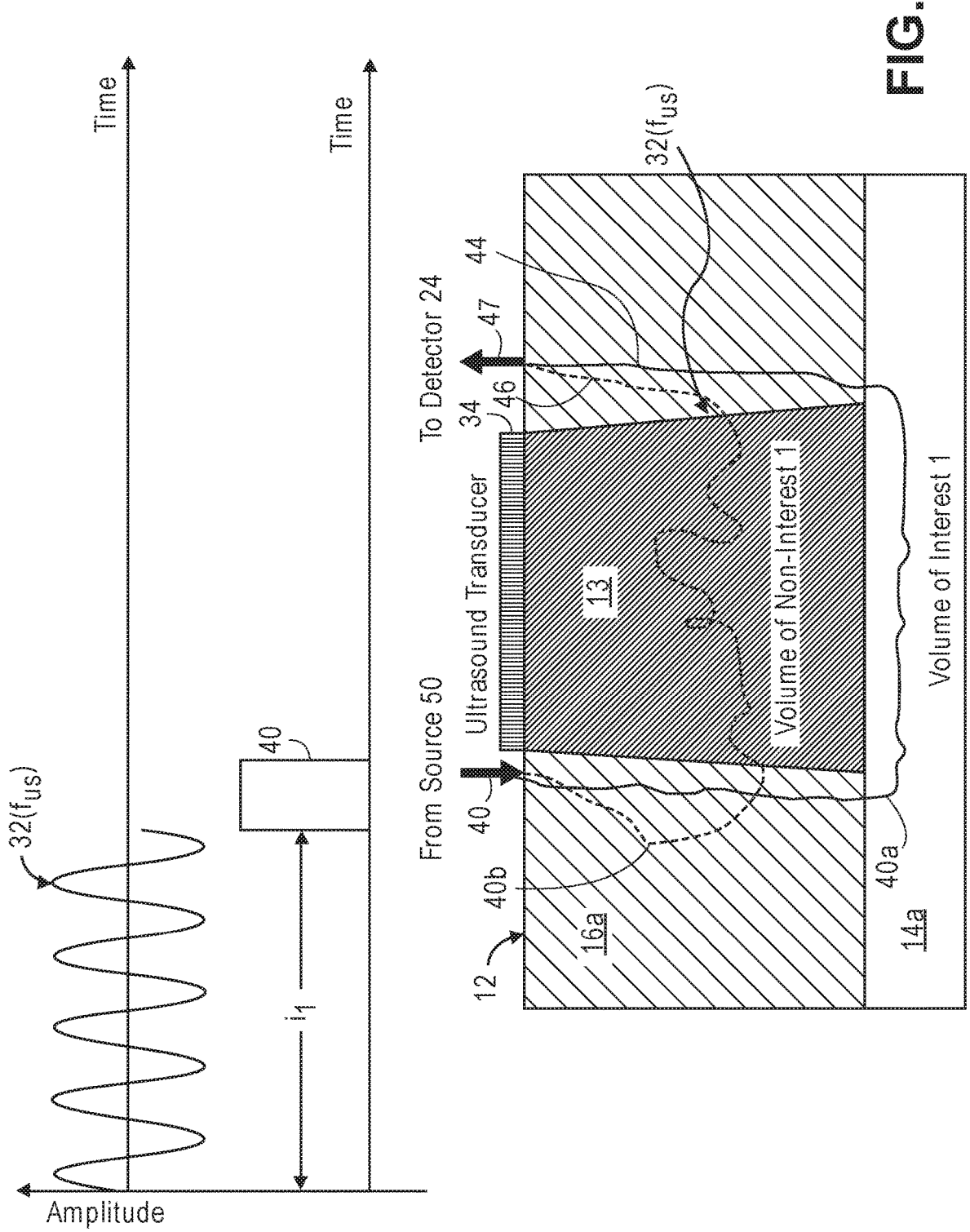
FIGS. 19a-19c are diagrams illustrating yet another exemplary technique used by the optical detection system of FIG. 6 to confine an optical masking zone created by PW ultrasound with multiple volumes of non-interest.
Figure 19B:
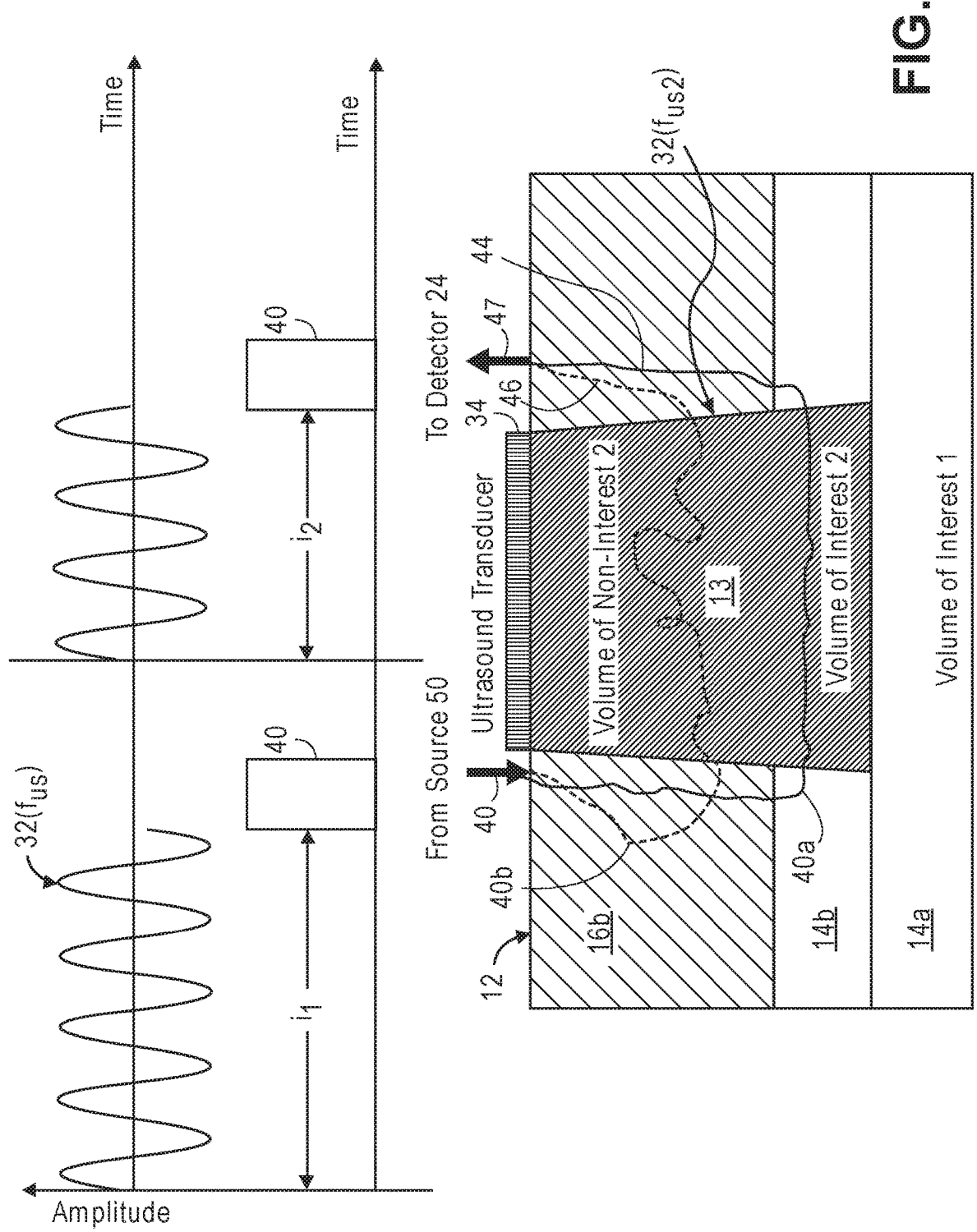
Figure 19C:
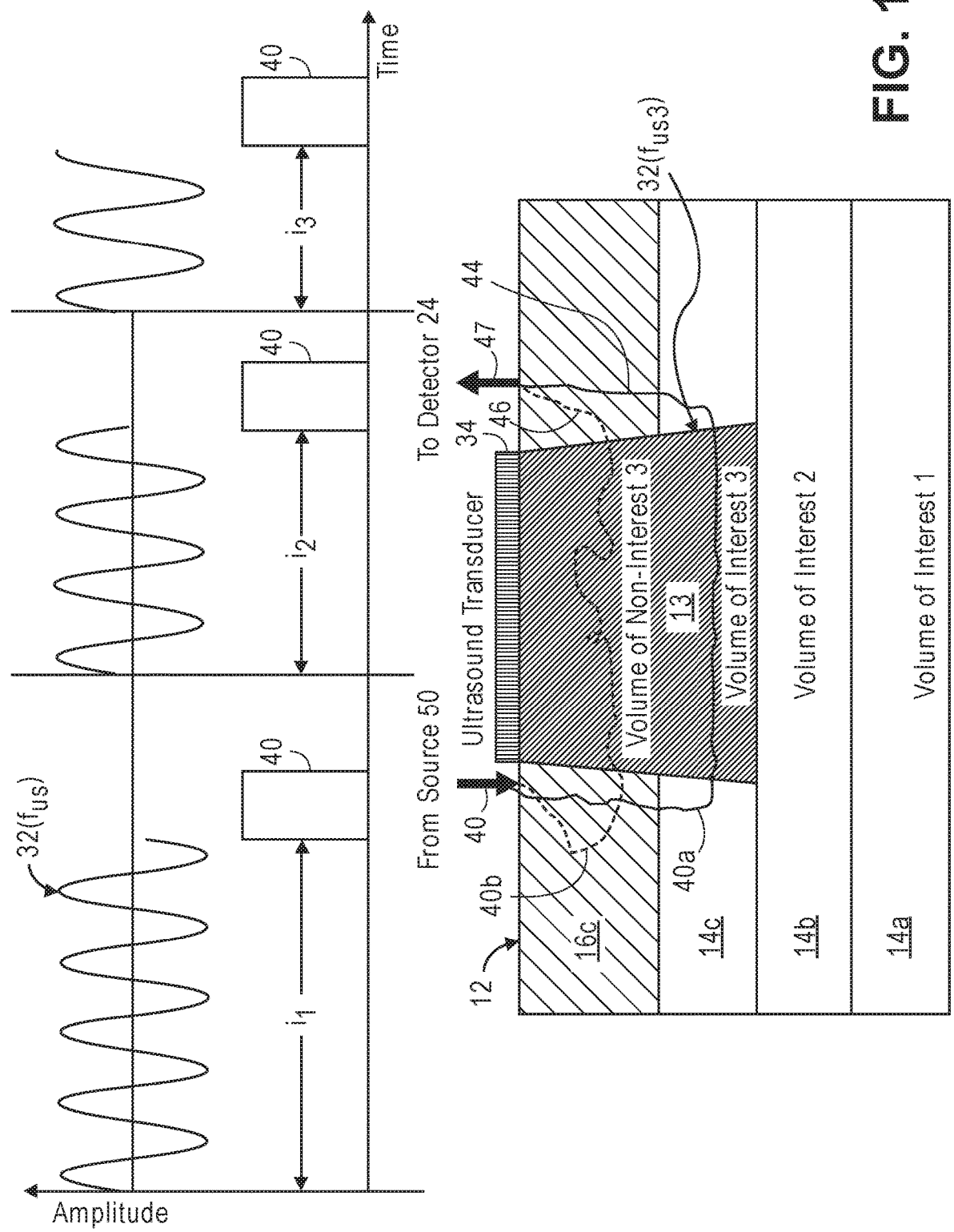
Figure 20:
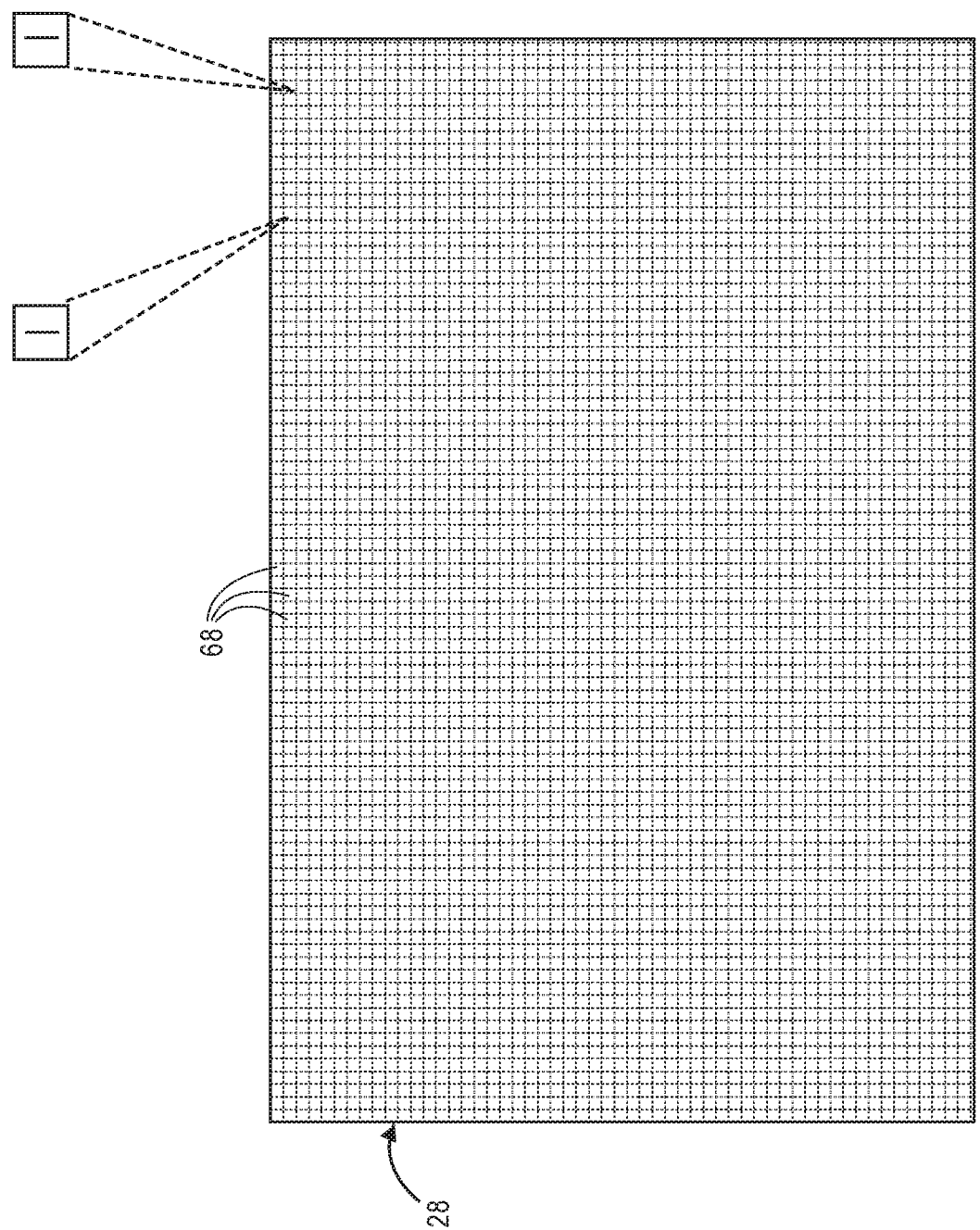
FIG. 20 is a schematic diagram of one embodiment of a detector array used in the optical detection system of FIG. 6.

As another example, referring first to FIG. 19*a*-19*c*, the timing of the pulse of sample light 40 and the pulse of the ultrasound 32, when delivered in the PW mode, can be decreased from a relatively long time interval $i_3$ between the beginning of the pulse of ultrasound 32 and the beginning of the pulse of sample light 40, to a relatively medial time interval $i_2$ between the beginning of the pulse of ultrasound 32 and the beginning of the pulse of sample light 40, to a relatively short time interval between the beginning of the pulse of ultrasound 32 and the beginning of the pulse of sample light 40.

When there is a long interval the pulse of ultrasound 32 penetrates deeper into the scattering medium 12 through a relatively thick first volume of non-interest 16*a* before the pulse of sample light 40 is subsequently delivered to the relatively deep first volume of interest 14*a* (see FIG. 19*a*). In this manner, the second sample light portion 40*b*, which passes through the first volume of non-interest 16*a*, exits the scattering medium 12 as background light 46 that will be decorrelated from the holographic beat component of the interference light pattern 48, while the first sample light portion 40*a*, which passes through the first volume of interest 14*a*, exits the scattering medium 12 as background light 46 that will be decorrelated from the holographic beat component of the interference light pattern 48.

When there is medial interval $i_2$, the pulse ultrasound 32 penetrates shallower into the scattering medium 12 through a less thick second volume of non-interest 16*b* before the pulse of sample light 40 is subsequently delivered to the shallower second volume of interest 14*b* (see FIG. 19*b*). In this manner, the second sample light portion 40*b*, which passes through the second volume of non-interest 16*a*, exits the scattering medium 12 as background light 46 that will be decorrelated from the holographic beat component of the interference light pattern 48, while the first sample light portion 40*a*, which passes through the second volume of interest 14*b*, exits the scattering medium 12 as background light 46 that will be decorrelated from the holographic beat component of the interference light pattern 48.

When there is short interval $i_3$, the pulse of ultrasound 32 penetrates even shallower into the scattering medium 12 through an even less thick third volume of non-interest 16*c* before the pulse of sample light 40 is subsequently delivered to the even shallower third volume of interest 14*c* (see FIG. 19*c*). In this manner, the second sample light portion 40*b*, which passes through the third volume of non-interest 16*c*, exits the scattering medium 12 as background light 46 that will be decorrelated from the holographic beat component of the interference light pattern 48, while the first sample light portion 40*a*, which passes through the third volume of interest 14*c*, exits the scattering medium 12 as background light 46 that will be decorrelated from the holographic beat component of the interference light pattern 48.

Thus, it can be appreciated that, in this manner, the scattering medium 12 can be progressively detected from a greater depth to a shallower depth. Of course, the timing of the pulse of sample light 40 and the pulse of the ultrasound 32 can be increased from a relatively short time interval $i_3$ between the beginning of the pulse of ultrasound 32 and the beginning of the pulse of sample light 40, to a relatively medial time interval $i_2$ between the beginning of the pulse of ultrasound 32 and the beginning of the pulse of sample light 40, to a relatively long time interval between the beginning of the pulse of ultrasound 32 and the beginning of the pulse of sample light 40, such that the scattering medium 12 can be progressively detected from a shallower depth to a greater depth. Alternatively, the time intervals $i_1$, $i_2$, and $i_3$ can be applied to the timing between the pulses of ultrasound 32 and the pulses of sample light 40 in any order to detect the depths of the scattering medium 12 in any order.

Referring back to FIG. 6, the optical detector 24 may comprise a pixel array (as in a camera), a single photodiode, a photodiode array, or other optical detectors, and may, e.g., take the form of a charged couple device (CCD) camera, or similar commercial-type image sensors, such as complementary metal-oxide-semiconductor (CMOS) sensor, photodiode (PD) array, avalanche photodiode (APD) array, single photon avalanche diode (SPAD) detector, time-of-flight (ToF) imaging camera, indium gallium arsenide (In-GaAs) sensor, etc. The optical detector 24 may be a completely integrated device or may be arranged on closely spaced multiple devices or device regions. In the embodiment illustrated in FIG. 20, the optical detector 24 includes an array of pixels 68, which are configured for simultaneously detecting the spatial components of the interference light pattern 48 (shown in FIG. 7). In the case where the interference light pattern 48 is a speckle light pattern, the spatial components are speckle grains (approximately the size of a wavelength of the light) of the speckle light pattern. Each pixel 68 of the optical detector 24 stores an intensity value I of a respective spatial component of the interference light pattern 48. The optical detector 24 includes control inputs (not shown) for receiving control signals from the controller 26, such that detection of the intensity values can be coordinated with the delivery of the sample light 40 described in further detail below.

Although not illustrated, the optical detection system 10 may include magnification optics and/or apertures to magnify the individual speckle grains, which may have a size on the order of the wavelength of the near-infrared or visible light used to acquire the data, and hence on the order of hundreds of nanometers in size, to approximately the sizes of the pixels 68 of the optical detector array 24. Thus, in the illustrated embodiment, the pixel sizes and pitches of the optical detector array 24 are matched to the speckle grain sizes and pitches of the speckle light pattern 48 via the appropriate magnification, although other embodiments are possible.

Figure 21:
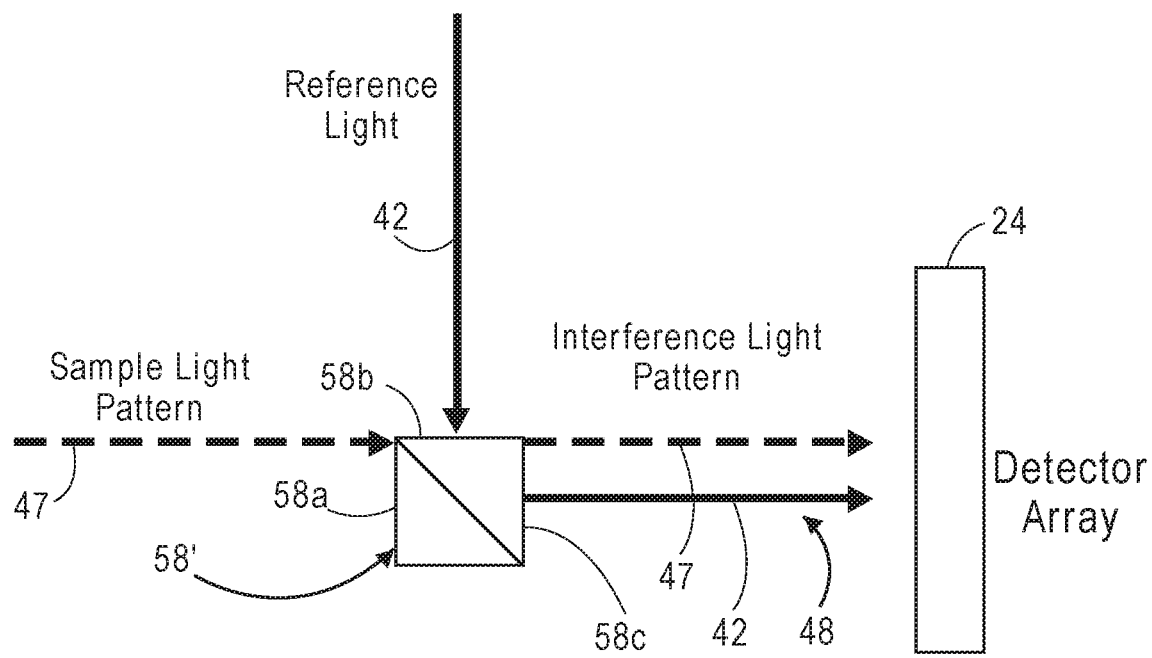
FIG. 21 is a block diagram of one specific embodiment of an optical beam combiner of an interferometer and detector array that can be used in the optical detection system of FIG. 6.
Figure 22:
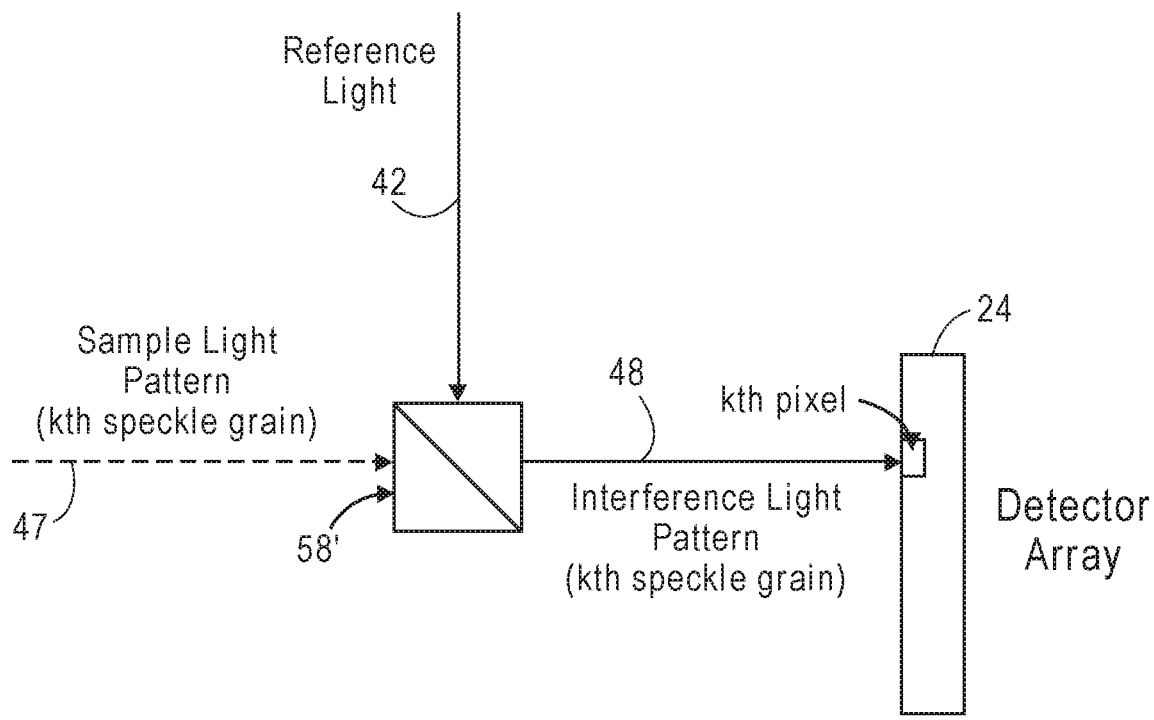
FIG. 22 is a block diagram of the optical beam combiner of an interferometer and detector array of FIG. 21, particularly showing the generation and detection of a kth speckle grain of an interference light pattern.

As briefly discussed above, the interferometer 20 may generate a single interference light pattern 48 during each measurement period, in which case, only a single detector array 24 (e.g., a single camera) is needed to detect the interference light pattern 48. For example, as illustrated in FIG. 21, an optical beam combiner 58' (which replaces the optical beam splitter/combiner 58 illustrated in FIG. 7) is configured for combining the sample light pattern 47 and the reference light 42 to generate a single interference light pattern 48. That is, the optical beam combiner 58' transmits the sample light pattern 47 and reflects the reference light 42, wherein they interfere to generate the interference light pattern 48. As illustrated in FIG. 22, each kth speckle of the interference light pattern 48 corresponds to a kth pixel 68 of the optical detector array 24. That is, a spatial component of the sample light pattern 47 (i.e., the kth speckle grain of the speckle light field) interferes with the reference light 42 to generate a kth speckle grain of the interference light pattern 48 that is detected by kth pixel of the optical detector array 24. It should be appreciated that although FIG. 22 illustrates one speckle grain "k," an equivalent process for measuring the speckle grain k takes place for all speckles grains in parallel in the manner of imaging an entire speckle light field.

In the case where a single detector array 24 is used, it may be desirable to incorporate pre-selected phase shifts or offsets between the sample arm and reference arm of the interferometer 20 (e.g., two phase shifts or offsets 0, $\pi$, or four phase shifts or offsets 0, $\pi$, $\pi/2$, $3\pi/2$), such that multiple phase-modulated interference light patterns 48 are sequentially generated over multiple measurement periods, which interference light patterns 48 would then be processed to detect the optical parameter in the volume of interest 14. In this case, it is preferable that the interferometer 20 cycle through the entire set of pre-selected shifts or offsets over a time interval that is quicker than the decorrelation time of the desired detected depth in the scattering medium 12.

Pre-selected phase shifts or offsets between the sample arm and reference arm of the interferometer 20 can be implemented by, e.g., incorporating a controllable optical phase shifter in the sample arm or reference arm of the interferometer 20, as described in U.S. patent application Ser. No. 15/844,370, entitled "Pulsed Ultrasound Modulated Optical Tomography Using Lock-In Camera," which is expressly incorporated herein by reference. The single detector array 24 may, e.g., comprise a conventional CCD camera or may be an optical lock-in camera arrangement, such as those described in U.S. patent application Ser. No. 15/844,370 and U.S. patent application Ser. No. 15/853,538, entitled "Systems and Methods for Quasi-Ballistic Photon Optical Coherence Tomography in Diffusive Scattering Media Using a Lock-In Camera Detection" (now U.S. patent Ser. No. 10,219,700), which is expressly incorporated herein by reference.

As briefly discussed above, the interferometer 20 may concurrently generate multiple phase-modulated interference light patterns 48 during each measurement period, in which case, multiple detector arrays 24 (e.g., multiple cameras or dedicated spatial regions of a single camera), and in this case, two detector arrays 24a, 24b are used, as illustrated in FIG. 24. The two detector arrays 24a and 24b are optically registered with each other to concurrently detect the two interference light patterns 48a and 48b over two phases. In this manner, two separate measurements of the volume of interest 14 can be made simultaneously or in short succession by measuring the interference between the sample light pattern 47 and reference light 42 at two separate phases differing from each other by an angular phase of $\pi$. Thus, the required phase-modulated interference light patterns 48a and 48b may be more easily generated within the speckle decorrelation time of the scattering medium 12.

An optical beam splitter/combiner 58" (which replaces the optical beam splitter/combiner 58 illustrated in FIG. 7) is configured for splitting the reference light 42 respectively into reference light 42a, 42b respectively having two different phases of 0 and $\pi$), splitting the sample light pattern 47 respectively into sample light patterns 47a and 47b, and concurrently combining the sample light patterns 47a and 47b with the reference light 42a and 42b to respectively generate two interference light patterns 48a ("Interference Light Pattern A"), 48b ("Interference Light Pattern B").

That is, the sample light pattern 47 enters an input port 58a of the optical beam splitter/combiner 58", where it is split into a reflected sample light pattern 47a and a transmitted sample light pattern 47b, and the reference light 42 enters another input port 58b of the optical beam splitter/combiner 58", where it is split into a transmitted reference light 42a and a reflected reference light 42b. In a simultaneous manner, the reflected sample light pattern 47a interferes with the transmitted reference light 42a to generate the interference light pattern 48a, and the transmitted sample light pattern 47b interferes with the reflected reference light 42b to generate the interference light pattern 48b.

Due to power conservation, a four-port network, such as the optical beam splitter/combiner 58", requires the total power entering the input ports 58a, 58b to be equal to the total power exiting the output ports 58c, 58d, and thus, the transmitted reference light 42a will have a nominal phase of 0, and the reflected reference light 42b will have a phase of $\pi$. That is, as will be described in further detail below, since the combined power of the DC terms of the interference light patterns 48a, 48b exiting the respective output ports 58a, 58b of the optical beam splitter/combiner 58" will be equal to the combined power of combined DC power of the sample light pattern 47 and reference light 42 respectively entering the input ports 58a, 58b of the optical beam splitter/combiner 58", the interfering AC beat pattern terms of the respective interference light patterns 48a, 48b will need to differ in phase by 180 degrees such that they sum to zero.

The optical detector array 24a and detector array 24b are respectively disposed at two output ports 58c, 58d of the optical beam splitter/combiner 58" for concurrently detecting the respective two interference light patterns 48a, 48b, and generating two pluralities of values representative of intensities of the spatial components ("speckle grains") of the respective two interference light patterns 48a, 48b. Thus, the sample light pattern 47 and reference light 42 combine to project an interference light pattern 48a onto the optical detector array 24a, and likewise to project an interference light pattern 48b onto the optical detector array 24b, but with respect to a different phase of the reference light 42. In the illustrated embodiment, the planes of the optical detector arrays 24a, 24b are perpendicular to each other, such that they face the respective output ports 58c, 58d of the optical beam splitter/combiner 58". The optical detector arrays 24a, 24b may be conventional in nature (e.g., readily available conventional charge-coupled device (CCD) cameras and may take the form of e.g., similar commercial-type image sensors, such as complementary metal-oxide-semiconductor (CMOS) sensor, photodiode (PD) array, avalanche photodiode (APD) array, single photon avalanche diode (SPAD) detector, time-of-flight (ToF) imaging camera, indium gallium arsenide (InGaAs) sensor, etc.

Although the optical detector arrays 24a, 24b are separate and distinct, the optical detector arrays 24a, 24b are optically aligned with each other, such that any given pixels on the optical detector arrays 24a, 24b have a known one-to-one correspondence with each other. That is, as illustrated in FIG. 24, a spatial component of the sample light pattern 47 (i.e., the kth speckle grain of the speckle light field) interferes with the reference light 42 with no phase shift (i.e., 0) to generate a kth speckle grain of the interference light pattern 48a that is detected by kth pixel of the optical detector array 24a, and the same kth speckle grain of the sample light pattern 47 interferes with the reference light 42 with a phase shift (i.e., $\pi$) to generate a corresponding kth speckle grain of the interference light pattern 48b that is detected by the corresponding kth pixel of the optical detector array 24b. Since the kth pixel of the optical detector array 24a has a known correspondence via optical alignment with the kth pixel of the optical detector array 24b, the pair of intensity values detected by the kth pixels of the optical detector arrays 24a, 24b are both representative of the kth speckle grain of the sample light pattern 47, but at different phases. It should be appreciated that although FIG. 24 illustrates one speckle grain "k," an equivalent process for measuring the speckle grain k takes place for all speckle grains in parallel in the manner of imaging an entire speckle light field.

At each corresponding pair of kth pixels, the optical power received by the respective detector arrays 24a, 24b is equal to the summation of the power of the reference light 42 ($P_{reference}A$ and $P_{reference}B$) input into the optical beam splitter/combiner 58", the sample light pattern 47 ($P_{sample}A$ and $P_{sample}B$) input into the optical beam splitter/combiner 58", and an interference term between the reference light 42 and sample light pattern 47 ($P_{interfere}A$ and $P_{interfere}B$). By the power conservation, the interference terms $P_{interfere}A$ and $P_{interfere}B$ are 180 degrees out of phase for the optical detector arrays 24a, 24b.

Although two distinct detector arrays 24a, 24b have been described, two distinct camera regions on a single camera can be used for detecting the two interference light patterns 48a, 48b. Furthermore, although the optical detector arrangement illustrated in FIGS. 23 and 24 only generates two phase-modulated interference light patterns 48 (0, $\pi$), alternative detector arrangements that generate more phase-modulated interference light patterns 48, e.g., four phase-modulated interference light patterns 48 (0, $\pi/2$, $\pi$, $3\pi/2$), can be used. Further details discussing different systems for simultaneously detecting an M number of interference light patterns are described in U.S. patent application Ser. No. 15/853,209, entitled "System and Method for Simultaneously Detecting Phase Modulated Optical Signals" (now U.S. Pat. No. 10,016,137), which is expressly incorporated herein by reference.

Referring back to FIG. 6, the controller 26 is configured for sending control signals to the signal generator 32 of the acoustic assembly 22 to control the amplitude, frequency, phase, and duration of the ultrasound 30, and further for sending control signals to the drive circuit of the optical source 50 of the interferometer 20 to control the amplitude, duration, and if relevant, the pulsing of the sample light 40. Preferably, the controller 26 operates the interferometer 20 in a pulsed wave (PW) mode, so that more energy can be packed into the pulses of sample light 40 to improve the signal-to-noise ratio. The controller 26 may operate the acoustic assembly 22 in either a continuous wave (CW) or a pulsed wave (PW) mode, as described in further detail below. The controller 26 is further configured for operating the optical detector 22, such it detects the resulting interference light pattern 48 during the measurement period in coordination with the pulsed sample light 40. The controller 26 may also be configured for sending control signals to the path length adjustment mechanism 60 to adjust the optical path length of the reference arm, and control signals to the optical detector 24 to coordinate detection of the interference light pattern 48 with the delivery of the sample light 40 into the scattering medium 12, and in the case where the optical system is an OCT system, to adjust the optical path length of the reference arm for path length selection of the signal light 44.

The processor 28 is configured for extracting the holographic beat component from the interference light pattern 48 detected by the optical detector 24, and determining the optical parameter of the volume of interest 14 based on the extracted holographic beat component of the interference light pattern 48. The specific optical parameter determined by the processor 28 depends on the particular application of the optical detection system 10. For example, if the optical detection system 10 is to be used for detecting neural activity, as briefly discussed above, the optical parameter may be a physiologically-dependent optical parameter.

The physiologically-dependent optical parameter detected by the anatomical detection system can be, e.g., a level of deoxygenated and/or oxygenated hemoglobin concentration in the brain, or the relative abundance or the level of water concentration, or relative water concentration in the brain. In other embodiments, the physiologically-dependent optical parameter can be any parameter that varies in accordance with a change in an optical property of the brain (e.g., light absorption), an analyte concentration in the blood, analyte/metabolite in tissue, concentration of a substance (e.g., blood, hemoglobin) or a structure within tissue, the presence and concentration of lamellar bodies in amniotic fluid for determining the level of lung maturity of a fetus, the presence and/or concentration of meconium in the amniotic fluid, optical properties of other extravascular fluids, such as pleural, pericardial, peritoneal, and synovial fluids. In alternative embodiments, the physiologically-dependent optical parameter detected by the anatomical detection system may be a fast-optical signal (i.e., perturbations in the optical properties of neural tissue caused by mechanisms related to the depolarization of neural tissue, including, but not limited to, cell swelling, cell volume change, changes in membrane potential, changes in membrane geometry, ion redistribution, birefringence changes, etc.). The processor 28 may perform post-processing on the determined optical parameter to generate additional information on the volume of interest 14. For example, the processor 28 may determine a level of neural activity within the brain based on the detected physiologically-dependent optical parameter.

Although the controller 26 and processor 28 are described herein as being separate components, it should be appreciated that portions or all functionality of the controller 26 and processor 28 may be performed by a single computing device. Furthermore, although all of the functionality of the controller 26 is described herein as being performed by a single device, and likewise all of the functionality of the processor 28 is described herein as being performed by a single device, such functionality each of the controller 26 and the processor 28 may be distributed amongst several computing devices. Moreover, it should be appreciated that those skill in the art are familiar with the terms "controller" and "processor," and that they may be implemented in software, firmware, hardware, or any suitable combination thereof.

Decorrelation of the background light 46 from the time-varying temporal interference component of the interference light pattern 48 will now be described in further detail.

Assuming homodyne combination of the signal light 44 and the reference light 42 (i.e., the signal light 44 and reference light 42 have the same frequency), and further assuming, for purposes of simplicity, that the sample light 40 is a rectangular pulse having a duration equal to the measurement period, the intensity of the interference light pattern 48 detected at the optical detector 24 (or each pixel of the optical detector 24), can be expressed as:

$$\text{Intensity} = \int_0^{T_{op}}(P_{reference}(t) + P_{signal}(t) + P_{background}(t) + 2\sqrt{P_{signal}(t) \times P_{reference}(t)} \times (\sin(\emptyset_{unknown})) + 2\sqrt{P_{background}(t) \times P_{reference}(t)} \times (\sin(\theta_{unknown} - (2\pi f_{us})t))) \, dt, tm \quad [4]$$

where $P_{reference}$ represents the reference light 42 as a function of time t, $P_{signal}$ represents the signal light 44 as a function of time t, $P_{background}$ represents the background light 46 as a function of time t, $t_0$ is the beginning of the measurement period, $t_1$ is the end of the measurement period, $\phi_{unknown}$ and $\theta_{unknown}$ are random phases of the respective signal light 44 and background light 46 in the interference light pattern 48 at the time of measurement, which originates via multiple scattering of coherent light inside the tissue, $f_{us}$ is the frequency of the ultrasound 32, and $T_{op}$ is the duration the pulse of sample light 40.

Over the duration of the measurement period, equation [4] integrates to:

$$\text{Intensity} = T_{op}(P_{reference} + P_{signal} + P_{background} + 2\sqrt{P_{signal} \times P_{reference}} \times (\cos(\emptyset_{unknown})) + 2\sqrt{P_{background} \times P_{reference}}/2\pi f_{us} \times (\cos(\theta_{unknown} - (2\pi f_{us})T_{op}) - \cos(\theta_{unknown})) \quad [5]$$

The holographic beat component in equation [5] is represented by:

$$T_{op}(2\sqrt{P_{signal} \times P_{reference}} \times (\cos(\emptyset_{unknown})) + 2\sqrt{P_{background} \times P_{reference}}/2\pi f_{us} \times (\cos(\theta_{unknown} - (2\pi f_{us})T_{op}) - \cos(\theta_{unknown})). \quad [6]$$

Instead of having a constant angle in the cosine function in the background term $2\sqrt{P_{background} \times P_{reference}}/2\pi f_{us} \times (\cos(\theta_{unknown} - (2\pi f_{us})T_{op}) - \cos(\theta_{unknown}))$, the presence of the ultrasound frequency $f_{us}$ in the cosine function creates a non-zero (indeed, rapid) speed of angular rotation of the cosine function with time, such that the cosine function in the signal term $2\sqrt{P_{signal} \times P_{reference}} \times (\cos(\emptyset_{unknown}))$ dominates equation [6], and the background term of equation [6] essentially reduces to zero, thereby decorrelating the background light 46 from the holographic beat component of equation [6]. That is, such decorrelation includes Raman-Nath and moving scattering center mechanisms that generates random, pseudo-random, or periodic phase compared to shifts to the reference light 42, such that the background light 46 is masked from the detected optical parameter of the volume of interest 14 over time. Consistent with the discussion above with respect to FIG. 12, as the ultrasound frequency $f_{us}$ increases, decorrelation of the background light 46 from the holographic beat component of equation [6] likewise increases.

Thus, equation [6] essentially reduces to:

$$T_{op}(2\sqrt{P_{signal} \times P_{reference}}(\cos(\emptyset_{unknown}))), \quad [7]$$

which represents the exclusive contribution of the signal light 44 to the holographic beat component of the interference light pattern 48.

It should also be appreciated that because the DC components in equation [5] (i.e., $P_{reference}$, $P_{signal}$, and $P_{background}$) are constant across the two detector arrays 24a, 24b, they can be eliminated by creating multiple phase-modulated interference light patterns 48; for example, in the case of a single detector array 24, incorporating the pre-selected phase shifts or offsets between the sample arm and reference arm of the interferometer 20, such that multiple phase-modulated interference light patterns 48 are sequentially generated over multiple measurement periods, as illustrated in FIGS. 21 and 22, or in the case of multiple optically registering detector arrays 24, concurrently combining the reference light 42 and sample light pattern 47 into the phase-modulated interference light patterns 48, as illustrated in FIGS. 23 and 24. For example, if two phase-modulated interference light patterns 48 are created, the intensities of these interference light patterns 48, which are out of phase relative to each other by 180 degrees, can be subtracted from each other to eliminate the DC components.

Alternatively, assuming a heterodyne combination of the signal light 44 and the reference light 42 (i.e., the signal light 44 and reference light 42 have different frequencies), and further assuming, for purposes of simplicity, that the sample light 40 is a rectangular pulse that last the duration of the measurement period, the intensity of the interference light pattern 48 detected at the optical detector 24 (or each pixel of the optical detector 24), can be expressed as:

$$\text{Intensity} = \int_0^{T_{op}} (P_{reference}(t) + P_{signal}(t) + P_{background}(t) + 2\sqrt{P_{signal}(t) \times P_{reference}(t)} \times (\sin(\varnothing_{unknown} - (2\pi f_{shift})t)) + 2\sqrt{P_{background}(t) \times P_{reference}(t)} \times (\sin(\theta_{unknown} - (2\pi f_{shift} + 2\pi f_{us})t))) dt, \quad [8]$$

where $P_{reference}$ represents the reference light 42 as a function of time t, $P_{signal}$ represents the signal light 44 as a function of time t, $P_{background}$ represents the background light 46 as a function of time t, $t_0$ is the beginning of the measurement period, $t_1$ is the end of the measurement period, $f_{shift}$ is the difference in frequency between the sample light 40 and the reference light 42, $\varphi_{unknown}$ and $\theta_{unknown}$ are random phases of the respective signal light 44 and background light 46 in the interference light pattern 48 at the time of measurement, which originates via multiple scattering of coherent light inside the tissue, $f_{us}$ is the frequency of the ultrasound 32, and $T_{op}$ is the duration the sample light 40.

Over the duration of the measurement period, equation [8] integrates to:

$$\text{Intensity} = T_{op}(P_{reference} + P_{signal} + P_{background} + 2\sqrt{P_{signal} \times P_{reference}}/2\pi f_{shift} \times (\cos(\varnothing_{unknown} + (2\pi f_{shift})T_{op}) - \cos(\varnothing_{unknown})) + 2\sqrt{P_{background} \times P_{reference}}/(2\pi f_{shift} + 2\pi f_{us}) \times (\cos(\theta_{unknown} - (2\pi f_{shift} + 2\pi f_{us})T_{op}) - \cos(\theta_{unknown}))) \quad [9]$$

The holographic beat component in equation [9] is represented by:

$$T_{op}(2\sqrt{P_{signal} \times P_{reference}}/2\pi f_{shift} \times (\cos(\varnothing_{unknown} + (2\pi f_{shift})T_{op}) - \cos(\varnothing_{unknown})) + 2\sqrt{P_{background} \times P_{reference}}/(2\pi f_{shift} + 2\pi f_{us}) \times (\cos(\theta_{unknown} - (2\pi f_{shift} + 2\pi f_{us})T_{op}) - \cos(\theta_{unknown}))). \quad [10]$$

Instead of having a constant angle in the cosine function in the background term $2\sqrt{P_{background} \times P_{reference}}/(2\pi f_{shift} + 2\pi f_{us}) \times (\cos(\theta_{unknown} - (2\pi f_{shift} + 2\pi f_{us})T_{op}) - \cos(\theta_{unknown}))$, the presence of the ultrasound frequency $f_{us}$ in the cosine function creates a non-zero (indeed, rapid) speed of angular rotation of the cosine function with time, such that the cosine function in the signal term $2\sqrt{P_{signal} \times P_{reference}}/2\pi f_{shift} \times (\cos(\varnothing_{unknown} + (2\pi f_{shift})T_{op}) - \cos(\varnothing_{unknown}))$ dominates equation [10], and the background term in equation [10] essentially reduces to zero, thereby decorrelating the background light 46 from the holographic beat component of equation [10]. That is, such decorrelation includes Raman-Nath and moving scattering center mechanisms that generates random, pseudo-random, or periodic phase compared to shifts to the reference light 42, such that the background light 46 is masked from the detected optical parameter of the volume of interest 14 over time.

Again, consistent with the discussion above with respect to FIG. 12, as the ultrasound frequency $f_{us}$ increases, decorrelation of the background light 46 from the holographic beat component of equation [6] likewise increases. Thus, equation [10] essentially reduces to:

$$T_{op}(2\sqrt{P_{signal} \times P_{reference}}/2\pi f_{shift} \times (\cos(\varnothing_{unknown} + (2\pi f_{shift})T_{op}) - \cos(\varnothing_{unknown}))), \quad [11]$$

which represents the exclusive contribution of the signal light 44 to the holographic beat component of the interference light pattern 48.

It should be appreciated that, although the ultrasound frequency $f_{us}$ can be uniform (pure tone) over the measurement period (as illustrated in FIG. 13a), the background term in equations [6] and [10] can be further minimized by varying the ultrasound frequency $f_{us}$ over the measurement period, e.g., by sweeping or randomizing the ultrasound frequency $f_{us}$ (as illustrated in FIG. 13b or FIG. 13c), and even further minimized by varying, in addition to the frequency $f_{us}$, the amplitude and/or phase of the ultrasound (as illustrated in FIG. 13d or FIG. 13e) or completely having a completely arbitrary wave (as illustrated in FIG. 13f).

It should be appreciated that, because the holographic beat component of the interference light pattern 48 varies over time in the case where the reference light 42 and signal light 44 are combined using a homodyne technique, it is preferred that the detector(s) 24 take the form of a lock-in camera, such that a detected intensity value can be instantaneously locked in, as described in U.S. patent application Ser. No. 15/844,370, entitled "Pulsed Ultrasound Modulated Optical Tomography Using Lock-In Camera," which is expressly incorporated herein by reference. This should be contrasted with the homodyne case, where an intensity value is detected over an integration time, such that a lock-in camera is not required. Furthermore, it is preferred that, in the heterodyne case, the intensity values be measured in quadrature, such that the generation of four phase-modulated interference light patterns 48 is required, as described in U.S. patent application Ser. No. 15/844,370, entitled "Pulsed Ultrasound Modulated Optical Tomography Using Lock-In Camera, and U.S. patent application Ser. No. 15/853,209, entitled "System and Method for Simultaneously Detecting Phase Modulated Optical Signals" (now U.S. patent Ser. No. 10,016,137), which are expressly incorporated herein by reference.

Figure 25:
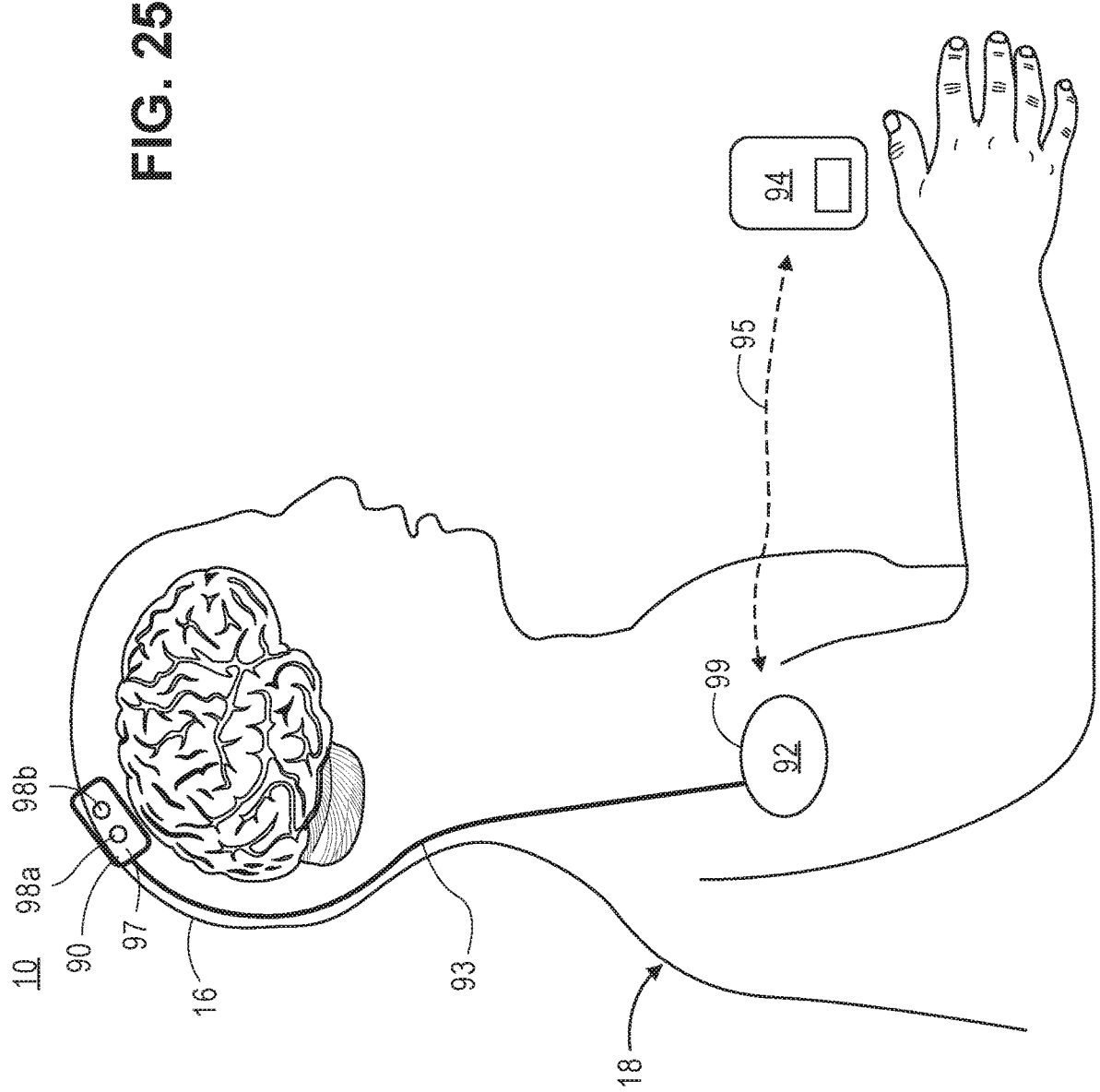
FIG. 25 is a plan view of wearable and unwearable units in which the optical detection system of FIG. 6 may be embodied.

Referring now to FIG. 25, the physical implementation of a non-invasive optical detection system 10 for use in the detection of neural activity within the brain (as the volume of interest 14) through the scalp and skull (as the volume of non-interest 16) of a person 18 will be described. As shown, the optical detection system 10 includes a wearable unit 90 that is configured for being applied to a person 18, and in this case, worn on the head (as the scattering medium 12) of the person 18; an auxiliary head-worn or not head-worn unit 92 (e.g., worn on the neck, shoulders, chest, or arm) coupled to the wearable unit 90 via a wired connection 93 (e.g., electrical wires); and an optional remote processor 94 in communication with the patient-wearable auxiliary unit 92 coupled via a wireless connection 95 (e.g., radio frequency (RF) link). Alternatively, the optical detection system 10 may use a non-wired connection (e.g., an RF link) for providing power to or communicating between the respective wearable unit 90 and the auxiliary unit 92, and/or a wired connection between the auxiliary unit 92 and the remote processor 94.

In the illustrated embodiment, the wearable unit 90 includes a support structure 97 that either contains or carries the interferometer 20, the ultrasound transducer 34 of the acoustic assembly 22, and the optical detector(s) 24 (shown in FIG. 6). The wearable unit 90 may also include an output port 98a from which the sample light 40 generated by the interferometer 20 is emitted (from the optical source 50), and an input port 98b into which the sample light pattern 44 is input into the interferometer 20 (received by the optical detector(s) 24). It should be appreciated that although the input port 98b is illustrated in close proximity to the input port 98a, the proximity between the input port 98b and the output port 98a may be any suitable distance. The support structure 97 may be shaped, e.g., have a banana, headband, cap, helmet, beanie, other hat shape, or other shape adjustable and conformable to the user's head (as the scattering medium 12), such that the ports 98a and 98b are in close contact with the outer skin of the body part, and in this case, the scalp (as the volume of non-interest 16) of the head of the person 18. An index matching fluid maybe used to reduce reflection of the light generated by the optical source 50 of the interferometer 20 from the outer skin of the scalp (as the volume of non-interest 16). An adhesive or belt (not shown) can be used to secure the support structure 94 to the head (as the scattering medium 12) of the person 18. Notably, because the ultrasound 32 emitted by the ultrasound transducer 34 need not be hi-fidelity, and in fact, it is desirable to make the ultrasound 32 as noisy as possible, acoustic coupling between the ultrasound transducer 34 and the scalp of the person 18 can be inefficient, and therefore, a bubble-free liquid ultrasound medium for ensuring that there is sufficient acoustic coupling between the ultrasound transducer 34 and the scalp (as the volume of non-interest 16) is not required.

The auxiliary unit 92 includes a housing 99 that contains the controller 26 and the processor 28 (shown in FIG. 6). In some embodiments, portions of the controller 26 and processor 28 may be integrated within the wearable unit 90. The auxiliary unit 92 may additionally include a power supply (which if head-worn, may take the form of a rechargeable or non-chargeable battery), a control panel with input/output functions, a display, and memory. Alternatively, power may be provided to the auxiliary unit 92 wirelessly (e.g., by induction). The auxiliary unit 92 may further include the signal generator 36 of the acoustic assembly 20, as well as any drive circuitry used to operate the interferometer 20. The remote processor 94 may store detected data from previous sessions, and include a display screen.

The interferometer 20 and detector 24 are preferably mechanically and electrically isolated from the acoustic assembly 22, such that the emission of the ultrasound 32 by the acoustic assembly 22, as well as the generation of RF and other electronic signals by the acoustic assembly 22, minimally affects the detection of the optical signals by the interferometer 20 and generation of data by the optical detector 24. The wearable unit 90 may include shielding (not shown) to prevent electrical interference and appropriate materials that attenuate the propagation of acoustic waves through the support structure 94, although such shielding may not be needed due to the fact that high fidelity ultrasound is not required, as described above.

Figure 26:
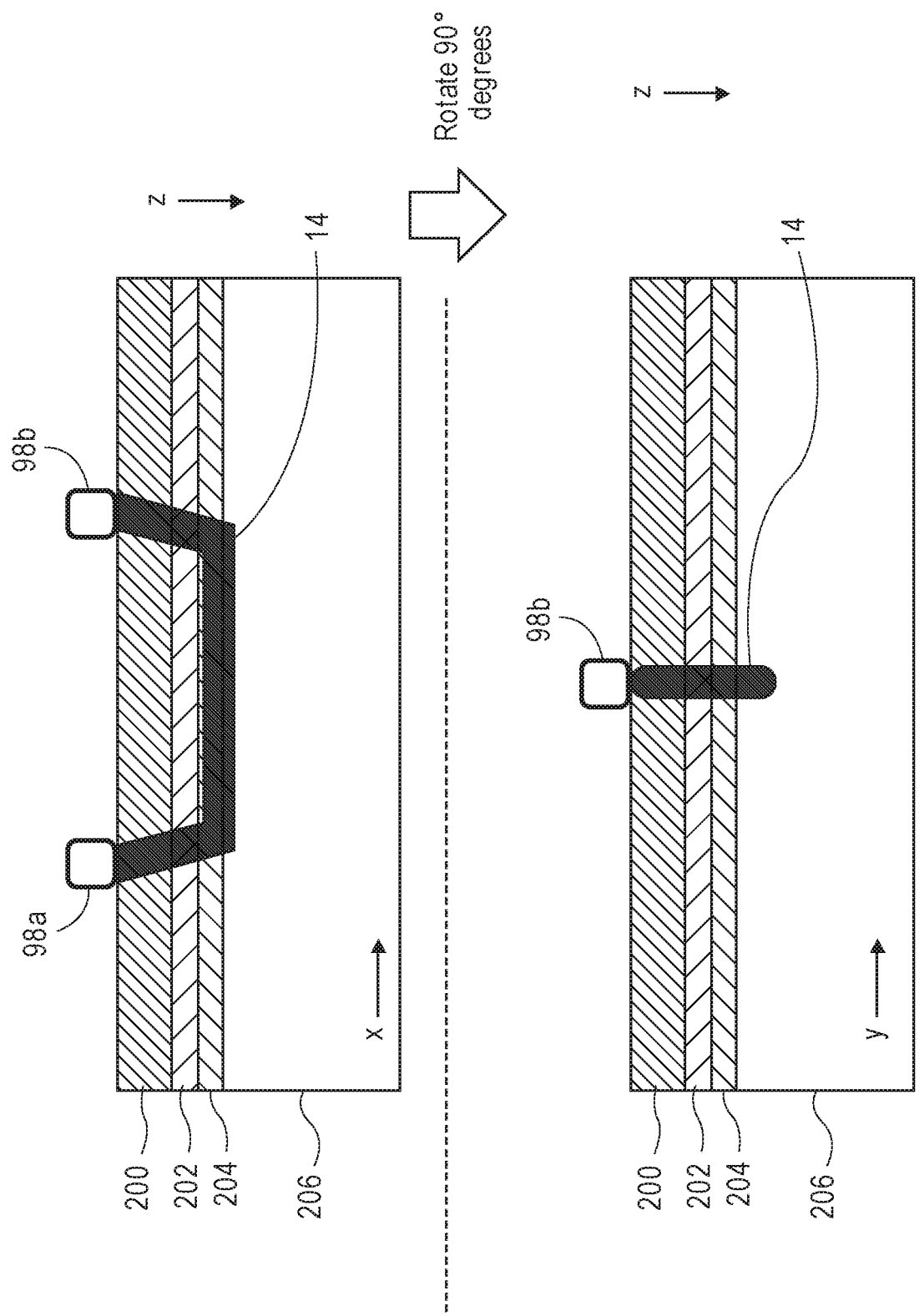
FIG. 26 are profile views of one arrangement of the output port and input port of the wearable unit of FIG. 25, particularly illustrating the creation of a target tissue voxel between the ports.

It should be appreciated that because the optical detection system 10 has been described as comprising a single fixed source-detector pair, in other words, a single output port 98a and a single input port 98b, it can only detect a physiologically-dependent optical parameter in the brain tissue 204 between the ports 98a, 98b, as illustrated in FIG. 26. The ports 98a, 98b are placed against the scalp 200 to detect regions of interest in the skull 202, cerebral spinal fluid (CSF) 204, and/or cortical brain tissue 206. The various optical paths may first pass through the scalp 200 and skull 202 along a relatively straight path, briefly enter the brain tissue 206, then exit along a relatively straight path. In the context of OCT, the reference arm in the interferometer 20 may be selected or adjusted (as described above with respect to FIG. 7) based on the distance between the ports 98a, 98b, and the depth of the target tissue voxel 15, and may, e.g., be approximately (or greater than) the sum of the distance between the ports 98a, 98b and twice the depth of the target tissue voxel 15. As depicted in the top half of FIG. 26, the greater distance of the target tissue voxel 15 may be across the X-Y plane as compared to its distance along the Z-direction.

In optional embodiments, the optical detection system 10 may be modified, such that it can sequentially or simultaneously detect physiologically-dependent optical parameters in multiple target tissue voxels 15 by tiling multiple source-detector pairs across the scalp 200. In this case, each target tissue voxel 15 is defined by a given output port 98a (which is associated with the optical source 50) at a given location and a given input port 98b (which is associated with the optical detectors 24) at a given location. Thus, multiple target tissue voxels 15 can be detected either by making the output port 98a movable relative to the input port 98b and/or spacing multiple input ports 98b from each other.

Figure 27:
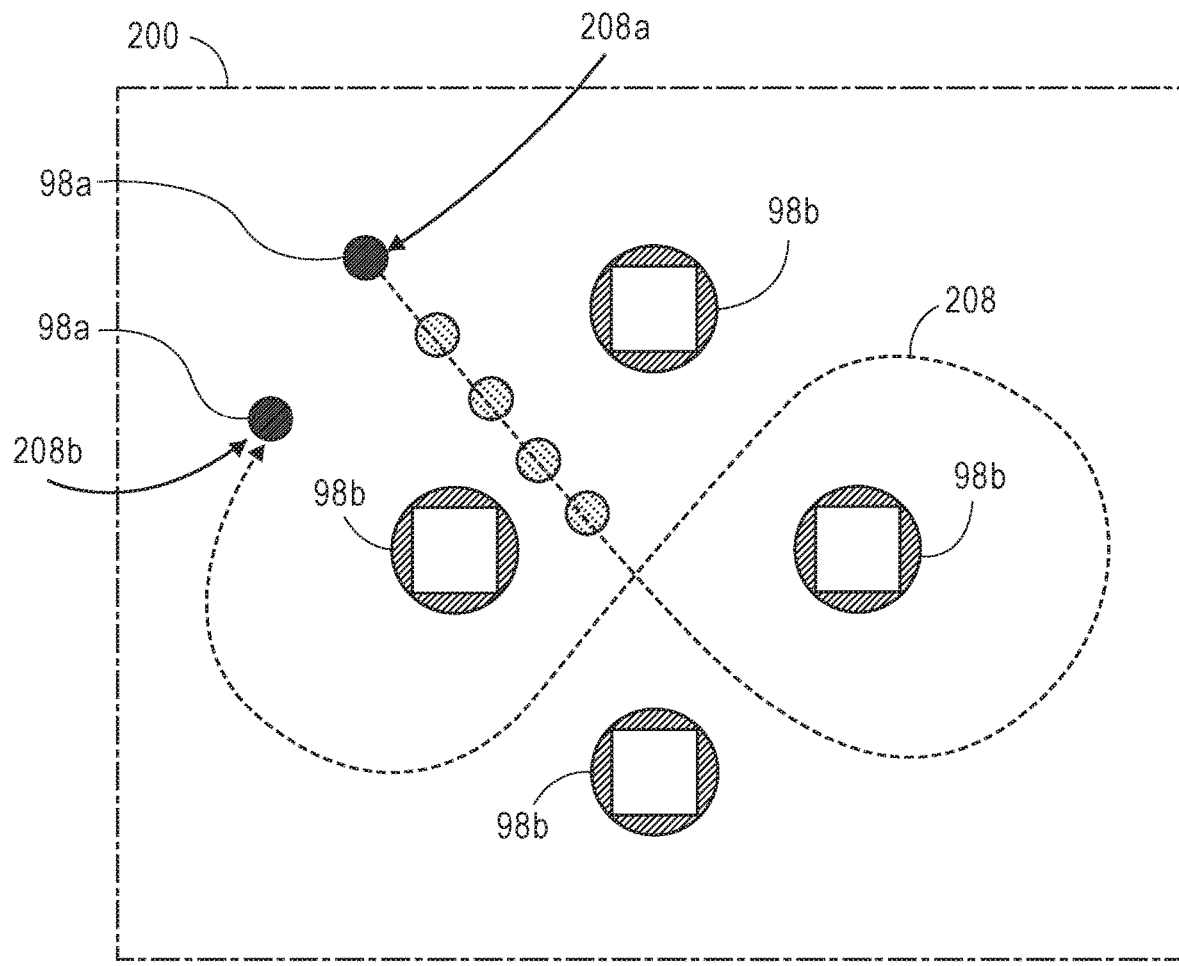
FIG. 27 is a plan view illustrating a modified arrangement of one movable output port and a multitude of fixed input ports that can be used in the wearable unit of FIG. 25, particularly illustrating a path along which the output port is moved around the input ports.
Figure 28:
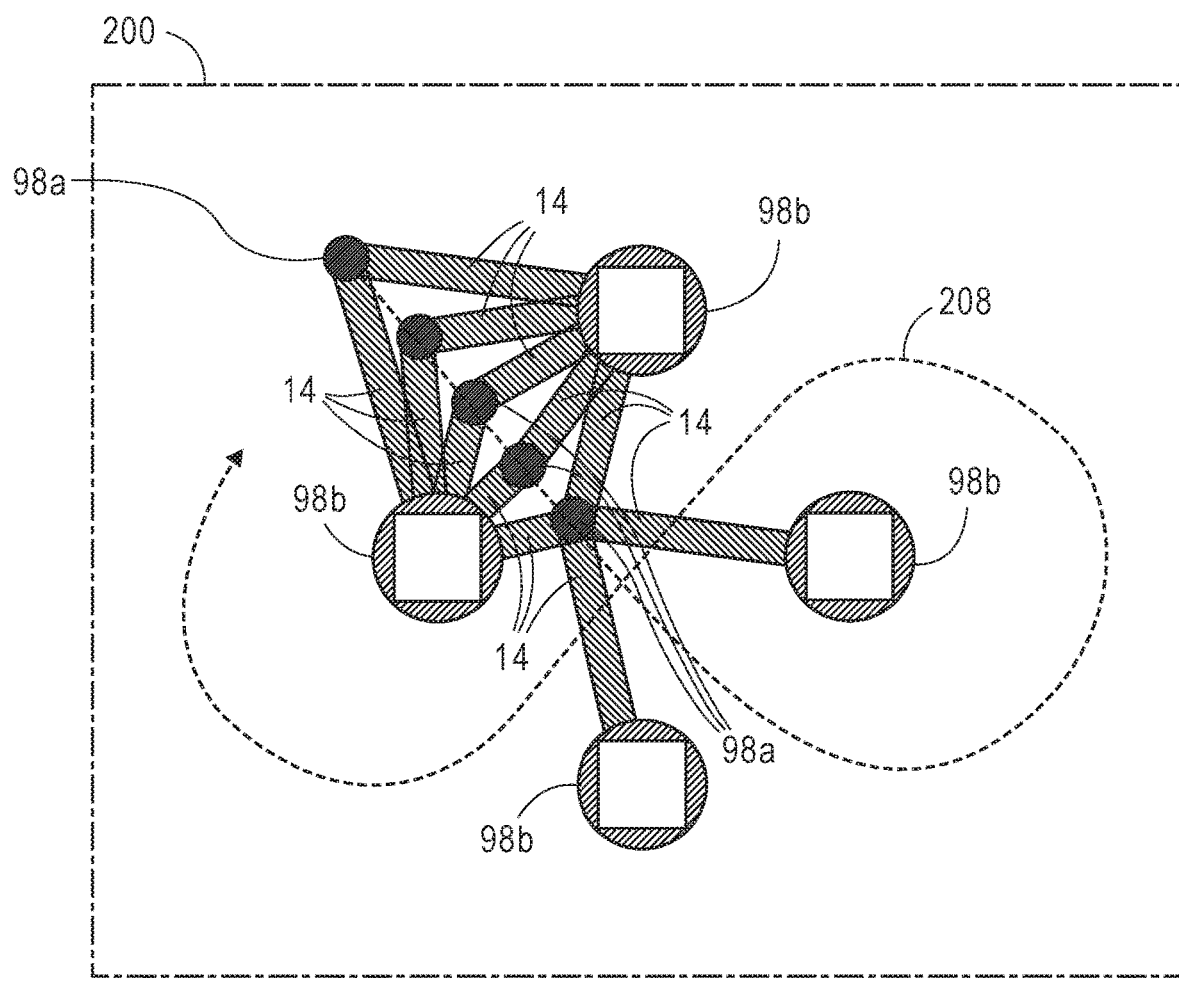
FIG. 28 is a plan view illustrating the modified arrangement of FIG. 27, particularly illustrating the creation of multiple target tissue voxels between the ports.

For example, with reference to FIG. 27, a plurality of input ports 98b are located at fixed positions on the scalp 200, and a single movable output port 98a may be moved around at different locations across the scalp 200 along a predetermined path 208 (e.g., from a first location 208a to a second location 208b) around the input ports 98b to distribute light into the target tissue voxel 15 from various locations on the surface of scalp 200. The input ports 98b may be arranged in any desirable pattern over the scalp 200. For example, they may be arranged or located in a symmetric or asymmetric array and/or may be arranged in a circular or radial pattern or a rectangular-shaped pattern. The field of view of the input ports 98b may have areas of overlap and/or may have little or no overlap. In some variations, the input ports 98b may be tiled adjacent to each other, such that the individual fields-of-view are adjacent to each other with little or no overlap. The aggregate of the individual fields-of-view may simulate a single camera with a large field-of-view.

In any arrangement, the light emitted by the output port 98a may be reflected and/or backscattered to the scalp 200 and enter the plurality of input ports 98b. In effect, this creates a multitude of target tissue voxels 15 through the brain tissue 206 (shown in FIG. 26) under the scalp 200 that are detected while the output port 98a moves along the path 208, as illustrated in FIG. 27. The multiple "crisscrossed" target tissue voxels 15 may facilitate the generation of a high-resolution functional map of the upper layer of cortex of the brain 206 with spatial resolution given by the XY plane (i.e., along the plane of the scalp 200) confinement of the paths and not limited by their lower Z confinement, in the manner of tomographic volume reconstruction, and in this method, defining the lateral cross-section of a bundle of tissue voxels as X-Y and the axial direction along Z. Moreover, moving the output port 98a with respect to the input ports 98b at one or more pre-determined locations may probe a region of interest from multiple angles and directions. That is, the output port 98*a* will be create multiple target tissue voxels 15 extending from the pre-determined location to the multiple input ports 98*b*, allowing optical data from the pre-determined location at the origin of the multiple tissue voxels to be acquired along multiple axes. Optical data taken across multiple axis across a region of interest may facilitate the generation of a 3-D map of the region of interest, such as from the tissue voxel. Optical data received by the input ports 98*b* may be used to generate detected optical properties with comparable resolution in the Z-direction (i.e., perpendicular to a scalp 200 as in the X-Y plane (i.e., along the scalp 200), and/or may allow optical probing or interrogation of larger region in brain tissue 206 (e.g., across multiple target tissue voxels 15 over a surface of the scalp).

Figure 29:
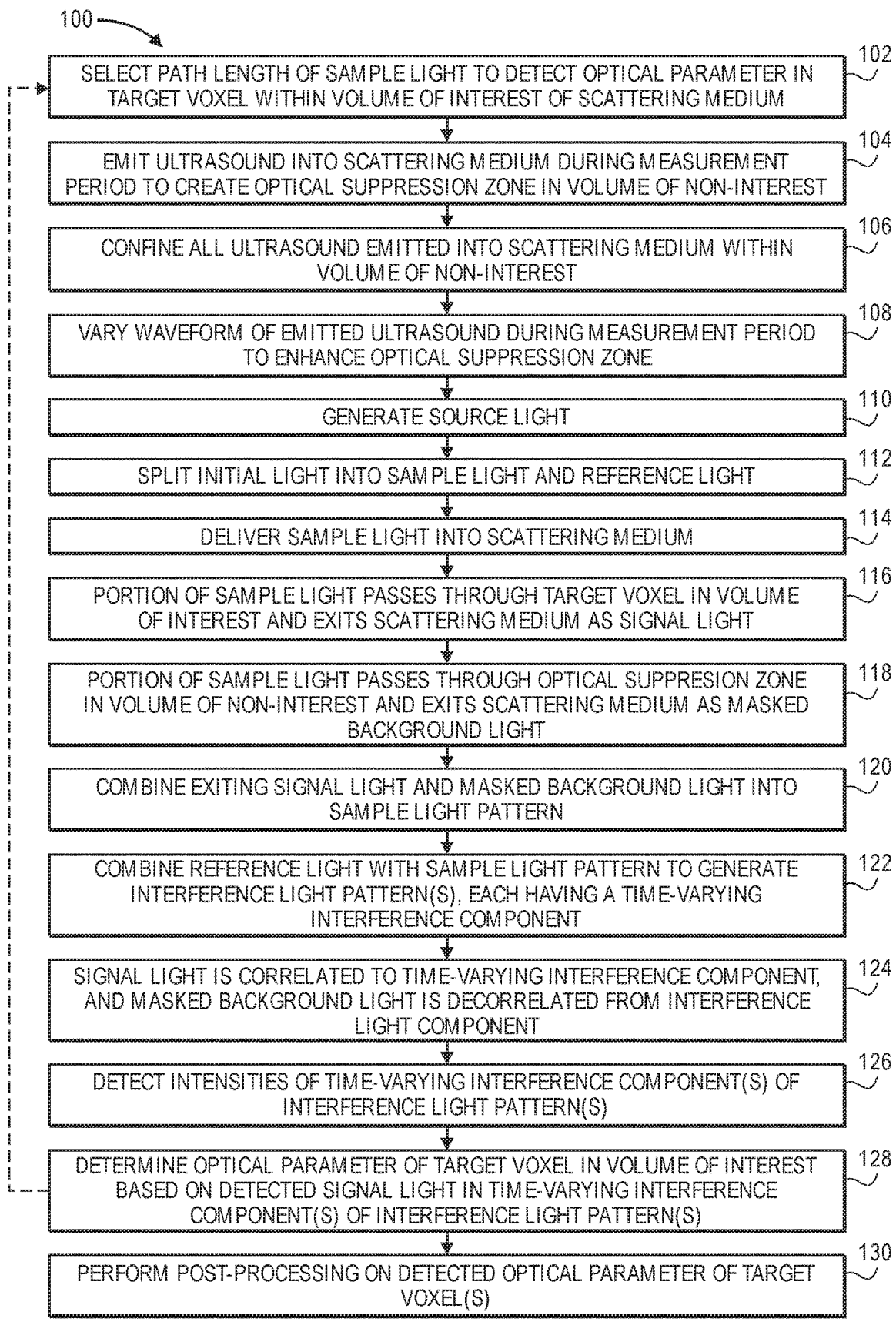
FIG. 29 is a flow diagram of one method used by the optical detection system of FIG. 6 to detect an optical parameter within a scattering medium.

Referring to FIG. 29, having described the structure and function of the optical detection system 10, one particular method 100 performed by the optical detection system 10 to non-invasively detect a target voxel 15 in the scattering medium 12 will now be described. In this example, the optical detection system 10 can be comparable to an OCT system.

The controller 26 first adjusts interferometer 20 to select the path length of the sample light 40 for detection of optical parameters within the target voxel 15 within the volume of interest 14 of the scattering medium 12, e.g., by sending a control signal to the path length adjustment mechanism 60, as shown in FIG. 8 (step 102). The controller 26 then operates the acoustic assembly 22 to emit ultrasound 32 into the scattering medium 12 during a measurement period, e.g., by sending a control signal to the signal generator 36, e.g., using techniques illustrated in FIGS. 11*a*-11*b* and 12*a*-12*b* (step 104). Next, all of the ultrasound 32 emitted into the scattering medium 12 during the measurement period is substantially confined within the volume of non-interest 16, e.g., using the techniques illustrated in FIGS. 15, 16*a*-16*c*, and 17*a*-17*c*, creating an optical masking zone 13 within the volume of non-interest 16 (step 106). Optionally, the controller 26 operates the acoustic assembly 22 to vary the waveform of the ultrasound 32 during the measurement period to further enhance the optical masking zone 13, e.g., using the techniques illustrated in FIGS. 13*b*-13*f* (step 108).

Then, the controller 26 operates the interferometer 22 to generate source light 38, e.g., by sending a control signal to the drive circuit to pulse the light source 50 on and off (step 110). The interferometer 22 (e.g., via the optical beam splitter 52) splits the source light 38 into sample light 40 and reference light 42 (step 112). The interferometer 22 then delivers the sample light 40 into the scattering medium 12, e.g., using techniques illustrated in FIGS. 11*a*-11*b* and 12*a*-12*b* (step 114). As the sample light 40 scatters diffusively through the scattering medium 12, a first portion 40*a* will pass through the target voxel 15 of the volume of interest 14 and exit the scattering medium 12 as signal light 44 (step 116), and a second portion 40*b* will pass through the optical masking zone 13 of the volume of non-interest 16 and exit the scattering medium 12 as masked background light 46 (step 118), as illustrated in FIGS. 6 and 7. As the signal light 44 and masked background light 46 exits the scattering medium 12, they combine to create a sample light pattern 47 (step 120).

Next, the interferometer 20 then combines (e.g., via the optical beam combiner 58) the reference light 42 with the sample light pattern 47 to generate one or more interference light patterns 48, each having a holographic beat component (step 122). The signal light 44 in the sample light pattern 47 is correlated to the holographic beat component of each interference light pattern 48, while the masked background light 46 in the sample light pattern 47 is decorrelated, preventing it from contributing to holographic beat component of each interference light pattern 48 (step 124), such that it does not contribute to holographic interference, but rather generates a rapidly time-varying signal component that integrates to approximately zero during the detection time. Then, under control of the controller 24, the detector(s) 24 detect the intensities of the holographic beat component(s) of the interference light pattern(s) 48, which corresponds to the intensity of the signal light 44 (step 126). The combination of the reference light 42 with the sample light pattern 47 to generate the interference light pattern(s) 48, and subsequent detection of the holographic beat component of each interference light pattern 48 can be performed using the techniques illustrated in FIGS. 21-24.

The processor 30 then determines the optical parameter of target voxel 15 in the volume of interest 14 based on the detected signal light 44 in the holographic beat component of each interference light pattern 48 (step 128). The path length of the sample light 40 can be repeatedly adjusted for detection of optical parameters within other tissue voxels 15 within the volume of interest 14 of the scattering medium 12 in step 102, and steps 104-128 can be repeated to determine optical parameters of the other target voxels 15. The ultrasound 32 can be emitted into different volumes of non-interest 16 as illustrated in FIGS. 18*a*-18*c* and 19*a*-19*c*.

The processor 30 may then perform post-processing on the determined optical parameters (step 130), and in the case where the target voxel 15 is brain matter, such post-processing comprising determining the level of neural activity within the target voxel 15 based on the determined optical parameter of the target voxel(s) 15.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:
1. A non-invasive optical detection system, comprising:
an acoustic assembly configured for emitting ultrasound to create an optical masking zone in a volume of non-interest of a scattering medium;
an interferometer configured for delivering sample light, during a measurement period, into the scattering medium further having a volume of interest, such that a first portion of the sample light passes through the volume of interest without passing through the optical masking zone in the volume of non-interest and without being tagged by the emitted ultrasound, and exits the scattering medium as signal light, and a second portion of the sample light passes through the optical masking zone in the volume of non-interest and exits the scattering medium as background light that is combined with the signal light to create a sample light pattern, the interferometer further configured for combining reference light with the sample light pattern to create at least one interference light pattern, each having a holographic beat component, wherein the optical masking zone decorrelates at least a portion of the background light of the sample light pattern from the holographic beat component of each of the at least one interference light pattern;

at least one detector configured for detecting the holographic beat component of each of the at least one interference light pattern during the measurement period; and a processor configured for determining an optical parameter of the volume of interest based on the detected holographic beat component of each of the at least one interference light pattern.

2. The non-invasive optical detection system of claim 1, wherein the optical mask zone decorrelates substantially all of the background light of the sample light pattern from the holographic beat component of each of the at least one interference light pattern.

3. The non-invasive optical detection system of claim 1, wherein the optical masking zone decorrelates at least ninety-nine percent of the background light of the sample light pattern from the holographic beat component of each of the at least one interference light pattern.

4. The non-invasive optical detection system of claim 1, wherein the scattering medium is an anatomical structure, the volume of interest comprises a target tissue voxel within the anatomical structure, and the optical parameter is a physiologically-dependent optical parameter of the target tissue voxel.

5. The non-invasive optical detection system of claim 4, wherein the physiologically-dependent optical parameter is the level of deoxygenated and/or oxygenated hemoglobin concentration or relative abundance.

6. The non-invasive optical detection system of claim 4, wherein the target tissue voxel comprises grey matter of a brain matter, and the volume of non-interest comprise a scalp and skull.

7. The non-invasive optical detection system of claim 6, wherein the processor is further configured for determining neural activity within the target tissue voxel based on the determined physiologically-dependent optical parameter.

8. The non-invasive optical detection system of claim 7, wherein the physiologically-dependent optical parameter is a fast-optical signal.

9. The non-invasive optical detection system of claim 1, wherein the at least one interference light pattern comprises a plurality of phase-modulated interference light patterns.

10. The non-invasive optical detection system of claim 1, wherein the interferometer is configured for combining the sample light pattern and the reference light using a homodyne technique.

11. The non-invasive optical detection system of claim 1, wherein the interferometer is configured for combining the sample light pattern and the reference light using a heterodyne technique.

12. The non-invasive optical detection system of claim 1, wherein each of the at least one interference light pattern comprises spatial components, and wherein each of the at least one detector comprises an array of detector pixels respectively configured for detecting intensities of the spatial components of the at least one interference light pattern.

13. The non-invasive optical detection system of claim 1, wherein the interferometer comprises a reference arm along which the reference light propagates, and a sample arm along which the sample light propagates, the reference arm and sample arm having optical path lengths that match within a coherence length of the sample light, wherein the frequency of the sample light and the reference light are the same, such that the holographic beat component of each of the at least one interference light pattern is constant.

14. The non-invasive optical detection system of claim 13, wherein the optical path length of the reference arm of the interferometer is adjustable, and further comprising a controller configured for operating the interferometer to adjust the optical path length of the reference arm.

15. The non-invasive optical detection system of claim 1, wherein each of the at least one interference light pattern comprises a speckle light pattern.

16. The non-invasive optical detection system of claim 1, wherein the interferometer comprises an optical source configured for generating source light, and an optical beam splitter configured for splitting the source light into the sample light and the reference light.

17. The non-invasive optical detection system of claim 1, wherein the acoustic assembly comprises a single-element ultrasound transducer configured for emitting the ultrasound into the volume of non-interest.

18. The non-invasive optical detection system of claim 17, wherein the single-element ultrasound transducer is a thin-film ultrasound transducer.

19. The non-invasive optical detection system of claim 18, wherein the thin-film ultrasound transducer comprises one of a capacitive micromachined ultrasound transducer (CMUT) and a piezo micromachined ultrasound transducers (PMUT).

20. The non-invasive optical detection system of claim 1, wherein the ultrasound has a frequency greater than 1 MHz.

21. The non-invasive optical detection system of claim 1, wherein the ultrasound has a frequency in the range of 5-20 MHz.

22. The non-invasive optical detection system of claim 1, wherein the ultrasound is unfocused.

23. The non-invasive optical detection system of claim 1, wherein the ultrasound has a uniform frequency, a uniform amplitude, and a uniform phase during the measurement period.

24. The non-invasive optical detection system of claim 1, further comprising a controller configured for operating the acoustic assembly to vary at least one of a frequency, an amplitude, and a phase during the measurement period.

25. The non-invasive optical detection system of claim 24, wherein the controller is configured for operating the acoustic assembly to vary at least two of the frequency, the amplitude, and the phase of the ultrasound during the measurement period.

26. The non-invasive optical detection system of claim 25, wherein the controller is configured for operating the acoustic assembly to vary the frequency of the ultrasound during the measurement period.

27. The non-invasive optical detection system of claim 26, wherein the controller is configured for operating the acoustic assembly to sweep the frequency of the ultrasound during the measurement period.

28. The non-invasive optical detection system of claim 26, wherein the controller is configured for operating the acoustic assembly to randomly vary the frequency of the ultrasound during the measurement period.

29. The non-invasive optical detection system of claim 1, wherein the ultrasound is continuous wave (CW) ultrasound that has a frequency, such that the optical masking zone is substantially confined within the volume of non-interest during the measurement period.

30. The non-invasive optical detection system of claim 1, wherein the ultrasound is pulsed wave (PW) ultrasound that has a frequency that allows it to penetrate into the volume of interest, the non-invasive optical detection further comprising a controller configured for operating the interferometer and the acoustic assembly to pulse the sample light and the ultrasound in synchrony during the measurement period, such that the optical masking zone is substantially confined within the volume of non-interest during the measurement period, but extends into the volume of interest outside of the measurement period.

31. The non-invasive optical detection system of claim 1, wherein the volume of interest is a first volume of interest, the volume of non-interest is a first volume of non-interest, the optical masking zone is a first optical masking zone, the measurement period is a first measurement period, the sample light is a first sample light, the signal light is first signal light, and the at least one interference light pattern is a first at least one interference light pattern;

wherein the acoustic assembly is further configured for emitting ultrasound to create a second optical masking zone in a second volume of non-interest of the scattering medium;

wherein the interferometer is configured for emitting the sample light into the scattering medium having a second volume of interest and the second volume of non-interest during a second measurement period, such that a first portion of the second sample light passes through the second volume of interest without passing through the second optical masking zone, and exits the scattering medium as second signal light, and a second portion of the second sample light passes through the second optical masing zone in the second volume of non-interest and exits the scattering medium as background light that is combined with the second signal light to create a second sample light pattern, the interferometer further configured for combining the reference light with the second sample light pattern to create a second at least one interference light pattern, each having a holographic beat component;

wherein the second masking zone decorrelates at least a portion of the background light of the sample light pattern from the holographic beat component of each of the second at least one interference light pattern;

wherein the at least one detector is configured for detecting the holographic beat component of each of the second at least one interference light pattern during the second measurement period; and wherein the processor is configured for determining an optical parameter of the second volume of interest based on detected holographic beat component of each of the second at least one interference light pattern.

32. The non-invasive optical detection system of claim 31, wherein the first volume of non-interest has a first depth in the scattering medium, and the second volume of non-interest has a second depth in the scattering medium greater than the first depth.

33. The non-invasive optical detection system of claim 32, wherein the ultrasound is continuous wave (CW) ultrasound, and further comprising a controller configured for operating the acoustic assembly to vary a frequency of the ultrasound to have a first frequency, such that the first optical masking zone is substantially confined within the first volume of non-interest during the first measurement period, and to have a second frequency, such that the second optical masking zone is substantially confined within the second volume of non-interest during the second measurement period.

34. The non-invasive optical detection system of claim 32, wherein the ultrasound is pulsed wave (PW) ultrasound that has a frequency that allows it to penetrate into the first volume of interest and the second volume of interest, and further comprising a controller configured for operating the interferometer and the acoustic assembly to pulse the sample light and the ultrasound in synchrony, such that the first optical masking zone is substantially confined within the first volume of non-interest during the first measurement period, and the second optical masking zone is substantially confined within the second volume of non-interest during the second measurement period.

35. The non-invasive optical detection system of claim 1, wherein the volume of non-interest has a first depth in the scattering medium, and the volume of interest has a second depth in the scattering medium greater than the first depth.

36. A non-invasive optical detection method, comprising:
emitting ultrasound to create an optical masking zone in a volume of non-interest of a scattering medium;
delivering sample light, during a measurement period, into the scattering medium having a volume of interest, such that a first portion of the sample light passes through the volume of interest without passing through the optical masking zone in the volume of non-interest and without being tagged by the emitted ultrasound, and exits the scattering medium as signal light, and a second portion of the sample light passes through the optical masking zone in the volume of non-interest and exits the scattering medium as background light that is combined with the signal light to create a sample light pattern;
combining reference light with the sample light pattern to create at least one interference light pattern, each having a holographic beat component, wherein the optical masking zone decorrelates at least a portion of the background light of the sample light pattern from the holographic beat component of each of the at least one interference light pattern;
detecting the holographic beat component of each of the at least one interference light pattern during the measurement period; and
determining an optical parameter of the volume of interest based on detected holographic beat component of each of the at least one interference light pattern.

37. The non-invasive optical detection method of claim 36, wherein the optical masking zone decorrelates substantially all of the background light of the sample light pattern from the holographic beat component of each of the at least one interference light pattern.

38. The non-invasive optical detection method of claim 36, wherein the optical masking zone decorrelates at least ninety-nine percent of the background light of the sample light pattern from the holographic beat component of each of the at least one interference light pattern.

39. The non-invasive optical detection method of claim 36, wherein the scattering medium is an anatomical structure, the volume of interest comprises a target tissue voxel within the anatomical structure, and the optical parameter is a physiologically-dependent optical parameter of the target tissue voxel.

40. The non-invasive optical detection method of claim 39, wherein the physiologically-dependent optical parameter is the level of deoxygenated and/or oxygenated hemoglobin concentration or relative abundance.

41. The non-invasive optical detection method of claim 39, wherein the target tissue voxel comprises grey matter of a brain matter, and the volume of non-interest comprise a scalp and skull.

42. The non-invasive optical detection method of claim 41, further comprising determining neural activity within the target tissue voxel based on the determined physiologically-dependent optical parameter.

43. The non-invasive optical detection method of claim 42, wherein the physiologically-dependent optical parameter is a fast-optical signal.

44. The non-invasive optical detection method of claim 36, wherein the volume of non-interest has a first depth in the scattering medium, and the volume of interest has a second depth in the scattering medium greater than the first depth.

* * * * *